US011896617B2

(12) United States Patent
Pertel et al.

(10) Patent No.: US 11,896,617 B2
(45) Date of Patent: Feb. 13, 2024

(54) POLYNUCLEOTIDES ENCODING RITUXIMAB-RESISTANT CHIMERIC ANTIGEN RECEPTORS

(71) Applicant: ALLOGENE THERAPEUTICS, INC., South San Francisco, CA (US)

(72) Inventors: Thomas Charles Pertel, San Mateo, CA (US); Barbra Johnson Sasu, San Francisco, CA (US); Mark W. Leonard, Burlingame, CA (US)

(73) Assignee: ALLOGENE THERAPEUTICS, INC., South San Francisco, CA (US)

( * ) Notice: Subject to any disclaimer, the term of this patent is extended or adjusted under 35 U.S.C. 154(b) by 605 days.

(21) Appl. No.: 16/857,573

(22) Filed: Apr. 24, 2020

(65) Prior Publication Data

US 2020/0384026 A1    Dec. 10, 2020

Related U.S. Application Data

(60) Provisional application No. 63/005,041, filed on Apr. 3, 2020, provisional application No. 62/839,455, filed on Apr. 26, 2019.

(51) Int. Cl.
*C12N 15/62* (2006.01)
*A61K 35/17* (2015.01)
(Continued)

(52) U.S. Cl.
CPC ............. *A61K 35/17* (2013.01); *A61P 35/00* (2018.01); *C07K 14/70517* (2013.01);
(Continued)

(58) Field of Classification Search
None
See application file for complete search history.

(56) References Cited

U.S. PATENT DOCUMENTS 5,830,462 A   11/1998   Crabtree et al.
5,834,266 A   11/1998   Crabtree et al.
(Continued)

FOREIGN PATENT DOCUMENTS

WO   2003029412 A2    9/2002
WO   WO2013153391 A1  10/2013
(Continued)

OTHER PUBLICATIONS

Bai et al., Enhancement of the in vivo persistence and antitumor efficacy of CD19 chimeric antigen receptor T cells through the delivery of modified TERT mRNA:,Cell Discov. 1, 15040; doi:10.1038/celldisc.2015.40, 15 pages and Suppl Info and Figs., Dec. 2015.*

(Continued)

*Primary Examiner* — Claire Kaufman
(74) *Attorney, Agent, or Firm* — Allogene Therapeutics, Inc.

(57) ABSTRACT

Provided herein are polynucleotides encoding chimeric antigen receptors (CARs) comprising a CD19 antigen binding domain that specifically binds to CD19 and is resistant to rituximab binding; and immune cells comprising these CD19-specific CARs, e.g., CAR-T cells. Also provided are methods of making and using these CD19-specific CARs, and immune cells comprising these CD19-specific CARs.

23 Claims, 30 Drawing Sheets

Specification includes a Sequence Listing.

(51) Int. Cl.
| | |
|---|---|
| *A61P 35/00* | (2006.01) |
| *C07K 14/705* | (2006.01) |
| *C07K 16/28* | (2006.01) |
| *C12N 5/0783* | (2010.01) |
| *A61K 39/00* | (2006.01) |

(52) U.S. Cl.
CPC .... *C07K 14/70596* (2013.01); *C07K 16/2803* (2013.01); *C12N 5/0636* (2013.01); *A61K 2039/505* (2013.01); *C07K 2317/76* (2013.01); *C07K 2319/33* (2013.01); *C12N 2510/00* (2013.01); *C12N 2740/15043* (2013.01)

(56) References Cited

U.S. PATENT DOCUMENTS

| | | | |
|---|---|---|---|
| 5,869,337 | A | 2/1999 | Crabtree et al. |
| 6,165,787 | A | 12/2000 | Crabtree et al. |
| 6,319,494 | B1 | 11/2001 | Capon et al. |
| 7,741,465 | B1 | 6/2010 | Eshhar et al. |
| 8,436,183 | B2 | 5/2013 | Holt et al. |
| 8,486,693 | B2 | 7/2013 | Park et al. |
| 9,024,028 | B2 | 5/2015 | Li et al. |
| 9,944,690 | B2 | 4/2018 | Spencer et al. |
| 10,428,142 | B2 | 10/2019 | Jarjour et al. |
| 10,874,693 | B2 * | 12/2020 | Galetto ............ C07K 14/70517 |
| 10,888,608 | B2 * | 1/2021 | Spencer ......... A61K 39/001195 |
| 2011/0286980 | A1 | 11/2011 | Brenner |
| 2016/0046700 | A1 | 2/2016 | Foster et al. |
| 2018/0319854 | A1 * | 11/2018 | Gummadova ... C07K 14/43509 |
| 2021/0213119 | A1 * | 7/2021 | Wang .................... C12N 15/86 |

FOREIGN PATENT DOCUMENTS

| | | |
|---|---|---|
| WO | WO2014127261 A1 | 8/2014 |
| WO | WO2014184143 A1 | 11/2014 |
| WO | WO2015090229 A1 | 6/2015 |
| WO | WO2015120096 | 8/2015 |
| WO | WO2016120216 A1 | 8/2016 |
| WO | WO2017180587 A2 | 4/2017 |
| WO | 2017103613 A1 | 6/2017 |
| WO | 2017207979 A1 | 12/2017 |
| WO | WO2018161017 A1 | 9/2018 |
| WO | 2019209869 A2 | 10/2019 |

OTHER PUBLICATIONS

G&P Biosciences, Product ID: CD19-CART-2G40, Retrieved online: <URL: https://www.gnpbio.com/index.php/products/1567/15/lentiviral-expression-system/anti-cd19-chimeric-antigen-receptor-t-cell-car-t-lentivirus-2nd-generation-scfv-cd19-ox40-cd3zeta-pre-packaged-lentiviral-particles-detail> on Nov. 18, 2022, 2018.*

Brenner, Malcom K., et al., "Adoptive T Cell Therapy of Cancer", Curr Opin Immunol. Apr. 2010 ; 22(2): 251-257. doi:10.1016/j.coi.2010.01.020.

Eshhar, Zelig , et al., "Specific activation and targeting of cytotoxic lymphocytes through chimeric single chains consisting of antibody-binding domains and the gamma or zeta subunits of the immuno-globulin and T-cell receptors.", Immunology; Proc Natl Acad Sci U S A. Jan. 15, 1993; 90(2): 720-724.

Finney, Helen , et al., "Chimeric Receptors Providing Both Primary and Costimulatory Signaling in T Cells from a Single Gene Product", J Immunol Sep. 15, 1998, 161 (6) 2791-2797.

Gross, Gideon , et al., "Therapeutic Potential of T Cell Chimeric Antigen Receptors (CARs) in Cancer Treatment: Counteracting Off-Tumor Toxicities for Safe CAR T Cell Therapy", Annual Review of Pharmacology and Toxicology; vol. 56:59-83 (Volume publication date Jan. 2016) https://doi.org/10.1146/annurev-pharmtox-010814-124844.

Kalos, Michael , et al., "T Cells with Chimeric Antigen Receptors Have Potent Antitumor Effects and Can Establish Memory in Patients with Advanced Leukemia", Science Transnational Medicine, vol. 3 Issue 95 95ra73, 2011.

Krause, Anja , et al., "Antigen-dependent CD28 Signaling Selectively Enhances Survival and Proliferation in Genetically Modified Activated Human Primary T Lymphocytes", The Journal of experimental medicine vol. 188,4 (1998): 619-26. doi:10.1084/jem.188.4.619.

Milone, Michael C., et al., "Chimeric Receptors Containing CD137 Signal Transduction Domains Mediate Enhanced Survival of T Cells and Increased Antileukemic Efficacy In Vivo", Molecular Therapy vol. 17 No. 8, 1453-1464 Aug. 2009.

Montiel-Equiha, Claudia A., et al., "The β-globin locus control region in combination with the EF1α short promoter allows enhanced lentiviral vector-mediated erythroid gene expression with conserved multilineage activity.", Mol Ther. 2012;20(7):1400-1409. doi:10.1038/mt.2012.50.

Porter, David L., et al., "Chimeric Antigen Receptor-Modified T Cells in Chronic Lymphoid Leukemia", N Engl J Med 2011;365:725-33.

Rosenberg, Steven A., et al., "Adoptive cell transfer: a clinical path to effective cancer immunotherapy", Nat Rev Cancer. Apr. 2008 ; 8(4): 299-308. doi:10.1038/nrc2355.

Sadelain, Michel , et al., "The promise and potential pitfalls of chimeric antigen receptors", Current Opinion in Immunology 2009, 21:215-223.

Song, De-Gang , et al., "CD27 costimulation augments the survival and antitumor activity of redirected human T cells in vivo", Blood (2012) 119 (3): 696-706.

Wakabayashi-Ito, Noriko , et al., "Characterization of the regulatory elements in the promoter of the human elongation factor-1 alpha gene", J Biol Chem . Nov. 25, 1994;269(47):29831-7.

Ying, Zhitao , et al., "A safe and potent anti-CD19 CAR T cell therapy", Nat Med 25, 947-953 (2019). https://doi.org/10.1038/s41591-019-0421-7.

Ying, Zhitao , et al., "A safe and potent anti-CD19 CAR T cell therapy (Supplementary Information)", A safe and potent anti-CD19 CAR T cell therapy, Nat. Med. 25(6) : 947-953, Supplemental Information (2019).

EPO, International Search Report & Written Opinion dated Jun. 30, 2020 for International Application No. PCT/US2020/029775.

Roddie, Claire , et al., "Manufacturing chimeric antigen receptor T cells: issues and challenges", Cytotherapy; 2019 21(3):327-340; DOI: 10.1016/j.jcyt.2018.11.009.

Sanber, Khaled S., et al., "Construction of stable packaging cell lines for clinical lentiviral vector production", Sci Rep 5, 9021 (2015). https://doi.org/10.1038/srep09021.

Charrier, S , et al., "Lentiviral vectors targeting WASp expression to hematopoietic cells, efficiently transduce and correct cells from WAS patients", Gene Therapy; 14, 415-428 (2007); DOI: https://doi.org/10.1038/sj.gt.3302863.

De Oliveira, Satiro N., et al., "A CD19/Fc fusion protein for detection of anti-CD19 chimeric antigen receptors", Journal of Translational Medicine 2013, 11:23; http://www.translational-medicine.com/content/11/1/23.

Kloss, Christopher C., et al., "Dominant-Negative TGF-b Receptor Enhances PSMA-Targeted Human CAR T Cell Proliferation and Augments Prostate Cancer Eradication", Original Article| vol. 26, Issue 7, p. 1855-1866, Jul. 5, 2018.

Larson, Sarah M., et al., "Pre-clinical development of gene modification of haematopoietic stem cells with chimeric antigen receptors for cancer immunotherapy", Human Vaccines & Immunotherapeutics; 2017, vol. 13, No. 5, 1094-1104; http://dx.doi.org/10.1080/21645515.2016.1268745.

* cited by examiner

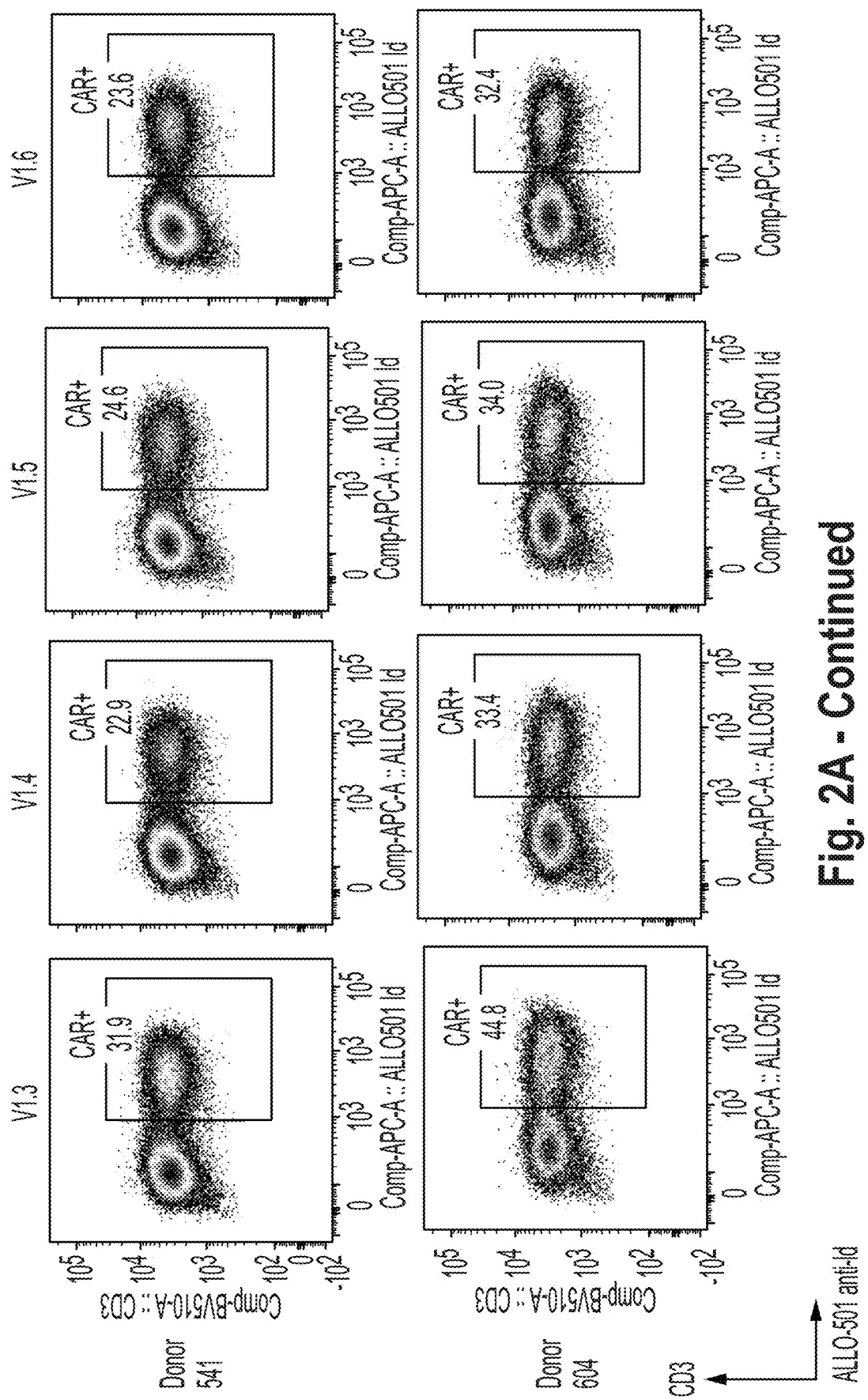
Fig. 2A - Continued

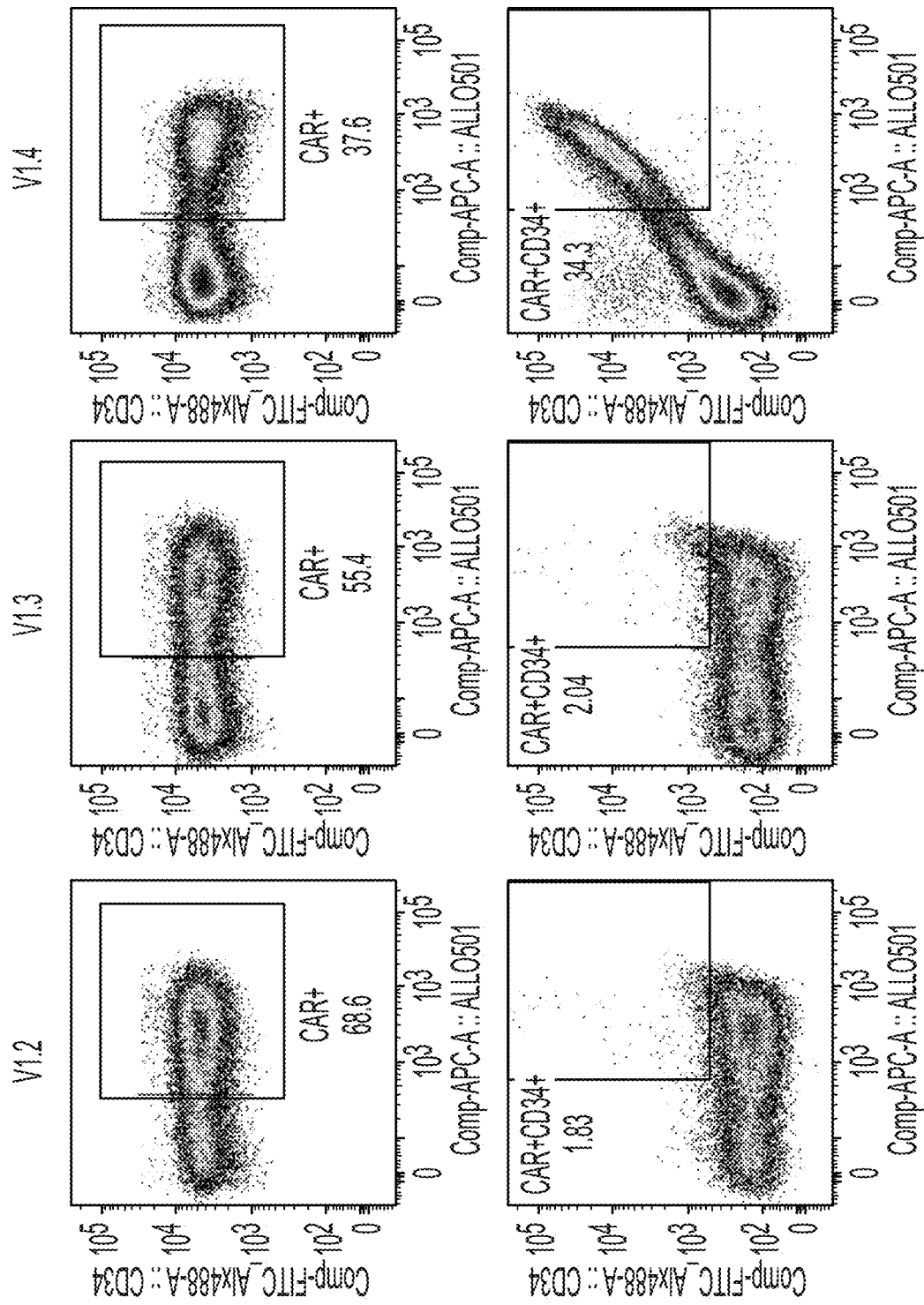
Fig. 2B - Continued

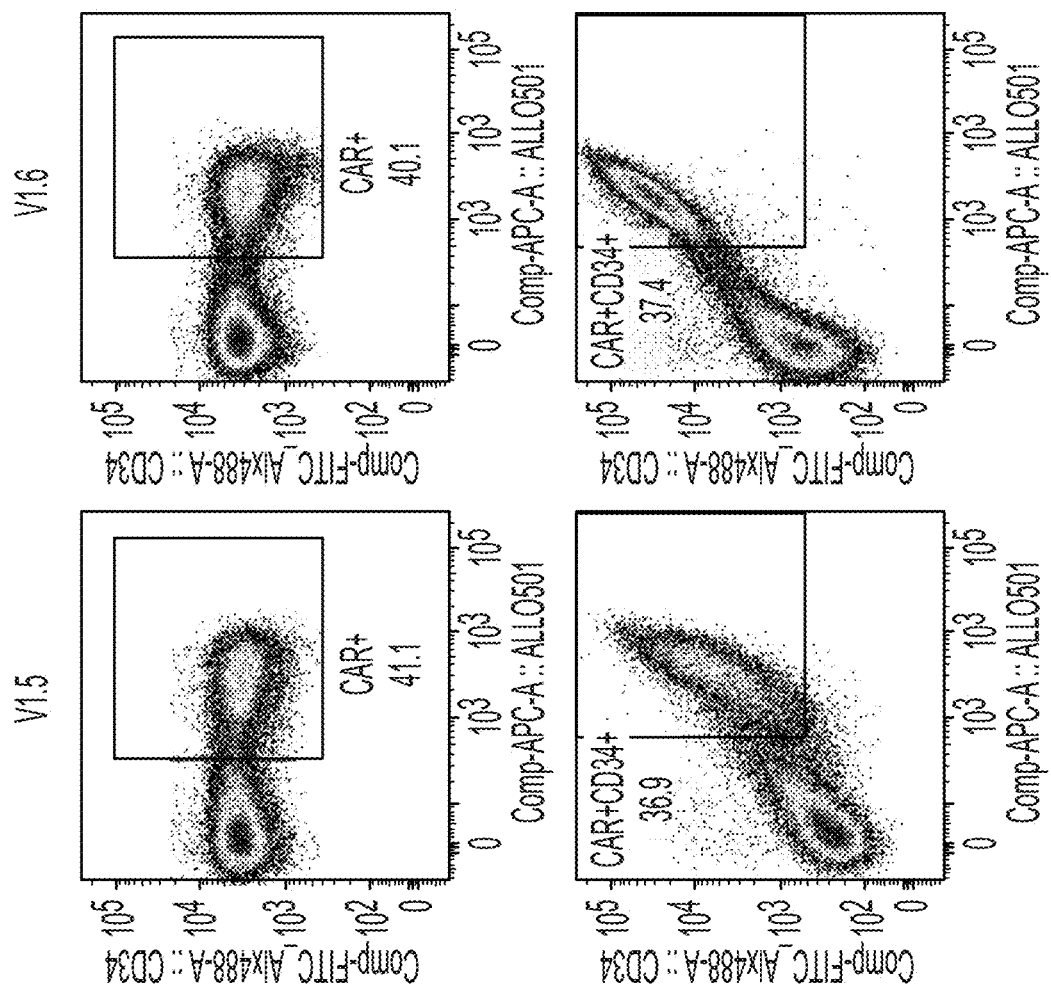
Fig. 2B - Continued

SEQUENCE LISTING

<160> NUMBER OF SEQ ID NOS: 41

<210> SEQ ID NO 1
<211> LENGTH: 2019
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: chimeric antigen receptor

<400> SEQUENCE: 1
atgctgacca gcctgctgtg ctggatggcc ctgtgcctgc tgggcgccga ccacgccgat      60
gcctgcccct acagcaaccc cagcctgtgc agcggaggcg gcggcagcga gctgccacc     120 cagggcacct tctccaacgt gtccaccaac gtgagcccag ccaagccac caccaccgcc     180 tgtccttatt ccaatccttc cctgtgtagc ggaggggag gcagcccagc cccagacct     240 cccaccccag cccccaccat cgccagccag cctctgagcc tgagaccga ggcctgccgc     300 ccagccgccg gcggcgccgt gcacaccaga ggcctggatt tcgcctgcga tatctacatc     360

```
tgggccccac tggccggcac ctgtggcgtg ctgctgctga gcctggtgat caccctgtac      420
tgcaaccacc gcaaccgcag gcgcgtgtgc aagtgcccca ggcccgtggt gagagccgag      480
ggcagaggca gcctgctgac ctgcggcgac gtggaggaga cccaggccc catggagacc       540 gacaccctgc tgctgtgggt gctgctgctg tgggtgccag cagcaccgg cgaggtgcag       600 ctgcagcaga gcggacccga gctgatcaag ccaggcgcca gcgtgaagat gagctgcaag      660
gccagcggct acaccttcac cagctacgtg atgcactggg tgaagcagaa gccaggccag      720
ggcctggagt ggatcggcta catcaacccc tacaacgacg gcaccaagta acgagaag       780 ttcaagggca aggccaccct gaccagcgac aagagcagca gcaccgccta catggagctg      840
agcagcctga ccagcgagga cagcgccgtg tactactgcg ccagaggcac ctactactac      900
ggcagccggg tgttcgacta ctggggccag ggcaccaccc tgaccgtgag ctctggcgga      960
ggcggctctg gcggaggcgg ctctggcgga ggcggcagcg acatcgtgat gacccaggct     1020
gcccccagca tccccgtgac cccaggcgag agcgtgagca tcagctgccg gagcagcaag     1080
agcctgctga acagcaacgg caacacctac ctgtactggt tcctgcagcg gccaggccag     1140
agcccccagc tgctgatcta ccggatgagc aacctggcca gcggcgtgcc cgaccggttc     1200
agcggcagcg gcagcggcac cgccttcacc ctgcggatca gccgggtgga ggccgaggac     1260
gtgggcgtgt actactgcat gcagcacctg gagtacccct tcaccttcgg agccggcacc     1320
aagctggagc tgaagcggtc ggatcccacc accacccccag ccccacggcc acctacccct    1380
gccccaacca tcgccagcca gcccctgagc ctgcggcctg aagcctgcag gcctgccgcc     1440
ggaggagccg tgcacacaag gggcctggac ttcgcctgcg acatctatat ctgggccccc     1500
ctggccggga catgcggggt gctgctgctg tccctggtga ttacactgta ttgcaaacgg     1560
ggccggaaga agctgctgta catcttcaag cagcccttca tgcggcccgt gcagaccacc     1620
caggaggagg acggctgcag ctgccggttc cccgaggaag aggaaggcgg ctgcgagctg     1680
cgggtgaagt tcagccggag cgccgacgcc ccagcctacc agcagggcca gaaccagctg     1740
tacaacgagc tgaacctggg acggcgggag gagtacgacg tgctggacaa gcggcgggga     1800
cgggaccccg agatgggcgg caagcctcgc cggaagaatc cccaggaggg cctgtacaac     1860
gagctgcaga aggacaagat ggccgaggcc tacagcgaga tcggcatgaa gggcgagcgg     1920
cgccggggca agggccacga cggcctgtac cagggcctga gcaccgccac caaggacacc     1980
tacgacgccc tgcacatgca ggccctgcca ccccggtga                            2019
```

<210> SEQ ID NO 2
<211> LENGTH: 1488
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: chimeric antigen receptor

<400> SEQUENCE: 2

```
atggagaccg acaccctgct gctgtgggtg ctgctgctgt gggtgccagg cagcaccggc       60
gaggtgcagc tgcagcagag cggacccgag ctgatcaagc caggcgccag cgtgaagatg      120
agctgcaagg ccagcggcta caccttcacc agctacgtga tgcactgggt gaagcagaag      180
ccaggccagg gcctggagtg gatcggctac atcaacccct acaacgacgg caccaagtac      240
aacgagaagt tcaagggcaa ggccaccctg accagcgaca agagcagcag caccgcctac      300
```

```
atggagctga gcagcctgac cagcgaggac agcgccgtgt actactgcgc cagaggcacc        360
tactactacg gcagccgggt gttcgactac tggggccagg gcaccaccct gaccgtgagc        420
tctggcggag gcggctctgg cggaggcggc tctggcggag gcggcagcga catcgtgatg        480
acccaggctg cccccagcat ccccgtgacc caggcagaga gcgtgagcat cagctgccgg        540
agcagcaaga gcctgctgaa cagcaacggc aacacctacc tgtactggtt cctgcagcgg        600
ccaggccaga gcccccagct gctgatctac cggatgagca acctggccag cggcgtgccc        660
gaccggttca gcggcagcgg cagcggcacc gccttcaccc tgcggatcag ccgggtggag        720
gccgaggacg tgggcgtgta ctactgcatg cagcacctgg agtaccccct caccttcgga        780
gccggcacca agctggagct gaagcggtcg atcccaccac caccccagc cccacggcca        840 cctaccectg ccccaaccat cgccagccag ccctgagcc tgcggcctga agcctgcagg        900
cctgccgccg aggagccgt gcacacaagg ggcctggact cgcctgcga catctatatc        960 tgggcccccc tggccgggac atgcggggtg ctgctgctgt ccctggtgat tacactgtat      1020
tgcaaacggg gccggaagaa gctgctgtac atcttcaagc agcccttcat gcggcccgtg      1080
cagaccaccc aggaggagga cggctgcagc tgccggttcc ccgaggaaga ggaaggcggc      1140
tgcgagctgc gggtgaagtt cagccggagc gccgacgccc cagcctacca gcagggccag      1200
aaccagctgt acaacgagct gaacctggga cggcggagg agtacgacgt gctggacaag      1260
cggcggggac gggaccccga gatgggcggc aagcctcgcc ggaagaatcc ccaggagggc      1320
ctgtacaacg agctgcagaa ggacaagatg gccgaggcct acagcgagat cggcatgaag      1380
ggcgagcggc gccggggcaa gggccacgac ggcctgtacc agggcctgag caccgccacc      1440
aaggacacct acgacgccct gcacatgcag gccctgccac cccggtga                   1488
```

<210> SEQ ID NO 3
<211> LENGTH: 1488
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: chimeric antigen receptor

<400> SEQUENCE: 3

```
atggagacag ataccctgct gctgtgggtg ctgctgctgt gggtgcctgg ctccacagga         60
gaggtgcagc tgcagcagtc tggaccagag ctgatcaagc ctggagcatc cgtgaagatg        120
tcttgcaagg ccagcggcta cattcacc agctacgtga tgcactggt gaagcagaag         180 cctggccagg gctggagtg gatcggctat atcaatccat acaacgacgg caccaagtat        240
aatgagaagt ttaagggcaa ggccacactg acctctgata gagctcctc tacagcctac        300 atggagctga gctccctgac ctctgaggac agcgccgtgt actattgcgc cagaggcaca        360
tactattacg gcagccagggt gttcgattac tggggccagg gcaccacact gaccgtgtct        420
agcggaggag gaggctccgg aggaggaggc tctggcggcg gcggcagcga catcgtgatg        480
acacaggcag caccaagcat cccagtgacc cctggcgaga gcgtgtccat ctcttgtcgg        540
tcctctaagt ccctgctgaa ctctaatggc aacacctatc tgtactggtt tctgcagcgg        600
cccggacagt ccccacagct gctgatctat aggatgagca acctggcatc cggagtgcct        660
gatcgcttca gcggctccgg ctctggaaca gcctttaccc tgaggatctc tcgggtggag        720
gcagaggacg tgggcgtgta ttactgcatg cagcacctgg agtaccccTT cacatttggc        780
```

```
gcaggaacca agctggagct gaagcggagc gaccccacca caacccctgc accacggccc      840
cctacaccag cacctaccat cgcatctcag ccactgagcc tgcggcccga ggcctgtagg      900
cctgcagcag gaggagcagt gcacaccagg ggcctggact tcgcctgcga tatctatatc      960
tgggcaccac tggcaggaac atgtggcgtg ctgctgctga gcctggtcat caccctgtat     1020
tgcaagagag gcaggaagaa gctgctgtac atcttcaagc agccttttat gcggccagtg     1080
cagacaaccc aggaggagga tggctgctcc tgtagattcc cagaggagga ggagggagga     1140
tgtgagctgc gcgtgaagtt tagccggtcc gccgacgcac cagcatatca gcagggccag     1200
aatcagctgt acaatgagct gaacctgggc cggagagagg agtacgacgt gctggataag     1260
aggaggggaa gggaccccga gatgggaggc aagccacgga gaaagaatcc ccaggagggc     1320
ctgtataacg agctgcagaa ggataagatg gccgaggcct acagcgagat cggcatgaag     1380
ggagagaggc gccggggcaa gggacacgac ggcctgtatc agggcctgtc cacagccacc     1440
aaggacacct acgatgccct gcacatgcag gccctgccac caaggtga                  1488
```

<210> SEQ ID NO 4
<211> LENGTH: 1875
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: chimeric antigen receptor

<400> SEQUENCE: 4

```
atgggaacaa gcctgctgtg ctggatggct ctgtgcctgc tggggccgga ccacgctgac       60
gcctccgggg gggggggctc tcctgcccct aggcccccta cacctgcacc aaccatcgca      120
tcccagccac tgtctctgcg ccctgaggcc tgccggccag cagcaggagg agcagtgcac      180
acccgcggcc tggacttcgc ctgcgatatc tatatctggg caccactggc aggcacatgt      240
ggcgtgctgc tgctgagcct ggtcatcacc ctgtactgca atcacaggaa ccggagaagg      300
gtgtgcaagt gtccccggcc tgtggtgaga gcagagggaa ggggcagcct gctgacatgt      360
ggcgacgtgg aggagaatcc aggccctatg agacagatac ccctgctgct gtgggtgctg      420
ctgctgtggg tgcccggcag caccggagag gtgcagctgc agcagtccgg accagagctg      480
atcaagcctg agccagcgt gaagatgtcc tgtaaggcct ctggctatac attcaccagc      540
tacgtgatgc actgggtgaa gcagaagcct ggccagggcc tggagtggat cggctatatc      600
aatccataca cgacggcac aaagtataac gagaagttta agggcaaggc cacactgacc      660
tccgataaga gctcctctac agcctacatg gagctgagct ccctgacctc tgaggacagc      720
gccgtgtact attgcgccag aggcacatac tattacggct ctagggtgtt cgattactgg      780
ggccagggca ccacactgac cgtgtctagc ggaggaggag gcagcggagg aggaggctcc      840
ggcggcggcg gctctgacat cgtgatgaca caggcagcac catccatccc agtgaccccc      900
ggcgagagcg tgtccatctc ttgtcggtcc tctaagagcc tgctgaactc caatggcaac      960
acctatctgt actggttcct gcagcggccc ggacagagcc cacagctgct gatctatagg     1020
atgtctaatc tggcaagcgg cgtgcccgat cgcttcagcg gctccggctc tggcacagcc     1080
tttaccctga ggatctcccg cgtggaggca gaggacgtgg gcgtgtatta ctgcatgcag     1140
cacctggagt accccttcac atttggcgca ggcaccaagc tggagctgaa gcggagcgac     1200
cccaccacaa cccctgcacc acggccaccc acaccagcac ctactattgc atcccagcca     1260
```

| | |
|---|---|
| ctgagcctgc ggcccgaggc ctgtaggcct gccgccggcg gcgcagtgca cacccggggc | 1320 |
| ctggactttg cctgcgatat ctacatctgg gcacctctgg ccggcacatg cggcgtgctg | 1380 |
| ttactgagcc tggtcatcac cctgtattgc aagcggggca gaaagaagct gctgtacatc | 1440 |
| ttcaagcagc ctttatgcg gccagtgcag acaacccagg aggaggatgg ctgctcctgt | 1500 |
| agattcccag aggaggagga gggaggatgt gagctgcgcg tgaagtttag ccggtccgcc | 1560 |
| gacgcaccag catatcagca gggccagaac cagctgtaca atgagctgaa cctgggccgg | 1620 |
| agagaggagt atgacgtgct ggataagaga cggggccggg accccgagat gggaggcaag | 1680 |
| ccacgccgga agaatcccca ggagggcctg tataacgagc tgcagaagga taagatggcc | 1740 |
| gaggcctaca gcgagatcgg catgaaggga gagagaaggc gcggcaaggg acacgacggc | 1800 |
| ctgtaccagg gcctgagcac agcaacaaaa gacacctacg acgcactgca catgcaggct | 1860 |
| ctgccccctc ggtaa | 1875 |

<210> SEQ ID NO 5
<211> LENGTH: 1941
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: chimeric antigen receptor

<400> SEQUENCE: 5

| | |
|---|---|
| atgggaacct ctctgctgtg ctggatggct ctgtgcctgc tggggccgga tcacgctgac | 60 |
| gcaagtggcg ggggggggtc cgaactgccc acacagggca ccttctccaa cgtgagcacc | 120 |
| aacgtgagct ccggcggagg aggcagccct gcaccaaggc cccctacacc agcacctacc | 180 |
| atcgcatctc agccactgag cctgcgcccc gaggcctgcc ggcctgcagc aggcggcgcc | 240 |
| gtgcacaccc gcgcctgga ctttgcctgc gatatctata tctgggcacc tctggcaggc | 300 |
| acatgtggcg tgctgctgct gagcctggtc atccctgt actgcaatca caggaaccgg | 360 |
| agaagggtgt gcaagtgtcc acggcccgtg gtgagagcag agggaagggg ctccctgctg | 420 |
| acatgtggcg acgtggagga gaatcctggc ccaatggaga cagataccct gctgctgtgg | 480 |
| gtgctgctgc tgtgggtgcc cggctccacc ggagaggtgc agctgcagca gtctggacca | 540 |
| gagctgatca agccaggagc atccgtgaag atgtcttgta aggccagcgg ctatacattc | 600 |
| accagctacg tgatgcactg ggtgaagcag aagccaggac agggcctgga gtggatcggc | 660 |
| tatatcaatc cttacaacga cggcaccaag tataacgaga gtttaaggg caaggccaca | 720 |
| ctgacctctg ataagtctag ctccacagcc tacatggagc tgtctagcct gaccagcgag | 780 |
| gactccgccg tgtactattg cgccagaggc acatactatt acggcagcag ggtgttcgat | 840 |
| tactggggcc agggcaccac actgaccgtg tcctctggag aggaggctc cggaggagga | 900 |
| ggctctggcg gcggcggcag cgacatcgtg atgacacagg cagcaccttc catcccagtg | 960 |
| accccaggcg agtctgtgag catctcctgt cggagctcca gtccctgct gaactctaat | 1020 |
| ggcaacacct atctgtactg gtttctgcag cggcccggac agtccccaca gctgctgatc | 1080 |
| tataggatga gcaatctggc ctccggcgtg ccagatcgct tctctggcag cggctccggc | 1140 |
| acagccttta ccctgaggat ctctcgcgtg gaggcagagg acgtgggcgt gtattactgc | 1200 |
| atgcagcacc tggagtaccc attcacattt ggcgcaggca ccaagctgga gctgaagcgg | 1260 |
| agcgacccca ccacaacccc agcacctcgg ccacccacac cagcacccac catcgcatct | 1320 |

```
cagcctctga gcctgcggcc cgaggcctgt aggcccgcag caggaggagc agtgcacacc    1380
cggggcctgg acttcgcctg cgatatctac atctgggcac cactggccgg cacatgcggc    1440
gtgctgttac tgagcctggt catcaccctg tattgcaagc ggggcagaaa gaagctgctg    1500
tacatcttca agcagccctt tatgcggcct gtgcagacaa cccaggagga ggatggctgc    1560
tcctgtagat ccctgaggag ggaggaggga ggatgtgagc tgcgcgtgaa gttttctcgg    1620
agcgccgacg caccagcata tcagcaggga cagaaccagc tgtacaatga gctgaacctg    1680
ggccggagag aggagtatga cgtgctggat aagagacggg gccgggaccc cgagatggga    1740
ggcaagcctc gccggaagaa tccacaggag ggcctgtata cgagctgca gaaggataag    1800 atggccgagg cctacagcga gatcggcatg aagggagaga aaggcgcgg caagggacac    1860 gacggcctgt accagggcct gagcacagca acaaaagaca cctacgacgc actgcacatg    1920
caggctctgc caccaagatg a                                              1941
```

<210> SEQ ID NO 6
<211> LENGTH: 2019
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: chimeric antigen receptor

<400> SEQUENCE: 6

```
atggggacct cactgctgtg ctggatggct ctgtgcctgc tggggggcga ccacgctgac     60
gcctgctctg ggggggggg gggctcatgc tccggaggag gaggctctga gctgccaacc    120
cagggcacat tctccaacgt gagcaccaac gtgtctcctg ccaagccaac cacaaccgca    180
tgcagcggcg aggaggagg cagctgttcc ggcggcggcg gcagccctgc cccaaggccc    240
cctaccccag cacctacaat cgcatctcag cctctgagcc tgcgcccaga ggcctgtcgg    300
cccgcagcag gaggagcagt gcacacccgc ggcctggact ttgcctgcga tatctatatc    360
tgggcaccac tggcaggcac ctgtggcgtg ctgctgctga gcctggtcat caccctgtac    420
tgcaatcaca ggaaccggag aagggtgtgc aagtgtccac ggcccgtggt gagagcagag    480
ggaaggggct ctctgctgac ctgtggcgac gtggaggaga tcctggccc tatggagaca    540 gatacactgc tgctgtgggt gctgctgctg tgggtgcccg gcagcacagg agaggtgcag    600
ctgcagcagt ccggacctga gctgatcaag ccaggcgcct ccgtgaagat gtcttgcaag    660
gccagcggct ataccttcac aagctacgtg atgcactggg tgaagcagaa gccaggccag    720
ggcctggagt ggatcggcta tatcaatccc tacaacgacg gcaccaagta taacgagaag    780
tttaagggca aggccaccct gacaagcgat aagagctcct ctaccgccta catggagctg    840
agctccctga aagcgagga ctccgccgtg tactattgcg ccagaggcac ctactattac    900
ggctccaggg tgttcgatta ctggggccag ggcacaaccc tgacagtgtc tagcggagga    960
ggaggcagcg gaggaggagg ctccggcggc ggcggctctg acatcgtgat gacccaggca   1020
gcaccatcca tccctgtgac accaggcgag tctgtgagca tcctctgtcg gtcctctaag   1080
tccctgctga actctaatgg caacacctat ctgtactggt ttctgcagcg gcccggacag   1140
tctcctcagc tgctgatcta taggatgagc aatctggcct ccggcgtgcc tgatcgcttc   1200
tctggcagcg gctccggcac cgcctttaca ctgaggatca gccgcgtgga ggcagaggac   1260
gtgggcgtgt attactgcat gcagcacctg gagtacccct tcacctttgg cgccggcaca   1320
```

| | |
|---|---|
| aagctggagc tgaagcggag cgaccccaca accacaccag cacctcggcc acccacccca | 1380 |
| gcaccaacaa tcgcatctca gccactgagc ctgcggcccg aggcctgtag gccagccgcc | 1440 |
| ggcggcgcag tgcacacccg gggcctggac ttcgcctgcg atatctacat ctgggcccct | 1500 |
| ctggccggca cctgcggcgt gctgttactg agcctggtca tcaccctgta ttgcaagcgg | 1560 |
| ggcagaaaga agctgctgta catcttcaag cagcccttca tgcggcccgt gcagaccaca | 1620 |
| caggaggagg atggctgctc ctgtagattc ccagaggagg aggagggagg atgtgagctg | 1680 |
| cgcgtgaagt tttctcggag cgccgacgca cctgcatatc agcagggaca gaaccagctg | 1740 |
| tacaatgagc tgaacctggg ccggagagag gagtatgacg tgctggataa gagacggggc | 1800 |
| cgggaccccg agatgggagg caagcccccgc cggaagaatc ctcaggaggg cctgtataac | 1860 |
| gagctgcaga aggataagat ggccgaggcc tacagcgaga tcggcatgaa gggagagaga | 1920 |
| aggcgcggca agggccacga cggcctgtac cagggcctgt ccacagcaac aaaggatact | 1980 |
| tatgacgctc tgcacatgca ggctctgccc cctcggtga | 2019 |

<210> SEQ ID NO 7
<211> LENGTH: 2061
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: chimeric antigen receptor

<400> SEQUENCE: 7

| | |
|---|---|
| atgggaacca gcctgctgtg ctggatggca ctgtgcctgc tgggagcaga ccacgccgat | 60 |
| gccgaactgc ctactcaggg gacattctct aatgtgagca ccaacgtgag ctctggagga | 120 |
| ggaggctccg agctgccaac ccagggcaca ttctctaatg tgagcacaaa cgtgtctccc | 180 |
| gccaagccta ccacaaccgc cgaactgcct acccagggca catttccaa cgtgtctacc | 240 |
| aacgtgtcta gcggaggagg aggctccccc gcacctaggc cccctacccc agcaccaaca | 300 |
| atcgcaagcc agcctctgtc cctgcgccca gaggcatgca ggccagcagc aggaggagca | 360 |
| gtgcacaccc gcggcctgga cttttgcctgc gatatctata tctgggcacc actggcagga | 420 |
| acctgtggcg tgctgctgct gtctctggtc atcaccctgt actgcaatca cagaaaccgg | 480 |
| agaagggtgt gcaagtgtcc tcggccagtg gtgagagcag agggaagggg cagcctgctg | 540 |
| acctgtggcg acgtggagga gaatcccggc cctatggaga cagatacact gctgctgtgg | 600 |
| gtgctgctgc tgtgggtgcc aggctctaca ggagaggtgc agctgcagca gagcggacct | 660 |
| gagctgatca gccaggcgc ctctgtgaag atgagctgca aggcctccgg ctataccttc | 720 |
| acaagctacg tgatgcactg ggtgaagcag aagccaggcc agggcctgga gtggatcggc | 780 |
| tatatcaatc cctacaacga cggcaccaag tataacgaga gtttaaggg caaggccacc | 840 |
| ctgacatccg ataagagctc ctctaccgcc tacatggagc tgagctccct gacatccgag | 900 |
| gactctgccg tgtactattg cgccagaggc acctactatt acggctctag ggtgttcgat | 960 |
| tactggggcc agggcacaac cctgacagtg tctagcggag gaggaggctc tggaggagga | 1020 |
| ggcagcggcg gcggaggctc cgacatcgtg atgacccagg cagcaccatc catcccagtg | 1080 |
| acacctggcg agagcgtgtc catctcttgt aggtcctcta gtctctgct gaacagcaat | 1140 |
| ggcaacacct atctgtactg gtttctgcag cggcccggac agagccctca gctgctgatc | 1200 |
| tataggatgt ccaatctggc ctctggagtg cctgatcgct tcagcggctc cggctctgga | 1260 |

-continued

```
accgccttta cactgaggat ctcccgcgtg gaggcagagg acgtgggcgt gtattactgc   1320
atgcagcacc tggagtaccc tttcaccttt ggcgccggca caaagctgga gctgaagcgg   1380
agcgacccca caaccacacc agcaccccgg ccaccaaccc ctgcccctac aatcgcaagc   1440
cagccactgt ccctgcggcc cgaggcctgt agacctgccg ccggcggcgc cgtccatacc   1500
cgcggcctgg atttcgcctg cgatatctac atttgggccc ctctggccgg cacttgcggc   1560
gtgctgctgc tgagcctggt catcaccctg tattgcaagc ggggcagaaa gaagctgctg   1620
tacatcttca agcagccctt catgcggccc gtgcagacca cacaggagga ggatggctgc   1680
tcctgtagat tcccagagga ggaggaggga ggatgtgagc tgcgcgtgaa gtttagccgg   1740
tccgccgacg cacctgcata tcagcagggc cagaaccagc tgtacaatga gctgaacctg   1800
ggccggagag aggagtacga cgtgctggat aagagaaggg gacgggaccc cgagatggga   1860
ggcaagcccc gccggaagaa tcctcaggag ggcctgtata cgagctgca aaggataag   1920 atggccgagg cctacagcga gatcggcatg aagggagaga gaaggcgcgg caagggacac   1980
gacggcctgt atcagggcct gtccaccgcc acaaaggaca cctacgatgc cctgcacatg   2040
caggccctgc ctccaagatg a                                             2061
```

<210> SEQ ID NO 8
<211> LENGTH: 672
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: chimeric antigen receptor

<400> SEQUENCE: 8

```
Met Leu Thr Ser Leu Leu Cys Trp Met Ala Leu Cys Leu Leu Gly Ala
1               5                   10                  15

Asp His Ala Asp Ala Cys Pro Tyr Ser Asn Pro Ser Leu Cys Ser Gly
            20                  25                  30

Gly Gly Gly Ser Glu Leu Pro Thr Gln Gly Thr Phe Ser Asn Val Ser
        35                  40                  45

Thr Asn Val Ser Pro Ala Lys Pro Thr Thr Thr Ala Cys Pro Tyr Ser
    50                  55                  60

Asn Pro Ser Leu Cys Ser Gly Gly Gly Ser Pro Ala Pro Arg Pro
65                  70                  75                  80

Pro Thr Pro Ala Pro Thr Ile Ala Ser Gln Pro Leu Ser Leu Arg Pro
                85                  90                  95

Glu Ala Cys Arg Pro Ala Ala Gly Gly Ala Val His Thr Arg Gly Leu
            100                 105                 110

Asp Phe Ala Cys Asp Ile Tyr Ile Trp Ala Pro Leu Ala Gly Thr Cys
        115                 120                 125

Gly Val Leu Leu Leu Ser Leu Val Ile Thr Leu Tyr Cys Asn His Arg
    130                 135                 140

Asn Arg Arg Arg Val Cys Lys Cys Pro Arg Pro Val Val Arg Ala Glu
145                 150                 155                 160

Gly Arg Gly Ser Leu Leu Thr Cys Gly Asp Val Glu Glu Asn Pro Gly
                165                 170                 175

Pro Met Glu Thr Asp Thr Leu Leu Leu Trp Val Leu Leu Leu Trp Val
            180                 185                 190

Pro Gly Ser Thr Gly Glu Val Gln Leu Gln Gln Ser Gly Pro Glu Leu
```

```
            195                 200                 205
Ile Lys Pro Gly Ala Ser Val Lys Met Ser Cys Lys Ala Ser Gly Tyr
210                 215                 220
Thr Phe Thr Ser Tyr Val Met His Trp Val Lys Gln Lys Pro Gly Gln
225                 230                 235                 240
Gly Leu Glu Trp Ile Gly Tyr Ile Asn Pro Tyr Asn Asp Gly Thr Lys
                245                 250                 255
Tyr Asn Glu Lys Phe Lys Gly Lys Ala Thr Leu Thr Ser Asp Lys Ser
            260                 265                 270
Ser Ser Thr Ala Tyr Met Glu Leu Ser Ser Leu Thr Ser Glu Asp Ser
        275                 280                 285
Ala Val Tyr Tyr Cys Ala Arg Gly Thr Tyr Tyr Gly Ser Arg Val
290                 295                 300
Phe Asp Tyr Trp Gly Gln Gly Thr Thr Leu Thr Val Ser Ser Gly Gly
305                 310                 315                 320
Gly Gly Ser Gly Gly Gly Ser Gly Gly Gly Ser Asp Ile Val
                325                 330                 335
Met Thr Gln Ala Ala Pro Ser Ile Pro Val Thr Pro Gly Glu Ser Val
            340                 345                 350
Ser Ile Ser Cys Arg Ser Ser Lys Ser Leu Leu Asn Ser Asn Gly Asn
        355                 360                 365
Thr Tyr Leu Tyr Trp Phe Leu Gln Arg Pro Gly Gln Ser Pro Gln Leu
370                 375                 380
Leu Ile Tyr Arg Met Ser Asn Leu Ala Ser Gly Val Pro Asp Arg Phe
385                 390                 395                 400
Ser Gly Ser Gly Ser Gly Thr Ala Phe Thr Leu Arg Ile Ser Arg Val
                405                 410                 415
Glu Ala Glu Asp Val Gly Val Tyr Tyr Cys Met Gln His Leu Glu Tyr
            420                 425                 430
Pro Phe Thr Phe Gly Ala Gly Thr Lys Leu Glu Leu Lys Arg Ser Asp
        435                 440                 445
Pro Thr Thr Thr Pro Ala Pro Arg Pro Pro Thr Pro Ala Pro Thr Ile
450                 455                 460
Ala Ser Gln Pro Leu Ser Leu Arg Pro Glu Ala Cys Arg Pro Ala Ala
465                 470                 475                 480
Gly Gly Ala Val His Thr Arg Gly Leu Asp Phe Ala Cys Asp Ile Tyr
                485                 490                 495
Ile Trp Ala Pro Leu Ala Gly Thr Cys Gly Val Leu Leu Leu Ser Leu
            500                 505                 510
Val Ile Thr Leu Tyr Cys Lys Arg Gly Arg Lys Lys Leu Leu Tyr Ile
        515                 520                 525
Phe Lys Gln Pro Phe Met Arg Pro Val Gln Thr Thr Gln Glu Glu Asp
530                 535                 540
Gly Cys Ser Cys Arg Phe Pro Glu Glu Glu Glu Gly Gly Cys Glu Leu
545                 550                 555                 560
Arg Val Lys Phe Ser Arg Ser Ala Asp Ala Pro Ala Tyr Gln Gln Gly
                565                 570                 575
Gln Asn Gln Leu Tyr Asn Glu Leu Asn Leu Gly Arg Arg Glu Glu Tyr
            580                 585                 590
Asp Val Leu Asp Lys Arg Arg Gly Arg Asp Pro Glu Met Gly Gly Lys
        595                 600                 605
Pro Arg Arg Lys Asn Pro Gln Glu Gly Leu Tyr Asn Glu Leu Gln Lys
610                 615                 620
```

```
Asp Lys Met Ala Glu Ala Tyr Ser Glu Ile Gly Met Lys Gly Glu Arg
625                 630                 635                 640

Arg Arg Gly Lys Gly His Asp Gly Leu Tyr Gln Gly Leu Ser Thr Ala
            645                 650                 655

Thr Lys Asp Thr Tyr Asp Ala Leu His Met Gln Ala Leu Pro Pro Arg
        660                 665                 670

<210> SEQ ID NO 9
<211> LENGTH: 495
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: chimeric antigen receptor

<400> SEQUENCE: 9

Met Glu Thr Asp Thr Leu Leu Leu Trp Val Leu Leu Leu Trp Val Pro
1               5                   10                  15

Gly Ser Thr Gly Glu Val Gln Leu Gln Gln Ser Gly Pro Glu Leu Ile
            20                  25                  30

Lys Pro Gly Ala Ser Val Lys Met Ser Cys Lys Ala Ser Gly Tyr Thr
        35                  40                  45

Phe Thr Ser Tyr Val Met His Trp Val Lys Gln Lys Pro Gly Gln Gly
    50                  55                  60

Leu Glu Trp Ile Gly Tyr Ile Asn Pro Tyr Asn Asp Gly Thr Lys Tyr
65                  70                  75                  80

Asn Glu Lys Phe Lys Gly Lys Ala Thr Leu Thr Ser Asp Lys Ser Ser
                85                  90                  95

Ser Thr Ala Tyr Met Glu Leu Ser Ser Leu Thr Ser Glu Asp Ser Ala
            100                 105                 110

Val Tyr Tyr Cys Ala Arg Gly Thr Tyr Tyr Gly Ser Arg Val Phe
        115                 120                 125

Asp Tyr Trp Gly Gln Gly Thr Thr Leu Thr Val Ser Ser Gly Gly Gly
    130                 135                 140

Gly Ser Gly Gly Gly Gly Ser Gly Gly Gly Gly Ser Asp Ile Val Met
145                 150                 155                 160

Thr Gln Ala Ala Pro Ser Ile Pro Val Thr Pro Gly Glu Ser Val Ser
                165                 170                 175

Ile Ser Cys Arg Ser Ser Lys Ser Leu Leu Asn Ser Asn Gly Asn Thr
            180                 185                 190

Tyr Leu Tyr Trp Phe Leu Gln Arg Pro Gly Gln Ser Pro Gln Leu Leu
        195                 200                 205

Ile Tyr Arg Met Ser Asn Leu Ala Ser Gly Val Pro Asp Arg Phe Ser
    210                 215                 220

Gly Ser Gly Ser Gly Thr Ala Phe Thr Leu Arg Ile Ser Arg Val Glu
225                 230                 235                 240

Ala Glu Asp Val Gly Val Tyr Tyr Cys Met Gln His Leu Glu Tyr Pro
                245                 250                 255

Phe Thr Phe Gly Ala Gly Thr Lys Leu Glu Leu Lys Arg Ser Asp Pro
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300
```

```
Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
            325                 330                 335

Ile Thr Leu Tyr Cys Lys Arg Gly Arg Lys Lys Leu Leu Tyr Ile Phe
        340                 345                 350

Lys Gln Pro Phe Met Arg Pro Val Gln Thr Thr Gln Glu Glu Asp Gly
    355                 360                 365

Cys Ser Cys Arg Phe Pro Glu Glu Glu Glu Gly Gly Cys Glu Leu Arg
370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 10
<211> LENGTH: 495
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: chimeric antigen receptor

<400> SEQUENCE: 10

Met Glu Thr Asp Thr Leu Leu Leu Trp Val Leu Leu Leu Trp Val Pro
1               5                   10                  15

Gly Ser Thr Gly Glu Val Gln Leu Gln Gln Ser Gly Pro Glu Leu Ile
            20                  25                  30

Lys Pro Gly Ala Ser Val Lys Met Ser Cys Lys Ala Ser Gly Tyr Thr
        35                  40                  45

Phe Thr Ser Tyr Val Met His Trp Val Lys Gln Lys Pro Gly Gln Gly
    50                  55                  60

Leu Glu Trp Ile Gly Tyr Ile Asn Pro Tyr Asn Asp Gly Thr Lys Tyr
65                  70                  75                  80

Asn Glu Lys Phe Lys Gly Lys Ala Thr Leu Thr Ser Asp Lys Ser Ser
                85                  90                  95

Ser Thr Ala Tyr Met Glu Leu Ser Ser Leu Thr Ser Glu Asp Ser Ala
            100                 105                 110

Val Tyr Tyr Cys Ala Arg Gly Thr Tyr Tyr Gly Ser Arg Val Phe
        115                 120                 125

Asp Tyr Trp Gly Gln Gly Thr Thr Leu Thr Val Ser Ser Gly Gly Gly
    130                 135                 140

Gly Ser Gly Gly Gly Gly Ser Gly Gly Gly Gly Ser Asp Ile Val Met
145                 150                 155                 160
```

Thr Gln Ala Ala Pro Ser Ile Pro Val Thr Pro Gly Glu Ser Val Ser
            165                 170                 175

Ile Ser Cys Arg Ser Ser Lys Ser Leu Leu Asn Ser Asn Gly Asn Thr
            180                 185                 190

Tyr Leu Tyr Trp Phe Leu Gln Arg Pro Gly Gln Ser Pro Gln Leu Leu
            195                 200                 205

Ile Tyr Arg Met Ser Asn Leu Ala Ser Gly Val Pro Asp Arg Phe Ser
            210                 215                 220

Gly Ser Gly Ser Gly Thr Ala Phe Thr Leu Arg Ile Ser Arg Val Glu
225                 230                 235                 240

Ala Glu Asp Val Gly Val Tyr Tyr Cys Met Gln His Leu Glu Tyr Pro
            245                 250                 255

Phe Thr Phe Gly Ala Gly Thr Lys Leu Glu Leu Lys Arg Ser Asp Pro
            260                 265                 270

Thr Thr Thr Pro Ala Pro Arg Pro Pro Thr Pro Ala Pro Thr Ile Ala
            275                 280                 285

Ser Gln Pro Leu Ser Leu Arg Pro Glu Ala Cys Arg Pro Ala Ala Gly
            290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
            325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
            355                 360                 365

Cys Ser Cys Arg Phe Pro Glu Glu Glu Glu Gly Gly Cys Glu Leu Arg
            370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
            405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
            435                 440                 445

Lys Met Ala Glu Ala Tyr Ser Glu Ile Gly Met Lys Gly Glu Arg Arg
450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
            485                 490                 495

<210> SEQ ID NO 11
<211> LENGTH: 624
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: chimeric antigen receptor

<400> SEQUENCE: 11

Met Gly Thr Ser Leu Leu Cys Trp Met Ala Leu Cys Leu Leu Gly Ala
1               5                   10                  15

```
Asp His Ala Asp Ala Ser Gly Gly Gly Ser Pro Ala Pro Arg Pro
            20                  25                  30

Pro Thr Pro Ala Pro Thr Ile Ala Ser Gln Pro Leu Ser Leu Arg Pro
                35                  40                  45

Glu Ala Cys Arg Pro Ala Ala Gly Gly Ala Val His Thr Arg Gly Leu
 50                  55                  60

Asp Phe Ala Cys Asp Ile Tyr Ile Trp Ala Pro Leu Ala Gly Thr Cys
 65                  70                  75                  80

Gly Val Leu Leu Leu Ser Leu Val Ile Thr Leu Tyr Cys Asn His Arg
                85                  90                  95

Asn Arg Arg Arg Val Cys Lys Cys Pro Arg Pro Val Val Arg Ala Glu
                100                 105                 110

Gly Arg Gly Ser Leu Leu Thr Cys Gly Asp Val Glu Glu Asn Pro Gly
                115                 120                 125

Pro Met Glu Thr Asp Thr Leu Leu Leu Trp Val Leu Leu Leu Trp Val
        130                 135                 140

Pro Gly Ser Thr Gly Glu Val Gln Leu Gln Gln Ser Gly Pro Glu Leu
145                 150                 155                 160

Ile Lys Pro Gly Ala Ser Val Lys Met Ser Cys Lys Ala Ser Gly Tyr
                165                 170                 175

Thr Phe Thr Ser Tyr Val Met His Trp Val Lys Gln Lys Pro Gly Gln
            180                 185                 190

Gly Leu Glu Trp Ile Gly Tyr Ile Asn Pro Tyr Asn Asp Gly Thr Lys
            195                 200                 205

Tyr Asn Glu Lys Phe Lys Gly Lys Ala Thr Leu Thr Ser Asp Lys Ser
        210                 215                 220

Ser Ser Thr Ala Tyr Met Glu Leu Ser Ser Leu Thr Ser Glu Asp Ser
225                 230                 235                 240

Ala Val Tyr Tyr Cys Ala Arg Gly Thr Tyr Tyr Gly Ser Arg Val
                245                 250                 255

Phe Asp Tyr Trp Gly Gln Gly Thr Thr Leu Thr Val Ser Ser Gly Gly
            260                 265                 270

Gly Gly Ser Gly Gly Gly Gly Ser Gly Gly Gly Gly Ser Asp Ile Val
        275                 280                 285

Met Thr Gln Ala Ala Pro Ser Ile Pro Val Thr Pro Gly Glu Ser Val
        290                 295                 300

Ser Ile Ser Cys Arg Ser Ser Lys Ser Leu Leu Asn Ser Asn Gly Asn
305                 310                 315                 320

Thr Tyr Leu Tyr Trp Phe Leu Gln Arg Pro Gly Gln Ser Pro Gln Leu
                325                 330                 335

Leu Ile Tyr Arg Met Ser Asn Leu Ala Ser Gly Val Pro Asp Arg Phe
            340                 345                 350

Ser Gly Ser Gly Ser Gly Thr Ala Phe Thr Leu Arg Ile Ser Arg Val
            355                 360                 365

Glu Ala Glu Asp Val Gly Val Tyr Tyr Cys Met Gln His Leu Glu Tyr
        370                 375                 380

Pro Phe Thr Phe Gly Ala Gly Thr Lys Leu Glu Leu Lys Arg Ser Asp
385                 390                 395                 400

Pro Thr Thr Thr Pro Ala Pro Arg Pro Pro Thr Pro Ala Pro Thr Ile
                405                 410                 415

Ala Ser Gln Pro Leu Ser Leu Arg Pro Glu Ala Cys Arg Pro Ala Ala
            420                 425                 430
```

```
Gly Gly Ala Val His Thr Arg Gly Leu Asp Phe Ala Cys Asp Ile Tyr
            435                 440                 445
Ile Trp Ala Pro Leu Ala Gly Thr Cys Gly Val Leu Leu Leu Ser Leu
450                 455                 460
Val Ile Thr Leu Tyr Cys Lys Arg Gly Arg Lys Lys Leu Leu Tyr Ile
465                 470                 475                 480
Phe Lys Gln Pro Phe Met Arg Pro Val Gln Thr Thr Gln Glu Glu Asp
                485                 490                 495
Gly Cys Ser Cys Arg Phe Pro Glu Glu Glu Glu Gly Gly Cys Glu Leu
            500                 505                 510
Arg Val Lys Phe Ser Arg Ser Ala Asp Ala Pro Ala Tyr Gln Gln Gly
            515                 520                 525
Gln Asn Gln Leu Tyr Asn Glu Leu Asn Leu Gly Arg Arg Glu Glu Tyr
530                 535                 540
Asp Val Leu Asp Lys Arg Arg Gly Arg Asp Pro Glu Met Gly Gly Lys
545                 550                 555                 560
Pro Arg Arg Lys Asn Pro Gln Glu Gly Leu Tyr Asn Glu Leu Gln Lys
                565                 570                 575
Asp Lys Met Ala Glu Ala Tyr Ser Glu Ile Gly Met Lys Gly Glu Arg
            580                 585                 590
Arg Arg Gly Lys Gly His Asp Gly Leu Tyr Gln Gly Leu Ser Thr Ala
            595                 600                 605
Thr Lys Asp Thr Tyr Asp Ala Leu His Met Gln Ala Leu Pro Pro Arg
            610                 615                 620

<210> SEQ ID NO 12
<211> LENGTH: 646
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: chimeric antigen receptor

<400> SEQUENCE: 12

Met Gly Thr Ser Leu Leu Cys Trp Met Ala Leu Cys Leu Leu Gly Ala
1               5                   10                  15
Asp His Ala Asp Ala Ser Gly Gly Gly Gly Ser Glu Leu Pro Thr Gln
            20                  25                  30
Gly Thr Phe Ser Asn Val Ser Thr Asn Val Ser Ser Gly Gly Gly Gly
            35                  40                  45
Ser Pro Ala Pro Arg Pro Pro Thr Pro Ala Pro Thr Ile Ala Ser Gln
50                  55                  60
Pro Leu Ser Leu Arg Pro Glu Ala Cys Arg Pro Ala Ala Gly Gly Ala
65                  70                  75                  80
Val His Thr Arg Gly Leu Asp Phe Ala Cys Asp Ile Tyr Ile Trp Ala
                85                  90                  95
Pro Leu Ala Gly Thr Cys Gly Val Leu Leu Leu Ser Leu Val Ile Thr
            100                 105                 110
Leu Tyr Cys Asn His Arg Asn Arg Arg Arg Val Cys Lys Cys Pro Arg
            115                 120                 125
Pro Val Val Arg Ala Glu Gly Arg Gly Ser Leu Leu Thr Cys Gly Asp
            130                 135                 140
Val Glu Glu Asn Pro Gly Pro Met Glu Thr Asp Thr Leu Leu Leu Trp
145                 150                 155                 160
```

Val Leu Leu Leu Trp Val Pro Gly Ser Thr Gly Glu Val Gln Leu Gln
                165                 170                 175

Gln Ser Gly Pro Glu Leu Ile Lys Pro Gly Ala Ser Val Lys Met Ser
            180                 185                 190

Cys Lys Ala Ser Gly Tyr Thr Phe Thr Ser Tyr Val Met His Trp Val
            195                 200                 205

Lys Gln Lys Pro Gly Gln Gly Leu Glu Trp Ile Gly Tyr Ile Asn Pro
            210                 215                 220

Tyr Asn Asp Gly Thr Lys Tyr Asn Glu Lys Phe Lys Gly Lys Ala Thr
225                 230                 235                 240

Leu Thr Ser Asp Lys Ser Ser Thr Ala Tyr Met Glu Leu Ser Ser
                245                 250                 255

Leu Thr Ser Glu Asp Ser Ala Val Tyr Tyr Cys Ala Arg Gly Thr Tyr
            260                 265                 270

Tyr Tyr Gly Ser Arg Val Phe Asp Tyr Trp Gly Gln Gly Thr Thr Leu
            275                 280                 285

Thr Val Ser Ser Gly Gly Gly Ser Gly Gly Gly Ser Gly Gly
            290                 295                 300

Gly Gly Ser Asp Ile Val Met Thr Gln Ala Ala Pro Ser Ile Pro Val
305                 310                 315                 320

Thr Pro Gly Glu Ser Val Ser Ile Ser Cys Arg Ser Ser Lys Ser Leu
                325                 330                 335

Leu Asn Ser Asn Gly Asn Thr Tyr Leu Tyr Trp Phe Leu Gln Arg Pro
            340                 345                 350

Gly Gln Ser Pro Gln Leu Leu Ile Tyr Arg Met Ser Asn Leu Ala Ser
            355                 360                 365

Gly Val Pro Asp Arg Phe Ser Gly Ser Gly Ser Gly Thr Ala Phe Thr
            370                 375                 380

Leu Arg Ile Ser Arg Val Glu Ala Glu Asp Val Gly Val Tyr Tyr Cys
385                 390                 395                 400

Met Gln His Leu Glu Tyr Pro Phe Thr Phe Gly Ala Gly Thr Lys Leu
                405                 410                 415

Glu Leu Lys Arg Ser Asp Pro Thr Thr Thr Pro Ala Pro Arg Pro Pro
            420                 425                 430

Thr Pro Ala Pro Thr Ile Ala Ser Gln Pro Leu Ser Leu Arg Pro Glu
            435                 440                 445

Ala Cys Arg Pro Ala Ala Gly Gly Ala Val His Thr Arg Gly Leu Asp
            450                 455                 460

Phe Ala Cys Asp Ile Tyr Ile Trp Ala Pro Leu Ala Gly Thr Cys Gly
465                 470                 475                 480

Val Leu Leu Leu Ser Leu Val Ile Thr Leu Tyr Cys Lys Arg Gly Arg
                485                 490                 495

Lys Lys Leu Leu Tyr Ile Phe Lys Gln Pro Phe Met Arg Pro Val Gln
            500                 505                 510

Thr Thr Gln Glu Glu Asp Gly Cys Ser Cys Arg Phe Pro Glu Glu Glu
            515                 520                 525

Glu Gly Gly Cys Glu Leu Arg Val Lys Phe Ser Arg Ser Ala Asp Ala
            530                 535                 540

Pro Ala Tyr Gln Gln Gly Gln Asn Gln Leu Tyr Asn Glu Leu Asn Leu
545                 550                 555                 560

Gly Arg Arg Glu Glu Tyr Asp Val Leu Asp Lys Arg Gly Arg Asp
                565                 570                 575

Pro Glu Met Gly Gly Lys Pro Arg Arg Lys Asn Pro Gln Glu Gly Leu

```
                  580                 585                 590
Tyr Asn Glu Leu Gln Lys Asp Lys Met Ala Glu Ala Tyr Ser Glu Ile
            595                 600                 605

Gly Met Lys Gly Glu Arg Arg Arg Gly Lys Gly His Asp Gly Leu Tyr
        610                 615                 620

Gln Gly Leu Ser Thr Ala Thr Lys Asp Thr Tyr Asp Ala Leu His Met
625                 630                 635                 640

Gln Ala Leu Pro Pro Arg
                645

<210> SEQ ID NO 13
<211> LENGTH: 672
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: chimeric antigen receptor

<400> SEQUENCE: 13

Met Gly Thr Ser Leu Leu Cys Trp Met Ala Leu Cys Leu Leu Gly Ala
1               5                   10                  15

Asp His Ala Asp Ala Cys Ser Gly Gly Gly Gly Ser Cys Ser Gly
            20                  25                  30

Gly Gly Gly Ser Glu Leu Pro Thr Gln Gly Thr Phe Ser Asn Val Ser
        35                  40                  45

Thr Asn Val Ser Pro Ala Lys Pro Thr Thr Thr Ala Cys Ser Gly Gly
    50                  55                  60

Gly Gly Gly Ser Cys Ser Gly Gly Gly Ser Pro Ala Pro Arg Pro
65                  70                  75                  80

Pro Thr Pro Ala Pro Thr Ile Ala Ser Gln Pro Leu Ser Leu Arg Pro
            85                  90                  95

Glu Ala Cys Arg Pro Ala Ala Gly Ala Val His Thr Arg Gly Leu
            100                 105                 110

Asp Phe Ala Cys Asp Ile Tyr Ile Trp Ala Pro Leu Ala Gly Thr Cys
        115                 120                 125

Gly Val Leu Leu Leu Ser Leu Val Ile Thr Leu Tyr Cys Asn His Arg
    130                 135                 140

Asn Arg Arg Arg Val Cys Lys Cys Pro Arg Pro Val Val Arg Ala Glu
145                 150                 155                 160

Gly Arg Gly Ser Leu Leu Thr Cys Gly Asp Val Glu Glu Asn Pro Gly
            165                 170                 175

Pro Met Glu Thr Asp Thr Leu Leu Leu Trp Val Leu Leu Leu Trp Val
        180                 185                 190

Pro Gly Ser Thr Gly Glu Val Gln Leu Gln Gln Ser Gly Pro Glu Leu
    195                 200                 205

Ile Lys Pro Gly Ala Ser Val Lys Met Ser Cys Lys Ala Ser Gly Tyr
    210                 215                 220

Thr Phe Thr Ser Tyr Val Met His Trp Val Lys Gln Lys Pro Gly Gln
225                 230                 235                 240

Gly Leu Glu Trp Ile Gly Tyr Ile Asn Pro Tyr Asn Asp Gly Thr Lys
            245                 250                 255

Tyr Asn Glu Lys Phe Lys Gly Lys Ala Thr Leu Thr Ser Asp Lys Ser
        260                 265                 270

Ser Ser Thr Ala Tyr Met Glu Leu Ser Ser Leu Thr Ser Glu Asp Ser
```

```
            275                 280                 285
Ala Val Tyr Tyr Cys Ala Arg Gly Thr Tyr Tyr Gly Ser Arg Val
        290                 295                 300

Phe Asp Tyr Trp Gly Gln Gly Thr Thr Leu Thr Val Ser Ser Gly Gly
305                 310                 315                 320

Gly Gly Ser Gly Gly Gly Ser Gly Gly Gly Ser Asp Ile Val
            325                 330                 335

Met Thr Gln Ala Ala Pro Ser Ile Pro Val Thr Pro Gly Glu Ser Val
        340                 345                 350

Ser Ile Ser Cys Arg Ser Ser Lys Ser Leu Leu Asn Ser Asn Gly Asn
        355                 360                 365

Thr Tyr Leu Tyr Trp Phe Leu Gln Arg Pro Gly Gln Ser Pro Gln Leu
    370                 375                 380

Leu Ile Tyr Arg Met Ser Asn Leu Ala Ser Gly Val Pro Asp Arg Phe
385                 390                 395                 400

Ser Gly Ser Gly Ser Gly Thr Ala Phe Thr Leu Arg Ile Ser Arg Val
                405                 410                 415

Glu Ala Glu Asp Val Gly Val Tyr Tyr Cys Met Gln His Leu Glu Tyr
            420                 425                 430

Pro Phe Thr Phe Gly Ala Gly Thr Lys Leu Glu Leu Lys Arg Ser Asp
        435                 440                 445

Pro Thr Thr Thr Pro Ala Pro Arg Pro Pro Thr Pro Ala Pro Thr Ile
    450                 455                 460

Ala Ser Gln Pro Leu Ser Leu Arg Pro Glu Ala Cys Arg Pro Ala Ala
465                 470                 475                 480

Gly Gly Ala Val His Thr Arg Gly Leu Asp Phe Ala Cys Asp Ile Tyr
                485                 490                 495

Ile Trp Ala Pro Leu Ala Gly Thr Cys Gly Val Leu Leu Leu Ser Leu
            500                 505                 510

Val Ile Thr Leu Tyr Cys Lys Arg Gly Arg Lys Lys Leu Leu Tyr Ile
        515                 520                 525

Phe Lys Gln Pro Phe Met Arg Pro Val Gln Thr Thr Gln Glu Glu Asp
    530                 535                 540

Gly Cys Ser Cys Arg Phe Pro Glu Glu Glu Gly Gly Cys Glu Leu
545                 550                 555                 560

Arg Val Lys Phe Ser Arg Ser Ala Asp Ala Pro Ala Tyr Gln Gln Gly
                565                 570                 575

Gln Asn Gln Leu Tyr Asn Glu Leu Asn Leu Gly Arg Arg Glu Glu Tyr
            580                 585                 590

Asp Val Leu Asp Lys Arg Arg Gly Arg Asp Pro Glu Met Gly Gly Lys
        595                 600                 605

Pro Arg Arg Lys Asn Pro Gln Glu Gly Leu Tyr Asn Glu Leu Gln Lys
    610                 615                 620

Asp Lys Met Ala Glu Ala Tyr Ser Glu Ile Gly Met Lys Gly Glu Arg
625                 630                 635                 640

Arg Arg Gly Lys Gly His Asp Gly Leu Tyr Gln Gly Leu Ser Thr Ala
                645                 650                 655

Thr Lys Asp Thr Tyr Asp Ala Leu His Met Gln Ala Leu Pro Pro Arg
            660                 665                 670

<210> SEQ ID NO 14
<211> LENGTH: 686
<212> TYPE: PRT
<213> ORGANISM: Artificial Sequence
```

<220> FEATURE:
<223> OTHER INFORMATION: Description of Artificial Sequence: Synthetic
      polypeptide
<220> FEATURE:
<223> OTHER INFORMATION: chimeric antigen receptor

<400> SEQUENCE: 14

```
Met Gly Thr Ser Leu Cys Trp Met Ala Leu Cys Leu Leu Gly Ala
1               5                   10                  15

Asp His Ala Asp Ala Glu Leu Pro Thr Gln Gly Thr Phe Ser Asn Val
            20                  25                  30

Ser Thr Asn Val Ser Ser Gly Gly Gly Ser Glu Leu Pro Thr Gln
        35                  40                  45

Gly Thr Phe Ser Asn Val Ser Thr Asn Val Ser Pro Ala Lys Pro Thr
    50                  55                  60

Thr Thr Ala Glu Leu Pro Thr Gln Gly Thr Phe Ser Asn Val Ser Thr
65                  70                  75                  80

Asn Val Ser Ser Gly Gly Gly Ser Pro Ala Pro Arg Pro Pro Thr
                85                  90                  95

Pro Ala Pro Thr Ile Ala Ser Gln Pro Leu Ser Leu Arg Pro Glu Ala
            100                 105                 110

Cys Arg Pro Ala Ala Gly Gly Ala Val His Thr Arg Gly Leu Asp Phe
            115                 120                 125

Ala Cys Asp Ile Tyr Ile Trp Ala Pro Leu Ala Gly Thr Cys Gly Val
        130                 135                 140

Leu Leu Leu Ser Leu Val Ile Thr Leu Tyr Cys Asn His Arg Asn Arg
145                 150                 155                 160

Arg Arg Val Cys Lys Cys Pro Arg Pro Val Val Arg Ala Glu Gly Arg
                165                 170                 175

Gly Ser Leu Leu Thr Cys Gly Asp Val Glu Glu Asn Pro Gly Pro Met
            180                 185                 190

Glu Thr Asp Thr Leu Leu Leu Trp Val Leu Leu Leu Trp Val Pro Gly
        195                 200                 205

Ser Thr Gly Glu Val Gln Leu Gln Gln Ser Gly Pro Glu Leu Ile Lys
    210                 215                 220

Pro Gly Ala Ser Val Lys Met Ser Cys Lys Ala Ser Gly Tyr Thr Phe
225                 230                 235                 240

Thr Ser Tyr Val Met His Trp Val Lys Gln Lys Pro Gly Gln Gly Leu
                245                 250                 255

Glu Trp Ile Gly Tyr Ile Asn Pro Tyr Asn Asp Gly Thr Lys Tyr Asn
            260                 265                 270

Glu Lys Phe Lys Gly Lys Ala Thr Leu Thr Ser Asp Lys Ser Ser Ser
        275                 280                 285

Thr Ala Tyr Met Glu Leu Ser Ser Leu Thr Ser Glu Asp Ser Ala Val
    290                 295                 300

Tyr Tyr Cys Ala Arg Gly Thr Tyr Tyr Gly Ser Arg Val Phe Asp
305                 310                 315                 320

Tyr Trp Gly Gln Gly Thr Thr Leu Thr Val Ser Ser Gly Gly Gly
                325                 330                 335

Ser Gly Gly Gly Ser Gly Gly Gly Ser Asp Ile Val Met Thr
            340                 345                 350

Gln Ala Ala Pro Ser Ile Pro Val Thr Pro Gly Glu Ser Val Ser Ile
        355                 360                 365

Ser Cys Arg Ser Ser Lys Ser Leu Leu Asn Ser Asn Gly Asn Thr Tyr
    370                 375                 380
```

```
Leu Tyr Trp Phe Leu Gln Arg Pro Gly Gln Ser Pro Gln Leu Leu Ile
385                 390                 395                 400

Tyr Arg Met Ser Asn Leu Ala Ser Gly Val Pro Asp Arg Phe Ser Gly
            405                 410                 415

Ser Gly Ser Gly Thr Ala Phe Thr Leu Arg Ile Ser Arg Val Glu Ala
        420                 425                 430

Glu Asp Val Gly Val Tyr Tyr Cys Met Gln His Leu Glu Tyr Pro Phe
            435                 440                 445

Thr Phe Gly Ala Gly Thr Lys Leu Glu Leu Lys Arg Ser Asp Pro Thr
    450                 455                 460

Thr Thr Pro Ala Pro Arg Pro Pro Thr Pro Ala Pro Thr Ile Ala Ser
465                 470                 475                 480

Gln Pro Leu Ser Leu Arg Pro Glu Ala Cys Arg Pro Ala Ala Gly Gly
                485                 490                 495

Ala Val His Thr Arg Gly Leu Asp Phe Ala Cys Asp Ile Tyr Ile Trp
            500                 505                 510

Ala Pro Leu Ala Gly Thr Cys Gly Val Leu Leu Leu Ser Leu Val Ile
        515                 520                 525

Thr Leu Tyr Cys Lys Arg Gly Arg Lys Lys Leu Leu Tyr Ile Phe Lys
    530                 535                 540

Gln Pro Phe Met Arg Pro Val Gln Thr Thr Gln Glu Glu Asp Gly Cys
545                 550                 555                 560

Ser Cys Arg Phe Pro Glu Glu Glu Gly Gly Cys Glu Leu Arg Val
                565                 570                 575

Lys Phe Ser Arg Ser Ala Asp Ala Pro Ala Tyr Gln Gln Gly Gln Asn
                580                 585                 590

Gln Leu Tyr Asn Glu Leu Asn Leu Gly Arg Arg Glu Glu Tyr Asp Val
            595                 600                 605

Leu Asp Lys Arg Arg Gly Arg Asp Pro Glu Met Gly Gly Lys Pro Arg
            610                 615                 620

Arg Lys Asn Pro Gln Glu Gly Leu Tyr Asn Glu Leu Gln Lys Asp Lys
625                 630                 635                 640

Met Ala Glu Ala Tyr Ser Glu Ile Gly Met Lys Gly Glu Arg Arg Arg
                645                 650                 655

Gly Lys Gly His Asp Gly Leu Tyr Gln Gly Leu Ser Thr Ala Thr Lys
            660                 665                 670

Asp Thr Tyr Asp Ala Leu His Met Gln Ala Leu Pro Pro Arg
        675                 680                 685

<210> SEQ ID NO 15
<211> LENGTH: 1189
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: artificial promoter

<400> SEQUENCE: 15
gcgtgaggct ccggtgcccg tcagtgggca gagcgcacat cgcccacagt ccccgagaag    60 ttgggggggag gggtcggcaa ttgaaccggt gcctagagaa ggtggcgcgg ggtaaactgg   120
gaaagtgatg tcgtgtactg gctccgcctt tttcccgagg gtgggggaga accgtatata   180
agtgcagtag tcgccgtgaa cgttcttttt cgcaacgggt ttgccgccag aacacaggta   240
```

```
agtgccgtgt gtggttcccg cgggcctggc ctctttacgg gttatggccc ttgcgtgcct    300
tgaattactt ccacgcccct ggctgcagta cgtgattctt gatcccgagc ttcgggttgg    360
aagtgggtgg gagagttcga ggccttgcgc ttaaggagcc ccttcgcctc gtgcttgagt    420
tgaggcctgg cctgggcgct ggggccgccg cgtgcgaatc tggtggcacc ttcgcgcctg    480
tctcgctgct ttcgataagt ctctagccat ttaaaatttt tgatgacctg ctgcgacgct    540 tttttctgg caagatagtc ttgtaaatgc gggccaagat ctgcacactg gtatttcggt    600
ttttggggcc gcgggcggcg acggggcccg tgcgtcccag cgcacatgtt cggcgaggcg    660
gggcctgcga gcgcggccac cgagaatcgg acggggtag tctcaagctg gccggcctgc    720
tctggtgcct ggcctcgcgc cgccgtgtat cgccccgccc tgggcggcaa ggctggcccg    780
gtcggcacca gttgcgtgag cggaaagatg gccgcttccc ggccctgctg cagggagctc    840
aaaatggagg acgcggcgct cggagagcg ggcgggtgag tcacccacac aaaggaaaag    900
ggcctttccg tcctcagccg tcgcttcatg tgactccacg gagtaccggg cgccgtccag    960
gcacctcgat tagttctcga gcttttggag tacgtcgtct ttaggttggg gggaggggtt   1020
ttatgcgatg gagtttcccc acactgagtg ggtggagact gaagttaggc cagcttggca   1080
cttgatgtaa ttctccttgg aatttgcccct ttttgagttt ggatcttggt tcattctcaa   1140
gcctcagaca gtggttcaaa gttttttttct tccatttcag gtgtcgtga              1189
```

<210> SEQ ID NO 16
<211> LENGTH: 237
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: promoter

<400> SEQUENCE: 16

```
gcgtgaggct ccggtgcccg tcagtgggca gagcgcacat cgcccacagt ccccgagaag     60 ttgggggggag gggtcggcaa ttgaaccggt gcctagagaa ggtggcgcgg ggtaaactgg    120
gaaagtgatg tcgtgtactg gctccgcctt tttcccgagg gtgggggaga accgtatata    180
agtgcagtag tcgccgtgaa cgttctttt cgcaacgggt tgccgccag aacacag         237
```

<210> SEQ ID NO 17
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: immunoglobulin gamma 1 heavy chain

<400> SEQUENCE: 17

```
Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Ile Lys
            20                  25                  30

Pro Gly Ala Ser Val Lys Met Ser Cys Lys Ala Ser Gly Tyr Thr Phe
        35                  40                  45

Thr Ser Tyr Val Met His Trp Val Lys Gln Lys Pro Gly Gln Gly Leu
    50                  55                  60

Glu Trp Ile Gly Tyr Ile Asn Pro Tyr Asn Asp Gly Thr Lys Tyr Asn
```

```
            65                  70                  75                  80
        Glu Lys Phe Lys Gly Lys Ala Thr Leu Thr Ser Asp Lys Ser Ser Ser
                        85                  90                  95

Thr Ala Tyr Met Glu Leu Ser Ser Leu Thr Ser Glu Asp Ser Ala Val
                        100                 105                 110

Tyr Tyr Cys Ala Arg Gly Thr Tyr Tyr Gly Ser Arg Val Phe Asp
                        115                 120                 125

Tyr Trp Gly Gln Gly Thr Thr Leu Thr Val Ser Ser Ala Lys Thr Thr
                        130                 135                 140

Pro Pro Ser Val Tyr Pro Leu Ala Pro Gly Ser Ala Ala Gln Thr Asn
        145                 150                 155                 160

Ser Met Val Thr Leu Gly Cys Leu Val Lys Gly Tyr Phe Pro Glu Pro
                        165                 170                 175

Val Thr Val Thr Trp Asn Ser Gly Ser Leu Ser Ser Gly Val His Thr
                        180                 185                 190

Phe Pro Ala Val Leu Gln Ser Asp Leu Tyr Thr Leu Ser Ser Ser Val
                        195                 200                 205

Thr Val Pro Ser Ser Thr Trp Pro Ser Glu Thr Val Thr Cys Asn Val
                        210                 215                 220

Ala His Pro Ala Ser Ser Thr Lys Val Asp Lys Lys Ile Val Pro Arg
        225                 230                 235                 240

Asp Cys Gly Cys Lys Pro Cys Ile Cys Thr Val Pro Glu Val Ser Ser
                        245                 250                 255

Val Phe Ile Phe Pro Pro Lys Pro Lys Asp Val Leu Thr Ile Thr Leu
                        260                 265                 270

Thr Pro Lys Val Thr Cys Val Val Asp Ile Ser Lys Asp Asp Pro
                        275                 280                 285

Glu Val Gln Phe Ser Trp Phe Val Asp Asp Val Glu Val His Thr Ala
                        290                 295                 300

Gln Thr Gln Pro Arg Glu Glu Gln Phe Asn Ser Thr Phe Arg Ser Val
        305                 310                 315                 320

Ser Glu Leu Pro Ile Met His Gln Asp Trp Leu Asn Gly Lys Glu Phe
                        325                 330                 335

Lys Cys Arg Val Asn Ser Ala Ala Phe Pro Ala Pro Ile Glu Lys Thr
                        340                 345                 350

Ile Ser Lys Thr Lys Gly Arg Pro Lys Ala Pro Gln Val Tyr Thr Ile
                        355                 360                 365

Pro Pro Pro Lys Glu Gln Met Ala Lys Asp Lys Val Ser Leu Thr Cys
                        370                 375                 380

Met Ile Thr Asp Phe Phe Pro Glu Asp Ile Thr Val Glu Trp Gln Trp
        385                 390                 395                 400

Asn Gly Gln Pro Ala Glu Asn Tyr Lys Asn Thr Gln Pro Ile Met Asp
                        405                 410                 415

Thr Asp Gly Ser Tyr Phe Val Tyr Ser Lys Leu Asn Val Gln Lys Ser
                        420                 425                 430

Asn Trp Glu Ala Gly Asn Thr Phe Thr Cys Ser Val Leu His Glu Gly
                        435                 440                 445

Leu His Asn His His Thr Glu Lys Ser Leu Ser His Ser Pro Gly Lys
                        450                 455                 460

<210> SEQ ID NO 18
<211> LENGTH: 239
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<223> OTHER INFORMATION: immunoglobulin kappa light chain

<400> SEQUENCE: 18

Met Arg Cys Leu Ala Glu Phe Leu Gly Leu Val Leu Trp Ile Pro
1               5                   10                  15

Gly Ala Ile Gly Asp Ile Val Met Thr Gln Ala Ala Pro Ser Ile Pro
            20                  25                  30

Val Thr Pro Gly Glu Ser Val Ser Ile Ser Cys Arg Ser Ser Lys Ser
                35                  40                  45

Leu Leu Asn Ser Asn Gly Asn Thr Tyr Leu Tyr Trp Phe Leu Gln Arg
        50                  55                  60

Pro Gly Gln Ser Pro Gln Leu Leu Ile Tyr Arg Met Ser Asn Leu Ala
65                  70                  75                  80

Ser Gly Val Pro Asp Arg Phe Ser Gly Ser Gly Ser Gly Thr Ala Phe
                85                  90                  95

Thr Leu Arg Ile Ser Arg Val Glu Ala Glu Asp Val Gly Val Tyr Tyr
                100                 105                 110

Cys Met Gln His Leu Glu Tyr Pro Phe Thr Phe Gly Ala Gly Thr Lys
                115                 120                 125

Leu Glu Leu Lys Arg Ala Asp Ala Ala Pro Thr Val Ser Ile Phe Pro
130                 135                 140

Pro Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
            195                 200                 205

Asp Glu Tyr Glu Arg His Asn Ser Tyr Thr Cys Glu Ala Thr His Lys
            210                 215                 220

Thr Ser Thr Ser Pro Ile Val Lys Ser Phe Asn Arg Asn Glu Cys
225                 230                 235

<210> SEQ ID NO 19
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: rituximab binding sequence

<400> SEQUENCE: 19

Cys Pro Tyr Ser Asn Pro Ser Leu Cys Ser Gly Gly Gly Gly Ser Glu
1               5                   10                  15

Leu Pro Thr Gln Gly Thr Phe Ser Asn Val Ser Thr Asn Val Ser Pro
                20                  25                  30

Ala Lys Pro Thr Thr Thr Ala Cys Pro Tyr Ser Asn Pro Ser Leu Cys
            35                  40                  45

Ser Gly Gly Gly Gly Ser Pro Ala Pro Arg Pro Pro Thr Pro Ala Pro
        50                  55                  60

Thr Ile Ala Ser Gln Pro Leu Ser Leu Arg Pro Glu Ala Cys Arg Pro
```

```
                65                  70                  75                  80
Ala Ala Gly Gly Ala Val His Thr Arg Gly Leu Asp Phe Ala Cys Asp
                    85                  90                  95

Ile Tyr Ile Trp Ala Pro Leu Ala Gly Thr Cys Gly Val Leu Leu Leu
                100                 105                 110

Ser Leu Val Ile Thr Leu Tyr Cys Asn His Arg Asn Arg Arg Arg Val
                115                 120                 125

Cys Lys Cys Pro Arg Pro Val Val
            130                 135

<210> SEQ ID NO 20
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: signal peptide

<400> SEQUENCE: 20

Met Gly Thr Ser Leu Leu Cys Trp Met Ala Leu Cys Leu Leu Gly Ala
1               5                   10                  15

Asp His Ala Asp Ala
            20

<210> SEQ ID NO 21
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Gly Thr Ser Leu Leu Cys Trp Met Ala Leu Cys Leu Leu Gly Ala
1               5                   10                  15

Asp His Ala Asp Ala Cys Pro Tyr Ser Asn Pro Ser Leu Cys Ser Gly
            20                  25                  30

Gly Gly Gly Ser Glu Leu Pro Thr Gln Gly Thr Phe Ser Asn Val Ser
        35                  40                  45

Thr Asn Val Ser Pro Ala Lys Pro Thr Thr Thr Ala Cys Pro Tyr Ser
    50                  55                  60

Asn Pro Ser Leu Cys Ser Gly Gly Gly Ser Pro Ala Pro Arg Pro
65                  70                  75                  80

Pro Thr Pro Ala Pro Thr Ile Ala Ser Gln Pro Leu Ser Leu Arg Pro
                85                  90                  95

Glu Ala Cys Arg Pro Ala Ala Gly Gly Ala Val His Thr Arg Gly Leu
                100                 105                 110

Asp Phe Ala Cys Asp Ile Tyr Ile Trp Ala Pro Leu Ala Gly Thr Cys
            115                 120                 125

Gly Val Leu Leu Leu Ser Leu Val Ile Thr Leu Tyr Cys Asn His Arg
        130                 135                 140

Asn Arg Arg Arg Val Cys Lys Cys Pro Arg Pro Val Val
145                 150                 155

<210> SEQ ID NO 22
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 22

Cys Pro Tyr Ser Asn Pro Ser Leu Cys
1               5

<210> SEQ ID NO 23
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asn Ser Glu Leu Leu Ser Leu Ile Asn Asp Met Pro Ile Thr Asn Asp
1               5                   10                  15

Gln Lys Lys Leu Met Ser Asn Asn
            20

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Cys Gln Phe Asp Leu Ser Thr Arg Arg Leu Lys Cys
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Cys Gln Tyr Asn Leu Ser Ser Arg Ala Leu Lys Cys
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Cys Val Trp Gln Arg Trp Gln Lys Ser Tyr Val Cys
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27
```

```
Cys Met Trp Asp Arg Phe Ser Arg Trp Tyr Lys Cys
1               5                   10
```

<210> SEQ ID NO 28
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Ser Phe Val Leu Asn Trp Tyr Arg Met Ser Pro Ser Asn Gln Thr Asp
1               5                   10                  15

Lys Leu Ala Ala Phe Pro Glu Asp Arg
            20                  25
```

<210> SEQ ID NO 29
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Ser Gly Thr Tyr Leu Cys Gly Ala Ile Ser Leu Ala Pro Lys Ala Gln
1               5                   10                  15

Ile Lys Glu
```

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

```
Glu Leu Pro Thr Gln Gly Thr Phe Ser Asn Val Ser Thr Asn Val Ser
1               5                   10                  15
```

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

```
Gly Gln Asn Asp Thr Ser Gln Thr Ser Ser Pro Ser
1               5                   10
```

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

```
Gly Leu Ala Val Ser Thr Ile Ser Ser Phe Phe Pro Pro Gly Tyr Gln
1               5                   10                  15
```

<210> SEQ ID NO 33
<211> LENGTH: 45
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 33

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45
```

<210> SEQ ID NO 34
<211> LENGTH: 231
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 34

```
Glu Pro Lys Ser Pro Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ala Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230
```

<210> SEQ ID NO 35
<211> LENGTH: 21
<212> TYPE: PRT

<213> ORGANISM: Artificial Sequence
<220> FEATURE:
<223> OTHER INFORMATION: Description of Artificial Sequence: Synthetic peptide

<400> SEQUENCE: 35

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 36
<211> LENGTH: 66
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 36

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr
65

<210> SEQ ID NO 37
<211> LENGTH: 42
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 38
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 38

Leu Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
            20                  25                  30

Tyr Asp Val Leu Asp Lys Arg Arg Gly Arg Asp Pro Glu Met Gly Gly
        35                  40                  45

```
Lys Pro Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg
```

```
<210> SEQ ID NO 39
<211> LENGTH: 943
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: intron

<400> SEQUENCE: 39
gtaagtgccg tgtgtggttc ccgcgggcct ggcctcttta cgggttatgg cccttgcgtg      60
ccttgaatta cttccacgcc cctggctgca gtacgtgatt cttgatcccg agcttcgggt     120
tggaagtggg tgggagagtt cgaggccttg cgcttaagga gccccttcgc ctcgtgcttg     180
agttgaggcc tggcctgggc gctggggccg ccgcgtgcga atctggtggc accttcgcgc     240
ctgtctcgct gctttcgata agtctctagc catttaaaat ttttgatgac ctgctgcgac     300
gctttttttc tggcaagata gtcttgtaaa tgcgggccaa gatctgcaca ctggtatttc     360
ggtttttggg gccgcgggcg gcgacggggc ccgtgcgtcc cagcgcacat gttcggcgag     420
gcggggcctg cgagcgcggc caccgagaat cggacggggg tagtctcaag ctggccggcc     480
tgctctggtg cctggcctcg cgccgccgtg tatcgccccg ccctgggcgg caaggctggc     540
ccggtcggca ccagttgcgt gagcggaaag atggccgctt cccggccctg ctgcagggag     600
ctcaaaatgg aggacgcggc gctcgggaga gcgggcgggt gagtcaccca cacaaaggaa     660
aagggccttt ccgtcctcag ccgtcgcttc atgtgactcc acggagtacc gggcgccgtc     720
caggcacctc gattagttct cgagcttttg gagtacgtcg tctttaggtt ggggggaggg     780
gttttatgcg atggagtttc cccacactga gtgggtggag actgaagtta ggccagcttg     840
gcacttgatg taattctcct tggaatttgc cctttttgag tttggatctt ggttcattct     900
caagcctcag acagtggttc aaagtttttt tcttccattt cag                       943
```

```
<210> SEQ ID NO 40
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: mutated rituximab binding sequences

<400> SEQUENCE: 40

Cys Ser Gly Gly Gly Gly Gly Ser Cys Ser Gly Gly Gly Gly Ser Glu
1               5                   10                  15

Leu Pro Thr Gln Gly Thr Phe Ser Asn Val Ser Thr Asn Val Ser Pro
            20                  25                  30

Ala Lys Pro Thr Thr Thr Ala Cys Ser Gly Gly Gly Gly Gly Ser Cys
```

```
                    35                  40                  45
Ser Gly Gly Gly Gly Ser Pro Ala Pro Arg Pro Pro Thr Pro Ala Pro
    50                  55                  60

Thr Ile Ala Ser Gln Pro Leu Ser Leu Arg Pro Glu Ala Cys Arg Pro
65                  70                  75                  80

Ala Ala Gly Gly Ala Val His Thr Arg Gly Leu Asp Phe Ala Cys Asp
                85                  90                  95

Ile Tyr Ile Trp Ala Pro Leu Ala Gly Thr Cys Gly Val Leu Leu Leu
                100                 105                 110

Ser Leu Val Ile Thr Leu Tyr Cys Asn His Arg Asn Arg Arg Arg Val
            115                 120                 125

Cys Lys Cys Pro Arg Pro Val Val
    130                 135

<210> SEQ ID NO 41
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(25)
<223> OTHER INFORMATION: This sequence may encompass 1-5 "Gly Gly Gly
      Gly Ser" repeating units

<400> SEQUENCE: 41

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```

POLYNUCLEOTIDES ENCODING RITUXIMAB-RESISTANT CHIMERIC ANTIGEN RECEPTORS

CROSS REFERENCE TO RELATED APPLICATIONS

The present application claims the benefit of priority to U.S. Provisional Application No. 62/839,455, filed on Apr. 26, 2019; and U.S. Provisional Application No. 63/005,041, filed on Apr. 3, 2020, the contents of both of which are hereby incorporated by reference in their entireties.

TECHNICAL FIELD

This disclosure relates to chimeric antigen receptors (CARs) comprising an antigen binding molecule which binds to CD19, polynucleotides encoding the same, and methods of treating a cancer in a patient using the same.

SEQUENCE LISTING

This application contains a Sequence Listing which has been submitted electronically in ASCII format and is hereby incorporated by reference in its entirety. Said ASCII copy, created on Apr. 24, 2020, is named AT-028_03US_SL.txt and is 80,074 bytes in size.

BACKGROUND

Adoptive transfer of immune cells genetically modified to recognize malignancy-associated antigens is showing promise as a new approach to treating cancer (see, e.g., Brenner et al., Current Opinion in Immunology, 22(2): 251-257 (2010); Rosenberg et al., Nature Reviews Cancer, 8(4): 299-308 (2008)). Immune cells can be genetically modified to express chimeric antigen receptors (CARs), fusion proteins comprised of a CD19 antigen recognition moiety and T cell activation domains (see, e.g., Eshhar et al., Proc. Natl. Acad. Sci. USA, 90(2): 720-724 (1993), and Sadelain et al., Curr. Opin. Immunol, 21(2): 215-223 (2009)). Immune cells that contain CARs, e.g., CAR-T cells (CAR-Ts), are engineered to endow them with antigen specificity while retaining or enhancing their ability to recognize and kill a target cell.

There is a need for treatments for cancer and in particular malignancies involving aberrant expression of CD19. Provided herein are methods and compositions addressing this need.

SUMMARY

Provided herein are chimeric antigen receptors (CARs) comprising a CD19 antigen binding domain that specifically binds to CD19; polynucleotides encoding these CARs; and immune cells expressing these CD19-specific CARs, e.g., CAR-T cells. Also provided are methods of making and using these CD19-specific CARs, and immune cells comprising these CD19-specific CARs.

In one aspect, the disclosure provides an isolated polynucleotide encoding a polypeptide comprising an anti-CD19 chimeric antigen receptor (CAR) that is at least 70% identical to SEQ ID NO: 9, wherein the polypeptide does not comprise a rituximab binding site, and wherein the polynucleotide comprises a short EF1a promoter that is capable of expressing the anti-CD19 chimeric antigen receptor (CAR) in a mammalian T cell.

In some embodiments, the short EF1a promoter does not comprise an intron sequence within the nucleic acid sequence of SEQ ID NO:15. In some embodiments, the intron comprises the nucleic acid sequence of SEQ ID NO:39.

In some embodiments, the promoter comprises the nucleic acid sequence of SEQ ID NO:16, In some embodiments, the promoter is a full length EF1a promoter comprising the nucleic acid sequence of SEQ ID NO:15.

In some embodiments, the promoter comprises the nucleic acid sequence of SEQ ID NO:15, and the polynucleotide encodes a polypeptide that is at least about 80%, 85%, 90%, 95%, 96%, 98%, 99% or 100% identical to any one of SEQ ID NO: 8-14.

In some embodiments, the polypeptide further comprises a safety switch.

In some embodiments, the safety switch is linked to the CD19 CAR using a linker peptide.

In some embodiments, the safety switch is linked to the anti-CD19 CAR using a T2A linker.

In some embodiments, the safety switch comprises an antibody binding site.

In some embodiments, the safety switch comprises a mutated CD20 mimotope.

In some embodiments, the polypeptide further comprises a CD8 hinge/transmembrane domain.

In some embodiments, the polypeptide comprises a CD34 epitope.

In some embodiments, the CD34 epitope is a QBEND-10 epitope.

In some embodiments, the isolated polynucleotide comprises a nucleic acid sequence that is at least about 80%, 85%, 90%, 95%, 96%, 98%, 99% or 100% identical to any one of SEQ ID NO: 1-7.

In some embodiments, the isolated polynucleotide encodes a polypeptide that is at least about 80%, 85%, 90%, 95%, 96%, 98%, 99% or 100% identical to any one of SEQ ID NO: 8-14.

In another aspect, the disclosure provides a vector comprising the isolated polynucleotide described herein.

In some embodiments, the vector is a retroviral vector, a DNA vector, a plasmid, an RNA vector, an adenoviral vector, an adenovirus associated vector, a lentiviral vector, or any combination thereof.

In one aspect, the disclosure provides an engineered immune cell comprising the isolated polynucleotide described herein.

In some embodiments, the disclosure provides an engineered immune cell comprising a polynucleotide that comprises a nucleic acid sequence that is at least about 80%, 85%, 90%, 95%, 96%, 98%, 99% or 100% identical to SEQ ID NO: 3.

In some embodiments, the disclosure provides an engineered immune cell comprising a polynucleotide that is at least about 80%, 85%, 90%, 95%, 96%, 98%, 99% or 100% identical to the anti-CD19 CAR v1.2, v1.3, v1.4, v1.5 or v1.6 lentiviral construct as shown in Table 1.

In some embodiments, the disclosure provides an engineered immune cell comprising a polynucleotide that is at least about 80%, 85%, 90%, 95%, 96%, 98%, 99% or 100% identical to the anti-CD19 CAR v1.2 lentiviral construct as shown in Table 1.

In some embodiments, the disclosure provides an engineered immune cell comprising a polynucleotide that encodes a polypeptide that is at least about 80%, 85%, 90%, 95%, 96%, 98%, 99% or 100% identical to SEQ ID NO:9 or SEQ ID NO:10, with or without the signal sequence.

In some embodiments, the disclosure provides an engineered immune cell comprising a polynucleotide that comprises the nucleic acid sequence of SEQ ID NO:3, driven by an EF1a short promoter comprising the nucleic acid of SEQ ID NO:16.

In some embodiments, the disclosure provides an engineered immune cell comprising a polynucleotide that encodes a polypeptide sequence of SEQ ID NO:9 or 10, with or without the signal sequence, driven by an EF1a short promoter comprising the nucleic acid of SEQ ID NO:16. In some embodiments, the promoter does not comprise the first intron of the EF1a gene.

In some embodiments, the engineered immune cell does not comprise a rituximab mimotope.

In some embodiments, the engineered immune cell comprises a polynucleotide comprising the CD19 CAR v1.2 lentiviral construct as shown in FIG. 1 (may also be referred to as ALLO-501A).

In some embodiments, the engineered immune cell comprises a vector described herein.

In some embodiments, the immune cell is a T cell, tumor infiltrating lymphocyte (TIL), NK cell, TCR-expressing cell, dendritic cell, or NK-T cell.

In some embodiments, the cell is an autologous T cell.

In some embodiments, the cell is an allogeneic T cell.

In one aspect, the disclosure provides an engineered immune cell described herein, wherein the cell is resistant to rituximab.

In another aspect, the disclosure provides a pharmaceutical composition comprising the engineered immune cell described herein.

In one aspect, the disclosure provides a method of treating a disease or disorder in a subject in need thereof comprising administering to the subject the engineered immune cell described herein, or the pharmaceutical composition described herein.

In some embodiments, the disease or disorder is Non-Hodgkin lymphoma (NHL).

In some embodiments, the subject has been treated or is currently being treated with rituximab.

In one aspect, the disclosure provides an article of manufacture comprising the engineered immune cell or the pharmaceutical composition comprising the engineered immune cell expressing a chimeric antigen receptors described herein.

BRIEF DESCRIPTION OF THE DRAWINGS

FIG. 2A shows CAR expression on cells from donor 541 and 604. FIG. 2B shows CAR and CD34 expression on cells from donor 410. A similar profile was observed with donor 2593 (data not shown).

DETAILED DESCRIPTION

Figure 1:
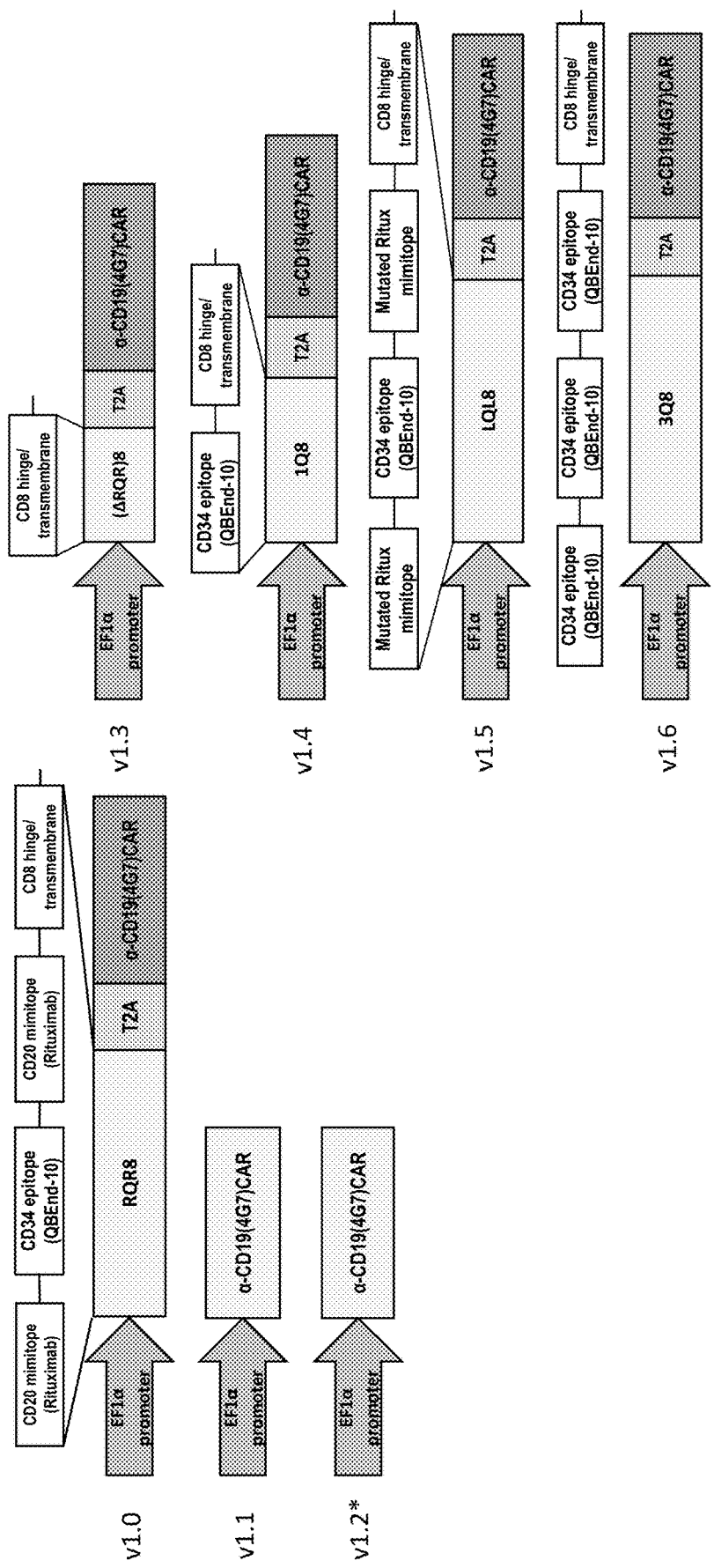
FIG. 1 shows schematic representations of rituximab-resistant CD19 chimeric antigen receptors.

Chimeric Antigen Receptor (CAR) therapy is a promising approach to cancer treatment. The CAR construct described herein as v1.0 is an exemplary anti-CD19 CAR that expresses a synthetic peptide, RQR8, which serves as a safety switch. RQR8 contains two rituximab-binding mimotopes. In the instance of an adverse event, patients may be treated with rituximab to deplete the levels of anti-CD19 v1.0 in circulation. Rituximab is also used as the standard of care in some Non-Hodgkin Lymphoma (NHL) indications and is administered at high doses. Due to the long half-life of rituximab, anti-CD19 v1.0 cannot be administered to patients until the level of circulating rituximab has reached a low concentration. Rituximab-resistant CD19 CAR therapy would allow patients who were previously treated with rituximab to receive CAR-T therapy immediately, without having to wait for rituximab levels to diminish and without patients being subjected to apheresis. Provided herein are anti-CD19 chimeric antigen receptors (CARs) that are resistant to the CD20 binding antibody rituximab. The novel CAR constructs are designed to eliminate rituximab binding while retaining CAR expression and activity.

I. Chimeric Antigen Receptors

As used herein, chimeric antigen receptors (CARs) are proteins that specifically recognize target antigens (e.g., target antigens on cancer cells). When bound to the target antigen, the CAR may activate the immune cell to attack and destroy the cell bearing that antigen (e.g., the cancer cell). CARs may also incorporate costimulatory or signaling domains to increase their potency. See Krause et al., J. Exp.

Chimeric antigen receptors described herein comprise an extracellular domain, a transmembrane domain, and an intracellular domain, wherein the extracellular domain comprises a CD19 antigen binding domain that specifically binds to CD19. In some embodiments, the CD19 specific CAR comprises the following elements from 5' to 3': a signal sequence, a CD19 antigen binding domain (e.g., a scFv derived from 4G7), a hinge and transmembrane region, and one or more successive signaling domains. In some embodiments, the antibody binding domain binds CD19 to treat a hematologic cancer associated with expression of CD19.

The scFv portion of the chimeric antigen receptor (CAR) used in the allogeneic anti-CD19 CAR v1.0 is derived from the mouse anti-human CD19 antibody clone 4G7. 4G7 is a CD19 monoclonal antibody that recognizes CD19. Single chain variable fragments (scFv) formed from 4G7 comprise the targeting component of some chimeric antigen receptors (CARs) (See WO2014184143A1). In some embodiments, the scFv derived from the CD19 monoclonal antibody 4G7, comprises a part of the CD19 monoclonal antibody 4G7 immunoglobulin gamma 1 heavy chain (GenBank: CAD88275.1; SEQ ID NO: 17) and a part of CD19 monoclonal antibody 4G7 immunoglobulin kappa light chain (GenBank: CAD88204.1; SEQ ID NO: 35), linked together by a flexible linker. (Peipp M., D. Saul, et al., 2004. Efficient eukaryotic expression of fluorescent scFv fusion proteins directed against CD antigens for FACS applications. *J. Immuno. Methods* 285: 265-280). In some embodiments, the scFv comprises the variable fragments of the CD19 monoclonal antibody 4G7 immunoglobulin gamma 1 heavy chain and the variable fragments of the CD19 monoclonal antibody 4G7 immunoglobulin kappa light chain linked together by a flexible linker.

CD19 monoclonal antibody 4G7 immunoglobulin gamma 1 heavy chain (the signal sequence is underlined)

(SEQ ID NO: 17)
<u>MEWSWIFLFLLSGTAGVHS</u>EVQLQQSGPELIKPGASVKMSCKASGYTFTS

YVMHWVKQKPGQGLEWIGYINPYNDGTKYNEKFKGKATLTSDKSSSTAYM

ELSSLTSEDSAVYYCARGTYYYGSRVFDYWGQGTTLTVSSAKTTPPSVYP

LAPGSAAQTNSMVTLGCLVKGYFPEPVTVTWNSGSLSSGVHTFPAVLQSD

LYTLSSSVTVPSSTWPSETVTCNVAHPASSTKVDKKIVPRDCGCKPCICT

VPEVSSVFIFPPKPKDVLTITLTPKVTCVVVDISKDDPEVQFSWFVDDVE

VHTAQTQPREEQFNSTFRSVSELPIMHQDWLNGKEFKCRVNSAAFPAPIE

KTISKTKGRPKAPQVYTIPPPKEQMAKDKVSLTCMITDFFPEDITVEWQW

NGQPAENYKNTQPIMDTDGSYFVYSKLNVQKSNWEAGNTFTCSVLHEGLH

NHHTEKSLSHSPGK

CD19 monoclonal antibody 4G7 immunoglobulin kappa light chain (the signal sequence is underlined)

(SEQ ID NO: 18)
<u>MRCLAEFLGLLVLWIPGAIG</u>DIVMTQAAPSIPVTPGESVSISCRSSKSLL

NSNGNTYLYWFLQRPGQSPQLLIYRMSNLASGVPDRFSGSGSGTAFTLRI

SRVEAEDVGVYYCMQHLEYPFTFGAGTKLELKRADAAPTVSIFPPSSEQL

TSGGASVVCFLNNFYPKDINVKWKIDGSERQNGVLNSWTDQDSKDSTYSM

SSTLTLTKDEYERHNSYTCEATHKTSTSPIVKSFNRNEC

In some embodiments, the scFv comprises a part of amino acid sequences of SEQ ID NO: 17 and/or SEQ ID NO: 18. In some embodiments, the scFv comprises at least 70%, at least 80%, at least 90%, at least 95%, at least 97% or at least 99% sequence identity with the variable region of amino acid sequence of 34 and/or SEQ ID NO: 35. Disclosed herein are antigen binding molecules, including antibodies, that specifically bind to the anti-CD19 scFv derived from 4G7, as well as molecules comprising these sequences and cells presenting such molecules. Humanized forms of the antigen binding molecules also form as aspect of the disclosure. Applications and uses of these antigen binding molecules are also disclosed.

a. Antigen Binding Domain

As discussed above, the CD19 CARs described herein comprise an antigen binding domain. An "antigen binding domain" as used herein means any polypeptide that binds a specified target antigen, for example the specified target antigen can be the CD19 protein or fragment thereof. In some embodiments, the antigen binding domain binds to a CD19 antigen on a tumor cell. In some embodiments, the antigen binding domain binds to a CD19 antigen on a cell involved in a hyperproliferative disease.

In some embodiments, the antigen binding domain comprises a variable heavy chain, variable light chain, and/or one or more CDRs. In some embodiments, the antigen binding domain is a single chain variable fragment (scFv), comprising light chain CDRs CDR1, CDR2 and CDR3, and heavy chain CDRs CDR1, CDR2 and CDR3. Variants of the antigen binding domains (e.g., variants of the CDRs, VH and/or VL) are also within the scope of the disclosure, e.g., variable light and/or variable heavy chains that each have at least 70-80%, 80-85%, 85-90%, 90-95%, 95-97%, 97-99%, or above 99% identity to the amino acid sequences of the antigen binding domain sequences described herein. In some instances, such molecules include at least one heavy chain and one light chain, whereas in other instances the variant forms contain two variable light chains and two variable heavy chains (or subparts thereof). A skilled artisan will be able to determine suitable variants of the antigen binding domains as set forth herein using well-known techniques. In certain embodiments, one skilled in the art can identify suitable areas of the molecule that may be changed without destroying activity by targeting regions not believed to be important for activity.

In certain embodiments, the polypeptide structure of the antigen binding domains is based on antibodies, including, but not limited to, monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the antigen binding domain comprises or consists of avimers.

A CD19 antigen binding domain is said to be "selective" when it binds to one target more tightly than it binds to a second target. In some embodiments, the CD19 antigen binding domain is a scFv.

In some embodiments, the disclosure relates to isolated polynucleotides encoding any one of the CD19 chimeric antigen receptors (CARs) described herein. In some embodiments, the disclosure relates to isolated polynucleotides encoding a CD19 CAR described in Table 1. Also provided herein are vectors comprising the polynucleotides, and methods of making the same.

TABLE 1

Polynucleotide Sequences of exemplary CD19 targeting CARs

| SEQ ID NO | Description | Sequence |
|---|---|---|
| 1 | anti-CD19 CAR_v1.0 | ATGCTGACCAGCCTGCTGTGCTGGATGGCCCTGTGCCTGCTG<br>GGCGCCGACCACGCCGATGCCTGCCCCTACAGCAACCCCAG<br>CCTGTGCAGCGGAGGCGGCGGCAGCGAGCTGCCCACCCAGG<br>GCACCTTCTCCAACGTGTCCACCAACGTGAGCCCAGCCAAG<br>CCCACCACCACCGCCTGTCCTTATTCCAATCCTTCCCTGTGT<br>AGCGGAGGGGGAGGCAGCCCAGCCCCCAGACCTCCCACCCC<br>AGCCCCCACCATCGCCAGCCAGCCTCTGAGCCTGAGACCCG<br>AGGCCTGCCGCCCAGCCGCCGGCGGCGCCGTGCACACCAGA<br>GGCCTGGATTTCGCCTGCGATATCTACATCTGGGCCCCACTG<br>GCCGGCACCTGTGGCGTGCTGCTGCTGAGCCTGGTGATCACC<br>CTGTACTGCAACCACCGCAACCGCAGGCGCGTGTGCAAGTG<br>CCCCAGGCCCGTGGTGAGAGCCGAGGGCAGAGGCAGCCTGC<br>TGACCTGCGGCGACGTGGAGGAGAACCCAGGCCCCATGGAG<br>ACCGACACCCTGCTGCTGTGGGTGCTGCTGCTGTGGGTGCCA<br>GGCAGCACCGGCGAGGTGCAGCTGCAGCAGAGCGGACCCG<br>AGCTGATCAAGCCAGGCGCCAGCGTGAAGATGAGCTGCAAG<br>GCCAGCGGCTACACCTTCACCAGCTACGTGATGCACTGGGT<br>GAAGCAGAAGCCAGGCCAGGGCCTGGAGTGGATCGGCTAC<br>ATCAACCCCTACAACGACGGCACCAAGTACAACGAGAAGTT<br>CAAGGGCAAGGCCACCCTGACCAGCGACAAGAGCAGCAGC<br>ACCGCCTACATGGAGCTGAGCAGCCTGACCAGCGAGGACAG<br>CGCCGTGTACTACTGCGCCAGAGGCACCTACTACTACGGCA<br>GCCGGGTGTTCGACTACTGGGGCCAGGGCACCACCCTGACC<br>GTGAGCTCTGGCGGAGGCGGCTCTGGCGGAGGCGGCTCTGG<br>CGGAGGCGGCAGCGACATCGTGATGACCCAGGCTGCCCCCA<br>GCATCCCCGTGACCCCAGGCGAGAGCGTGAGCATCAGCTGC<br>CGGAGCAGCAAGAGCCTGCTGAACAGCAACGGCAACACCTA<br>CCTGTACTGGTTCCTGCAGCGGCCAGGCCAGAGCCCCCAGC<br>TGCTGATCTACCGGATGAGCAACCTGGCCAGCGGCGTGCCC<br>GACCGGTTCAGCGGCAGCGGCAGCGGCACCGCCTTCACCCT<br>GCGGATCAGCCGGGTGGAGGCCGAGGACGTGGGCGTGTACT<br>ACTGCATGCAGCACCTGGAGTACCCCTTCACCTTCGGAGCCG<br>GCACCAAGCTGGAGCTGAAGCGGTCGGATCCCACCACCACC<br>CCAGCCCCACGGCCACCTACCCCTGCCCCAACCATCGCCAG<br>CCAGCCCCTGAGCCTGCGGCCTGAAGCCTGCAGGCCTGCCG<br>CCGGAGGAGCCGTGCACACAAGGGGCCTGGACTTCGCCTGC<br>GACATCTATATCTGGGCCCCCCTGGCCGGGACATGCGGGGT<br>GCTGCTGCTGTCCCTGGTGATTACACTGTATTGCAAACGGGG<br>CCGGAAGAAGCTGCTGTACATCTTCAAGCAGCCCTTCATGC<br>GGCCCGTGCAGACCACCCAGGAGGAGGACGGCTGCAGCTGC<br>CGGTTCCCCGAGGAAGAGGAAGGCGGCTGCGAGCTGCGGGT<br>GAAGTTCAGCCGGAGCGCCGACGCCCCAGCCTACCAGCAGG<br>GCCAGAACCAGCTGTACAACGAGCTGAACCTGGGACGGCGG<br>GAGGAGTACGACGTGCTGGACAAGCGGCGGGACGGGACC<br>CCGAGATGGGCGGCAAGCCTCGCCGGAAGAATCCCCAGGAG<br>GGCCTGTACAACGAGCTGCAGAAGGACAAGATGGCCGAGG<br>CCTACAGCGAGATCGGCATGAAGGGCGAGCGGCGCCGGGG<br>CAAGGGCCACGACGGCCTGTACCAGGGCCTGAGCACCGCCA<br>CCAAGGACACCTACGACGCCCTGCACATGCAGGCCCTGCCA<br>CCCCGGTGA |
| 2 | anti-CD19 CAR_v1.1 | ATGGAGACCGACACCCTGCTGCTGTGGGTGCTGCTGCTGTG<br>GGTGCCAGGCAGCACCGGCGAGGTGCAGCTGCAGCAGAGC<br>GGACCCGAGCTGATCAAGCCAGGCGCCAGCGTGAAGATGAG<br>CTGCAAGGCCAGCGGCTACACCTTCACCAGCTACGTGATGC<br>ACTGGGTGAAGCAGAAGCCAGGCCAGGGCCTGGAGTGGATC<br>GGCTACATCAACCCCTACAACGACGGCACCAAGTACAACGA<br>GAAGTTCAAGGGCAAGGCCACCCTGACCAGCGACAAGAGC<br>AGCAGCACCGCCTACATGGAGCTGAGCAGCCTGACCAGCGA<br>GGACAGCGCCGTGTACTACTGCGCCAGAGGCACCTACTACT<br>ACGGCAGCCGGGTGTTCGACTACTGGGGCCAGGGCACCACC<br>CTGACCGTGAGCTCTGGCGGAGGCGGCTCTGGCGGAGGCGG<br>CTCTGGCGGAGGCGGCAGCGACATCGTGATGACCCAGGCTG<br>CCCCCAGCATCCCCGTGACCCCAGGCGAGAGCGTGAGCATC<br>AGCTGCCGGAGCAGCAAGAGCCTGCTGAACAGCAACGGCA<br>ACACCTACCTGTACTGGTTCCTGCAGCGGCCAGGCCAGAGC<br>CCCCAGCTGCTGATCTACCGGATGAGCAACCTGGCCAGCGG<br>CGTGCCCGACCGGTTCAGCGGCAGCGGCAGCGGCACCGCCT<br>TCACCCTGCGGATCAGCCGGGTGGAGGCCGAGGACGTGGGC<br>GTGTACTACTGCATGCAGCACCTGGAGTACCCCTTCACCTTC<br>GGAGCCGGCACCAAGCTGGAGCTGAAGCGGTCGGATCCCAC<br>CACCACCCCAGCCCCACGGCCACCTACCCCTGCCCCAACCAT |

TABLE 1-continued

Polynucleotide Sequences of exemplary CD19 targeting CARs

| SEQ ID NO | Description | Sequence |
|---|---|---|
| | | CGCCAGCCAGCCCCTGAGCCTGCGGCCTGAAGCCTGCAGGC<br>CTGCCGCCGGAGGAGCCGTGCACACAAGGGGCCTGGACTTC<br>GCCTGCGACATCTATATCTGGGCCCCCCTGGCCGGGACATGC<br>GGGGTGCTGCTGCTGTCCCTGGTGATTACACTGTATTGCAAA<br>CGGGGCCGGAAGAAGCTGCTGTACATCTTCAAGCAGCCCTT<br>CATGCGGCCCGTGCAGACCACCCAGGAGGAGGACGGCTGCA<br>GCTGCCGGTTCCCCGAGGAAGAGGAAGGCGGCTGCGAGCTG<br>CGGGTGAAGTTCAGCCGGAGCGCCGACGCCCCAGCCTACCA<br>GCAGGGCCAGAACCAGCTGTACAACGAGCTGAACCTGGGAC<br>GGCGGGAGGAGTACGACGTGCTGGACAAGCGGCGGGGACG<br>GGACCCCGAGATGGGCGGCAAGCCTCGCCGGAAGAATCCCC<br>AGGAGGGCCTGTACAACGAGCTGCAGAAGGACAAGATGGC<br>CGAGGCCTACAGCGAGATCGGCATGAAGGGCGAGCGGCGC<br>CGGGGCAAGGGCCACGACGGCCTGTACCAGGGCCTGAGCAC<br>CGCCACCAAGGACACCTACGACGCCCTGCACATGCAGGCCC<br>TGCCACCCCGGTGA |
| 3 | anti-CD19<br>CAR_v1.2 | ATGGAGACAGATACCCTGCTGCTGTGGGTGCTGCTGCTGTG<br>GGTGCCTGGCTCCACAGGAGAGGTGCAGCTGCAGCAGTCTG<br>GACCAGAGCTGATCAAGCCTGGAGCATCCGTGAAGATGTCT<br>TGCAAGGCCAGCGGCTATACATTCACCAGCTACGTGATGCA<br>CTGGGTGAAGCAGAAGCCTGGCCAGGGCCTGGAGTGGATCG<br>GCTATATCAATCCATACAACGACGGCACCAAGTATAATGAG<br>AAGTTTAAGGGCAAGGCCACACTGACCCTCTGATAAGAGCTC<br>CTCTACAGCCTACATGGAGCTGAGCTCCCTGACCTCTGAGGA<br>CAGCGCCGTGTACTATTGCGCCAGAGGCACATACTATTACG<br>GCAGCAGGGTGTTCGATTACTGGGGCCAGGGCACCACACTG<br>ACCGTGTCTAGCGGAGGAGGAGGCTCCGGAGGAGGAGGCTC<br>TGGCGGCGGCGGCAGCGACATCGTGATGACACAGGCAGCAC<br>CAAGCATCCCAGTGACCCCTGGCGAGAGCGTGTCCATCTCTT<br>GTCGGTCCTCTAAGTCCCTGCTGAACTCTAATGGCAACACCT<br>ATCTGTACTGGTTTCTGCAGCGGCCCGGACAGTCCCCACAGC<br>TGCTGATCTATAGGATGAGCAACCTGGCATCCGGAGTGCCT<br>GATCGCTTCAGCGGCTCCGGCTCTGGAACAGCCTTTACCCTG<br>AGGATCTCTCGGGTGGAGGCAGAGGACGTGGGCGTGTATTA<br>CTGCATGCAGCACCTGGAGTACCCCTTCACATTTGGCGCAGG<br>AACCAAGCTGGAGCTGAAGCGGAGCGACCCCACCACAACCC<br>CTGCACCACGGCCCCCTACACCAGCACCTACCATCGCATCTC<br>AGCCACTGAGCCTGCGGCCCGAGGCCTGTAGGCCTGCAGCA<br>GGAGGAGCAGTGCACACCAGGGGCCTGGACTTCGCCTGCGA<br>TATCTATATCTGGGCACCACTGGCAGGAACATGTGGCGTGCT<br>GCTGCTGAGCCTGGTCATCACCCTGTATTGCAAGAGAGGCA<br>GGAAGAAGCTGCTGTACATCTTCAAGCAGCCTTTTATGCGGC<br>CAGTGCAGACAACCCAGGAGGAGGATGGCTGCTCCTGTAGA<br>TTCCCAGAGGAGGAGGAGGGAGGATGTGAGCTGCGCGTGA<br>AGTTTAGCCGGTCCGCCGACGCACCAGCATATCAGCAGGGC<br>CAGAATCAGCTGTACAATGAGCTGAACCTGGGCCGGAGAGA<br>GGAGTACGACGTGCTGGATAAGAGGAGGGGAAGGGACCCC<br>GAGATGGGAGGCAAGCCACGGAGAAAGAATCCCCAGGAGG<br>GCCTGTATAACGAGCTGCAGAAGGATAAGATGGCCGAGGCC<br>TACAGCGAGATCGGCATGAAGGGAGAGAGGCGCGGGGCA<br>AGGGACACGACGGCCTGTATCAGGGCCTGTCCACAGCCACC<br>AAGGACACCTACGATGCCCTGCACATGCAGGCCCTGCCACC<br>AAGGTGA |
| 4 | anti-CD19<br>CAR_v1.3 | ATGGGAACAAGCCTGCTGTGCTGGATGGCTCTGTGCCTGCTG<br>GGGGCCGACCACGCTGACGCCTCCGGGGGGGGGGCTCTCC<br>TGCCCCTAGGCCCCCTACACCTGCACCAACCATCGCATCCCA<br>GCCACTGTCTCTGCGCCCTGAGGCCTGCCGGCCAGCAGCAG<br>GAGGAGCAGTGCACACCCGCGGCCTGGACTTCGCCTGCGAT<br>ATCTATATCTGGGCACCACTGGCAGGCACATGTGGCGTGCT<br>GCTGCTGAGCCTGGTCATCACCCTGTACTGCAATCACAGGA<br>ACCGGAGAAGGGTGTGCAAGTGTCCCCGGCCTGTGGTGAGA<br>GCAGAGGGAAGGGCAGCCTGCTGACATGTGGCGACGTGG<br>AGGAGAATCCAGGCCCTATGGAGACAGATACCCTGCTGCTG<br>TGGGTGCTGCTGCTGTGGGTGCCCGGCAGCACCGGAGAGGT<br>GCAGCTGCAGCAGTCCGGACCAGAGCTGATCAAGCCTGGAG<br>CCAGCGTGAAGATGTCCTGTAAGGCCTCTGGCTATACATTCA<br>CCAGCTACGTGATGCACTGGGTGAAGCAGAAGCCTGGCCAG<br>GGCCTGGAGTGGATCGGCTATATCAATCCATACAACGACGG<br>CACAAAGTATAACGAGAAGTTTAAGGGCAAGGCCACACTGA<br>CCTCCGATAAGAGCTCCTCTACAGCCTACATGGAGCTGAGCT<br>CCCTGACCTCTGAGGACAGCGCCGTGTACTATTGCGCCAGA<br>GGCACATACTATTACGGCTCTAGGGTGTTCGATTACTGGGGC<br>CAGGGCACCACACTGACCGTGTCTAGCGGAGGAGGAGGCAG |

TABLE 1-continued

Polynucleotide Sequences of exemplary CD19 targeting CARs

| SEQ ID NO | Description | Sequence |
|---|---|---|
| | | CGGAGGAGGAGGCTCCGGCGGCGGCGGCTCTGACATCGTGA TGACACAGGCAGCACCATCCATCCCAGTGACCCCTGGCGAG AGCGTGTCCATCTCTTGTCGGTCCTCTAAGAGCCTGCTGAAC TCCAATGGCAACACCTATCTGTACTGGTTTCTGCAGCGGCCC GGACAGAGCCCACAGCTGCTGATCTATAGGATGTCTAATCT GGCAAGCGGCGTGCCCGATCGCTTCAGCGGCTCCGGCTCTG GCACAGCCTTTACCCTGAGGATCTCCCGCGTGGAGGCAGAG GACGTGGGCGTGTATTACTGCATGCAGCACCTGGAGTACCC CTTCACATTTGGCGCAGGCACCAAGCTGGAGCTGAAGCGGA GCGACCCCACCACAACCCCTGCACCACGGCCACCCACACCA GCACCTACTATTGCATCCCAGCCACTGAGCCTGCGGCCCGA GGCCTGTAGGCCTGCCGCCGGCGGCGCAGTGCACACCCGGG GCCTGGACTTTGCCTGCGATATCTACATCTGGGCACCTCTGG CCGGCACATGCGGCGTGCTGTTACTGAGCCTGGTCATCACCC TGTATTGCAAGCGGGGCAGAAAGAAGCTGCTGTACATCTTC AAGCAGCCTTTTATGCGGCCAGTGCAGACAACCCAGGAGGA GGATGGCTGCTCCTGTAGATTCCCAGAGGAGGAGGAGGGAG GATGTGAGCTGCGCGTGAAGTTTAGCCGGTCCGCCGACGCA CCAGCATATCAGCAGGGCCAGAACCAGCTGTACAATGAGCT GAACCTGGGCCGGAGAGAGGAGTATGACGTGCTGGATAAG AGACGGGGCCGGGACCCCGAGATGGGAGGCAAGCCACGCC GGAAGAATCCCCAGGAGGGCCTGTATAACGAGCTGCAGAAG GATAAGATGGCCGAGGCCTACAGCGAGATCGGCATGAAGG GAGAGAGAAGGCGCGGCAAGGGACACGACGGCCTGTACCA GGGCCTGAGCACAGCAACAAAAGACACCTACGACGCACTGC ACATGCAGGCTCTGCCCCCTCGGTAA |
| 5 | anti-CD19 CAR_v1.4 | ATGGGAACCTCTCTGCTGTGCTGGATGGCTCTGTGCCTGCTG GGGGCCGATCACGCTGACGCAAGTGGCGGGGGGGGGTCCG AACTGCCCACACAGGGCACCTTCTCCAACGTGAGCACCAAC GTGAGCTCCGGCGGAGGAGGCAGCCCTGCACCAAGGCCCCC TACACCAGCACCTACCATCGCATCTCAGCCACTGAGCCTGCG CCCCGAGGCCTGCCGGCCTGCAGCAGGCGGCGCCGTGCACA CCCGCGGCCTGGACTTTGCCTGCGATATCTATATCTGGGCAC CTCTGGCAGGCACATGTGGCGTGCTGCTGCTGAGCCTGGTCA TCACCCTGTACTGCAATCACAGGAACCGGAGAAGGGTGTGC AAGTGTCCACGGCCCGTGGTGAGAGCAGAGGGAAGGGCTC CCTGCTGACATGTGGCGACGTGGAGGAGAATCCTGGCCCAA TGGAGACAGATACCCTGCTGCTGTGGGTGCTGCTGCTGTGG GTGCCCGGCTCCACCGGAGAGGTGCAGCTGCAGCAGTCTGG ACCAGAGCTGATCAAGCCAGGAGCATCCGTGAAGATGTCTT GTAAGGCCAGCGGCTATACATTCACCAGCTACGTGATGCAC TGGGTGAAGCAGAAGCCAGGACAGGGCCTGGAGTGGATCG GCTATATCAATCCTTACAACGACGGCACCAAGTATAACGAG AAGTTTAAGGGCAAGGCCACACTGACCTCTGATAAGTCTAG CTCCACAGCCTACATGGAGCTGTCTAGCCTGACCAGCGAGG ACTCCGCCGTGTACTATTGCGCCAGAGGCACATACTATTACG GCAGCAGGGTGTTCGATTACTGGGGCCAGGGCACCACACTG ACCGTGTCCTCTGGAGGAGGAGGCTCCGGAGGAGGAGGCTC TGGCGGCGGCGGCAGCGACATCGTGATGACACAGGCAGCAC CTTCCATCCCAGTGACCCCAGGCGAGTCTGTGAGCATCTCCT GTCGGAGCTCCAAGTCCCTGCTGAACTCTAATGGCAACACCT ATCTGTACTGGTTTCTGCAGCGGCCCGGACAGTCCCCACAGC TGCTGATCTATAGGATGAGCAATCTGGCCTCCGGCGTGCCA GATCGCTTCTCTGGCAGCGGCTCCGGCACAGCCTTTACCCTG AGGATCTCTCGCGTGGAGGCAGAGGACGTGGGCGTGTATTA CTGCATGCAGCACCTGGAGTACCCATTCACATTTGGCGCAG GCACCAAGCTGGAGCTGAAGCGGAGCGACCCCACCACAACC CCAGCACCTCGGCCACCCACACCAGCACCCACCATCGCATC TCAGCCTCTGAGCCTGCGCCCCGAGGCCTGTAGGCCCGCAG CAGGAGGAGCAGTGCACACCCGGGGCCTGGACTTCGCCTGC GATATCTACATCTGGGCACCACTGGCCGGCACATGCGGCGT GCTGTTACTGAGCCTGGTCATCACCCTGTATTGCAAGCGGGG CAGAAAGAAGCTGCTGTACATCTTCAAGCAGCCCTTTATGC GGCCTGTGCAGACAACCCAGGAGGAGGATGGCTGCTCCTGT AGATTCCCTGAGGAGGAGGAGGGAGGATGTGAGCTGCGCGT GAAGTTTTCTCGGAGCGCCGACGCACCAGCATATCAGCAGG GACAGAACCAGCTGTACAATGAGCTGAACCTGGGCCGGAGA GAGGAGTATGACGTGCTGGATAAGAGACGGGGCCGGGACC CCGAGATGGGAGGCAAGCCTCGCCGGAAGAATCCACAGGA GGGCCTGTATAACGAGCTGCAGAAGGATAAGATGGCCGAGG CCTACAGCGAGATCGGCATGAAGGGAGAGAGAAGGCGCGG CAAGGGACACGACGGCCTGTACCAGGGCCTGAGCACAGCAA CAAAAGACACCTACGACGCACTGCACATGCAGGCTCTGCCA CCAAGATGA |

TABLE 1-continued

Polynucleotide Sequences of exemplary CD19 targeting CARs

| SEQ ID NO | Description | Sequence |
| --- | --- | --- |
| 6 | anti-CD19 CAR_v1.5 | ATGGGGACCTCACTGCTGTGCTGGATGGCTCTGTGCCTGCTG GGGGCCGACCACGCTGACGCCTGCTCTGGGGGGGGGGGGG CTCATGCTCCGGAGGAGGAGGCTCTGAGCTGCCAACCCAGG GCACATTCTCCAACGTGAGCACCAACGTGTCTCCTGCCAAGC CAACCACAACCGCATGCAGCGGCGGAGGAGGAGGCAGCTG TTCCGGCGGCGGCGGCAGCCCTGCCCCAAGGCCCCCTACCC CAGCACCTACAATCGCATCTCAGCCTCTGAGCCTGCGCCCAG AGGCCTGTCGGCCCGCAGCAGGAGGAGCAGTGCACACCCGC GGCCTGGACTTTGCCTGCGATATCTATATCTGGGCACCACTG GCAGGCACCTGTGGCGTGCTGCTGCTGAGCCTGGTCATCACC CTGTACTGCAATCACAGGAACCGGAGAAGGGTGTGCAAGTG TCCACGGCCCGTGGTGAGAGCAGAGGGAAGGGGCTCTCTGC TGACCTGTGGCGACGTGGAGGAGAATCCTGGCCCTATGGAG ACAGATACACTGCTGCTGTGGGTGCTGCTGCTGTGGGTGCCC GGCAGCACAGGAGAGGTGCAGCTGCAGCAGTCCGGACCTGA GCTGATCAAGCCAGGCGCCTCCGTGAAGATGTCTTGCAAGG CCAGCGGCTATACCTTCACAAGCTACGTGATGCACTGGGTG AAGCAGAAGCCAGGCCAGGGCCTGGAGTGGATCGGCTATAT CAATCCCTACAACGACGGCACCAAGTATAACGAGAAGTTTA AGGGCAAGGCCACCCTGACAAGCGATAAGAGCTCCTCTACC GCCTACATGGAGCTGAGCTCCCTGACAAGCGAGGACTCCGC CGTGTACTATTGCGCCAGAGGCACCTACTATTACGGCTCCAG GGTGTTCGATTACTGGGGCCAGGGCACAACCCTGACAGTGT CTAGCGGAGGAGGAGGCAGCGGAGGAGGAGGCTCCGGCGG CGGCGGCTCTGACATCGTGATGACCCAGGCAGCACCATCCA TCCCTGTGACACCAGGCGAGTCTGTGAGCATCTCCTGTCGGT CCTCTAAGTCCCTGCTGAACTCTAATGGCAACACCTATCTGT ACTGGTTTCTGCAGCGGCCCGGACAGTCTCCTCAGCTGCTGA TCTATAGGATGAGCAATCTGGCCTCCGGCGTGCCTGATCGCT TCTCTGGCAGCGGCTCCGGCACCGCCTTTACACTGAGGATCA GCCGCGTGGAGGCAGAGGACGTGGGCGTGTATTACTGCATG CAGCACCTGGAGTACCCTTTCACCTTTGGCGCCGGCACAAA GCTGGAGCTGAAGCGGAGCGACCCCACAACCACACCAGCAC CTCGGCCACCCACCCCAGCACCAACAATCGCATCTCAGCCA CTGAGCCTGCGGCCCGAGGCCTGTAGGCCAGCCGCCGGCGG CGCAGTGCACACCCGGGGCCTGGACTTCGCCTGCGATATCT ACATCTGGGCCCCTCTGGCCGGCACCTGCGGCGTGCTGTTAC TGAGCCTGGTCATCACCCTGTATTGCAAGCGGGGCAGAAAG AAGCTGCTGTACATCTTCAAGCAGCCCTTCATGCGGCCCGTG CAGACCACACAGGAGGAGGATGGCTGCTCCTGTAGATTCCC AGAGGAGGAGGAGGGAGGATGTGAGCTGCGCGTGAAGTTTT CTCGGAGCGCCGACGCACCTGCATATCAGCAGGGACAGAAC CAGCTGTACAATGAGCTGAACCTGGGCCGGAGAGAGGAGTA TGACGTGCTGGATAAGAGACGGGGCCGGGACCCCGAGATGG GAGGCAAGCCCCGCCGGAAGAATCCTCAGGAGGGCCTGTAT AACGAGCTGCAGAAGGATAAGATGGCCGAGGCCTACAGCG AGATCGGCATGAAGGGAGAGAGAAGGCGCGGCAAGGGCCA CGACGGCCTGTACCAGGGCCTGTCCACAGCAACAAAGGATA CTTATGACGCTCTGCACATGCAGGCTCTGCCCCCTCGGTGA |
| 7 | anti-CD19 CAR_v1.6 | ATGGGAACCAGCCTGCTGTGCTGGATGGCACTGTGCCTGCT GGGGAGCAGACCACGCCGATGCCGAACTGCCTACTCAGGGA CATTCTCTAATGTGAGCACCAACGTGAGCTCTGGAGGAGGA GGCTCCGAGCTGCCAACCCAGGGCACATTCTCTAATGTGAG CACAAACGTGTCTCCCGCCAAGCCTACCACAACCGCCGAAC TGCCTACCCAGGGCACATTTTCCAACGTGTCTACCAACGTGT CTAGCGGAGGAGGAGGCTCCCCCGCACCTAGGCCCCCTACC CCAGCACCAACAATCGCAAGCCAGCCTCTGTCCCTGCGCCC AGAGGCATGCAGGCCAGCAGCAGGAGGAGCAGTGCACACC CGCGGCCTGGACTTTGCCTGCGATATCTATATCTGGGCACCA CTGGCAGGAACCTGTGGCGTGCTGCTGCTGTCTCTGGTCATC ACCCTGTACTGCAATCACAGAAACCGGAGAAGGGTGTGCAA GTGTCCTCGCCAGTGGTGAGAGCAGAGGGAAGGGGCAGCC TGCTGACCTGTGGCGACGTGGAGGAGAATCCCGGCCCTATG GAGACAGATACACTGCTGCTGTGGGTGCTGCTGCTGTGGGT GCCAGGCTCTACAGGAGAGGTGCAGCTGCAGCAGAGCGGAC CTGAGCTGATCAAGCCAGGCGCCTCTGTGAAGATGAGCTGC AAGGCCTCCGGCTATACCTTCACAAGCTACGTGATGCACTG GGTGAAGCAGAAGCCAGGCCAGGGCCTGGAGTGGATCGGCT ATATCAATCCCTACAACGACGGCACCAAGTATAACGAGAAG TTTAAGGGCAAGGCCACCCTGACATCCGATAAGAGCTCCTC TACCGCCTACATGGAGCTGAGCTCCCTGACATCCGAGGACT CTGCCGTGTACTATTGCGCCAGAGGCACCTACTATTACGGCT CTAGGGTGTTCGATTACTGGGGCCAGGGCACAACCCTGACA |

TABLE 1-continued

Polynucleotide Sequences of exemplary CD19 targeting CARs

| SEQ ID NO | Description | Sequence |
|---|---|---|
| | | GTGTCTAGCGGAGGAGGAGGCTCTGGAGGAGGAGGCAGCG<br>GCGGCGGAGGCTCCGACATCGTGATGACCCAGGCAGCACCA<br>TCCATCCCAGTGACACCTGGCGAGAGCGTGTCCATCTCTTGT<br>AGGTCCTCTAAGTCTCTGCTGAACAGCAATGGCAACACCTAT<br>CTGTACTGGTTTCTGCAGCGGCCCGGACAGAGCCCTCAGCTG<br>CTGATCTATAGGATGTCCAATCTGGCCTCTGGAGTGCCTGAT<br>CGCTTCAGCGGCTCCGGCTCTGGAACCGCCTTTACACTGAGG<br>ATCTCCCGCGTGGAGGCAGAGGACGTGGGCGTGTATTACTG<br>CATGCAGCACCTGGAGTACCCTTTCACCTTTGGCGCCGGCAC<br>AAAGCTGGAGCTGAAGCGGAGCGACCCCACAACCACACCA<br>GCACCCCGGCCACCAACCCCTGCCCCTACAATCGCAAGCCA<br>GCCACTGTCCCTGCGGCCCGAGGCCTGTAGACCTGCCGCCG<br>GCGGCGCCGTCCATACCCGCGGCCTGGATTTCGCCTGCGATA<br>TCTACATTTGGGCCCCTCTGGCCGGCACTTGCGGCGTGCTGC<br>TGCTGAGCCTGGTCATCACCCTGTATTGCAAGCGGGGCAGA<br>AAGAAGCTGCTGTACATCTTCAAGCAGCCCTTCATGCGGCCC<br>GTGCAGACCACACAGGAGGAGGATGGCTGCTCCTGTAGATT<br>CCCAGAGGAGGAGGAGGGAGGATGTGAGCTGCGCGTGAAG<br>TTTAGCCGGTCCGCCGACGCACCTGCATATCAGCAGGGCCA<br>GAACCAGCTGTACAATGAGCTGAACCTGGGCCGGAGAGAGG<br>AGTACGACGTGCTGGATAAGAGAAGGGGACGGGACCCCGA<br>GATGGGAGGCAAGCCCCGCCGGAAGAATCCTCAGGAGGGC<br>CTGTATAACGAGCTGCAGAAGGATAAGATGGCCGAGGCCTA<br>CAGCGAGATCGGCATGAAGGGAGAGAGAAGGCGCGGCAAG<br>GGACACGACGGCCTGTATCAGGGCCTGTCCACCGCCACAAA<br>GGACACCTACGATGCCCTGCACATGCAGGCCCTGCCTCCAA<br>GATGA | b. Safety Switches and Monoclonal Antibody Specific-Epitopes

Safety Switches

It will be appreciated that adverse events may be minimized by transducing the immune cells (containing one or more CARs) with a suicide gene other than a rituximab-binding epitope. It may also be desired to incorporate an inducible "on" or "accelerator" switch into the immune cells. Suitable techniques include use of inducible caspase-9 (U.S. Appl. 2011/0286980) or a thymidine kinase, before, after or at the same time, as the cells are transduced with the CAR construct of the present disclosure. Additional methods for introducing suicide genes and/or "on" switches include TALENS, zinc fingers, RNAi, siRNA, shRNA, antisense technology, and other techniques known in the art.

In accordance with the disclosure, additional on-off or other types of control switch techniques may be incorporated herein. These techniques may employ the use of dimerization domains and optional activators of such domain dimerization. These techniques include, e.g., those described by Wu et al., Science 2014 350 (6258) utilizing FKBP/Rapalog dimerization systems in certain cells, the contents of which are incorporated by reference herein in their entirety. Additional dimerization technology is described in, e.g., Fegan et al. Chem. Rev. 2010, 110, 3315-3336 as well as U.S. Pat. Nos. 5,830,462; 5,834,266; 5,869,337; and 6,165,787, the contents of which are also incorporated by reference herein in their entirety. Additional dimerization pairs may include cyclosporine-A/cyclophilin, receptor, estrogen/estrogen receptor (optionally using tamoxifen), glucocorticoids/glucocorticoid receptor, tetracycline/tetracycline receptor, vitamin D/vitamin D receptor. Further examples of dimerization technology can be found in e.g., WO 2014/127261, WO 2015/090229, US 2014/0286987, US2015/0266973, US2016/0046700, U.S. Pat. No. 8,486,693, US 2014/0171649, and US 2012/0130076, the contents of which are further incorporated by reference herein in their entirety.

In some embodiments, the CAR-immune cell (e.g., CAR-T cell) of the disclosure comprises a polynucleotide encoding a suicide polypeptide that is deficient in rituximab binding. In some embodiments, the suicide peptide comprises a mutated RQR8 sequence. See, e.g., WO2013153391A, which is hereby incorporated by reference in its entirety. In CAR-immune cell (e.g., CAR-T cell) cells comprising the polynucleotide, the suicide polypeptide is expressed at the surface of a CAR-immune cell (e.g., CAR-T cell). In some embodiments, the suicide polypeptide comprises the amino acid sequence shown in SEQ ID NO: 19.

(SEQ ID NO: 19)
CPYSNPSLCSGGGGSELPTQGTFSNVSTNVSPAKPTTTACPYSNPSLCSG
GGGSPAPRPPTPAPTIASQPLSLRPEACRPAAGGAVHTRGLDFACDIYIW
APLAGTCGVLLLSLVITLYCNHRNRRRVCKCPRPVV.

The suicide polypeptide may also comprise a signal peptide at the amino terminus—for example, MGTSLLCW-MALCLLGADHADA (SEQ ID NO: 20). In some embodiments, the suicide polypeptide comprises the amino acid sequence shown in SEQ ID NO: 21, which includes the signal sequence of SEQ ID NO: 20.

(SEQ ID NO: 21)
MGTSLLCWMALCLLGADHADACPYSNPSLCSGGGGSELPTQGTFSNVSTN

VSPAKPTTTACPYSNPSLCSGGGGSPAPRPPTPAPTIASQPLSLRPEACR

PAAGGAVHTRGLDFACDIYIWAPLAGTCGVLLLSLVITLYCNHRNRRRVC

KCPRPVV.

In certain embodiments, the suicide peptide comprises an amino acid sequence that comprises a one or more mutated residues, inserted residues, or deleted residues that reduce or eliminate rituximab binding.

When the suicide polypeptide is expressed at the surface of a CAR-immune cell (e.g., CAR-T cell), antibody binding to the suicide gene epitopes of the polypeptide causes lysis of the cell. Deletion of CD19-specific CAR-immune cell (e.g., CAR-T cell) may occur in vivo, for example by administering a suicide agent to a patient. The decision to delete the transferred cells may arise from undesirable effects being detected in the patient which are attributable to the transferred cells, such as for example, when unacceptable levels of toxicity are detected. As used herein, a "suicide agent" refers to a molecule that binds to the CAR immune cell and causes lysis of the CAR expressing immune cell.

In some embodiments, a suicide polypeptide is expressed on the surface of the cell. In some embodiments, a suicide polypeptide is included in the CAR construct. In some embodiments, a suicide polypeptide is not part of the CD19 CAR construct.

In some embodiments, the extracellular domain of any one of the CD19-specific CARs disclosed herein may comprise one or more epitopes specific for (i.e., specifically recognized by) a monoclonal antibody. These epitopes are also referred to herein as mAb-specific epitopes. Exemplary mAb-specific epitopes are disclosed in International Patent Publication No. WO 2016/120216, which is incorporated herein in its entirety. In these embodiments, the extracellular domain of the CARs comprise antigen binding domains that specifically bind to CD19 and one or more epitopes that bind to one or more monoclonal antibodies (mAbs). CARs comprising the mAb-specific epitopes can be single-chain or multi-chain.

The inclusion of epitopes specific for monoclonal antibodies in the extracellular domain of the CARs described herein allows sorting and depletion of engineered immune cells expressing the CARs. In some embodiments, this feature also promotes recovery of endogenous CD19-expressing cells that were depleted by administration of engineered immune cells expressing the CARs. In some embodiments, allowing for depletion provides a safety switch in case of deleterious effects, e.g., upon administration to a subject.

Accordingly, in some embodiments, the present disclosure relates to a method for sorting and/or depleting the engineered immune cells endowed with the CARs comprising mAb-specific epitopes and a method for promoting recovery of endogenous CD19-expressing cells.

Several epitope-monoclonal antibody couples can be used to generate CARs comprising monoclonal antibody specific epitopes; in particular, those already approved for medical use or for use in GMP manufacturing, such as CD34 epitope/QBEND-10 as a non-limiting example.

The disclosure also encompasses methods for sorting the engineered immune cells endowed with the CD19-specific CARs expressing the mAb-specific epitope(s) and therapeutic methods where the activation of the engineered immune cells endowed with these CARs is modulated by depleting the cells using an antibody that targets the external ligand binding domain of said CARs. Table 2 provides exemplary mimotope sequences that can be inserted into the extracellular domains of the CARs of the disclosure.

TABLE 2

Exemplary mimotope sequences

| Rituximab | | |
|---|---|---|
| Mimotope | SEQ ID NO: 22 | CPYSNPSLC |
| Palivizumab | | |
| Epitope | SEQ ID NO: 23 | NSELLSLINDMPITNDQKKLMSNN |
| Cetuximab | | |
| Mimotope 1 | SEQ ID NO: 24 | CQFDLSTRRLKC |
| Mimotope 2 | SEQ ID NO: 25 | CQYNLSSRALKC |
| Mimotope 3 | SEQ ID NO: 26 | CVWQRWQKSYVC |
| Mimotope 4 | SEQ ID NO: 27 | CMWDRFSRWYKC |
| Nivolumab | | |
| Epitope 1 | SEQ ID NO: 28 | SFVLNWYRMSPSNQTDKLAAFPEDR |
| Epitope 2 | SEQ ID NO: 29 | SGTYLCGAISLAPKAQIKE |
| QBEND-10 | | |
| Epitope | SEQ ID NO: 30 | ELPTQGTFSNVSTNVS |
| Alemtuzumab | | |
| Epitope | SEQ ID NO: 31 | GQNDTSQTSSPS |

In certain embodiments, the CAR comprises an epitope or mimotope amino acid sequence that is at least about 75%, at least about 80%, at least about 85%, at least about 90%, at least about 95%, at least about 96%, at least about 97%, at least about 98%, at least about 99%, or 100% identical to the epitope or mimotope amino acid sequences set forth herein in Table 2. In certain embodiments, the CAR comprises an epitope or mimotope amino acid sequence that is not or does not comprise SEQ ID NO: 22. In certain embodiments, the CAR comprises an epitope or mimotope comprising the amino acid sequence of SEQ ID NO: 30.

c. Hinge Domain

The extracellular domain of the CARs of the disclosure may comprise a "hinge" domain (or hinge region). The term generally to any polypeptide that functions to link the transmembrane domain in a CAR to the extracellular antigen binding domain in a CAR. In particular, hinge domains can be used to provide more flexibility and accessibility for the extracellular antigen binding domain.

A hinge domain may comprise up to 300 amino acids—in some embodiments 10 to 100 amino acids or in some embodiments 25 to 50 amino acids. The hinge domain may be derived from all or part of naturally occurring molecules, such as from all or part of the extracellular region of CD8, CD4, CD28, 4-1BB, or IgG (in particular, the hinge region of an IgG; it will be appreciated that the hinge region may contain some or all of a member of the immunoglobulin family such as IgG1, IgG2, IgG3, IgG4, IgA, IgD, IgE, IgM, or fragment thereof), or from all or part of an antibody heavy-chain constant region. Alternatively, the hinge domain may be a synthetic sequence that corresponds to a naturally occurring hinge sequence, or may be an entirely synthetic hinge sequence. In some embodiments said hinge domain is a part of human CD8α chain (e.g., NP_001139345.1). In another particular embodiment, said hinge and transmembrane domains comprise a part of human CD8α chain. In some embodiments, the hinge domain of CARs described herein comprises a subsequence of CD8a, an IgG1, IgG4, PD-1 or an FcγRIIIα, in particular the hinge region of any of an CD8α, an IgG1, IgG4, PD-1 or an FcγRIIIα. In some embodiments, the hinge domain comprises a human CD8α hinge, a human IgG1 hinge, a human IgG4, a human PD-1 or a human FcγRIIIα hinge. In some embodiments the CARs disclosed herein comprise a scFv, CD8α human hinge and transmembrane domains, the CD3ζ signaling domain, and 4-1BB signaling domain. Table 3 provides amino acid sequences for exemplary hinges provided herein.

transmembrane, and intracellular domains of the CAR. In some embodiments, the linker comprises a glycine repeat sequence. In some embodiments, the linker comprises (GGGGS)n, wherein n is 1, 2, 3, 4, or 5 (SEQ ID NO: 41).

Suitable transmembrane domains for a CAR disclosed herein have the ability to (a) be expressed at the surface an immune cell such as, for example without limitation, a lymphocyte cell, such as a T helper ($T_h$) cell, cytotoxic T ($T_a$) cell, T regulatory ($T_{reg}$) cell, or Natural killer (NK) cells, and/or (b) interact with the extracellular antigen binding domain and intracellular signaling domain for directing the cellular response of an immune cell against a target cell.

The transmembrane domain may be derived either from a natural or from a synthetic source. Where the source is natural, the domain may be derived from any membrane-bound or transmembrane protein.

Transmembrane regions of particular use in this disclosure may be derived from (comprise, or correspond to) CD28, OX-40, 4-1BB/CD137, CD2, CD7, CD27, CD30, CD40, programmed death-1 (PD-1), inducible T cell costimulator (ICOS), lymphocyte function-associated antigen-1 (LFA-1, CD1-1a/CD18), CD3 gamma, CD3 delta, CD3 epsilon, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptors, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta,

TABLE 3

Exemplary hinges

| Domain | Amino Acid Sequence | SEQ ID NO: |
|---|---|---|
| FcγRIIIα hinge | GLAVSTISSFFPPGYQ | 32 |
| CD8α hinge | TTTPAPRPPTPAPTIASQPLSLRPEACRPAAGGAVHTRGLDFACD | 33 |
| IgG1 hinge | EPKSPDKTHTCPPCPAPPVAGPSVFLFPPKPKDTLMIARTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 34 |

In certain embodiments, the hinge region comprises an amino acid sequence that is at least about 75%, at least about 80%, at least about 85%, at least about 90%, at least about 95%, at least about 96%, at least about 97%, at least about 98%, at least about 99%, or 100% identical to the hinge domain amino acid sequences set forth herein in Table 3.

d. Transmembrane Domain

The CARs of the disclosure are designed with a transmembrane domain that is fused to the extracellular domain of the CAR. It can similarly be fused to the intracellular domain of the CAR. In some instances, the transmembrane domain can be selected or modified by amino acid substitution to avoid binding of such domains to the transmembrane domains of the same or different surface membrane proteins to minimize interactions with other members of the receptor complex. In some embodiments, short linkers may form linkages between any or some of the extracellular, IL-2R beta, IL-2R gamma, IL-7R alpha, ITGA4, VLA1, CD49a, ITGA4, IA4, CD49D, ITGA6, VLA-6, CD49f, ITGAD, CD1 1d, ITGAE, CD103, ITGAL, CD1 1a, LFA-1, ITGAM, CD1 1b, ITGAX, CD1 1c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof.

As non-limiting examples, the transmembrane region can be a derived from, or be a portion of a T cell receptor such as α, β, γ or δ, polypeptide constituting CD3 complex, IL-2 receptor p55 (α chain), p75 (β chain) or γ chain, subunit chain of Fc receptors, in particular Fcγ receptor III or CD proteins. Alternatively, the transmembrane domain can be synthetic and can comprise predominantly hydrophobic residues such as leucine and valine. In some embodiments said transmembrane domain is derived from the human CD8α chain (e.g., NP_001139345.1).

In some embodiments, the transmembrane domain in the CAR of the disclosure is a CD8α transmembrane domain. In some embodiments, the transmembrane domain in the CAR of the disclosure is a CD8α transmembrane domain comprising the amino acid sequence IYIWAPLAGTCGVLLLSLVIT (SEQ ID NO: 35). In some embodiments, the CD8α transmembrane domain comprises the nucleic acid sequence that encodes the transmembrane amino acid sequence of SEQ ID NO: 35. In some embodiments, the hinge and transmembrane domain in the CAR of the disclosure is a CD8α hinge and transmembrane domain comprising the amino acid sequence (SEQ ID NO: 36)
TTTPAPRPPTPAPTIASQPLSLRPEACRPAAGGAVHTRGLDFACDIYIWA
PLAGTCGVLLLSLVIT.

e. Intracellular Domain

The intracellular (cytoplasmic) domain of the CARs of the disclosure can provide activation of at least one of the normal effector functions of the immune cell comprising the CAR. Effector function of a T cell, for example, may refer to cytolytic activity or helper activity, including the secretion of cytokines.

In some embodiments, an activating intracellular signaling domain for use in a CAR can be the cytoplasmic sequences of, for example without limitation, the T cell receptor and co-receptors that act in concert to initiate signal transduction following antigen receptor engagement, as well as any derivative or variant of these sequences and any synthetic sequence that has the same functional capability.

It will be appreciated that suitable (e.g., activating) intracellular domains include, but are not limited to signaling domains derived from (or corresponding to) CD28, OX-40, 4-1BB/CD137, CD2, CD7, CD27, CD30, CD40, programmed death-1 (PD-1), inducible T cell costimulator (ICOS), lymphocyte function-associated antigen-1 (LFA-1, CD1-1a/CD18), CD3 gamma, CD3 delta, CD3 epsilon, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptors, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD1 1d, ITGAE, CD103, ITGAL, CD1 1a, LFA-1, ITGAM, CD1-1b, ITGAX, CD1 1c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof.

The intracellular domains of the CARs of the disclosure may incorporate, in addition to the activating domains described above, co-stimulatory signaling domains (interchangeably referred to herein as costimulatory molecules) to increase their potency. Costimulatory domains can provide a signal in addition to the primary signal provided by an activating molecule as described herein.

It will be appreciated that suitable costimulatory domains within the scope of the disclosure can be derived from (or correspond to) for example, CD28, OX40, 4-1BB/CD137, CD2, CD3 (alpha, beta, delta, epsilon, gamma, zeta), CD4, CD5, CD7, CD9, CD16, CD22, CD27, CD30, CD 33, CD37, CD40, CD 45, CD64, CD80, CD86, CD134, CD137, CD154, PD-1, ICOS, lymphocyte function-associated antigen-1 (LFA-1 (CD1 1a/CD18), CD247, CD276 (B7-H3), LIGHT (tumor necrosis factor superfamily member 14; TNFSF14), NKG2C, Ig alpha (CD79a), DAP-10, Fc gamma receptor, MHC class I molecule, TNFR, integrin, signaling lymphocytic activation molecule, BTLA, Toll ligand receptors, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD1-1d, ITGAE, CD103, ITGAL, CD1-1a, LFA-1, ITGAM, CD1-1b, ITGAX, CD1-1c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, CD83 ligand, or fragments or combinations thereof. It will be appreciated that additional costimulatory molecules, or fragments thereof, not listed above are within the scope of the disclosure.

In some embodiments, the intracellular/cytoplasmic domain of the CAR can be designed to comprise the 41BB/CD137 domain by itself or combined with any other desired intracellular domain(s) useful in the context of the CAR of the disclosure. The complete native amino acid sequence of 41BB/CD137 is described in NCBI Reference Sequence: NP_001552.2. The complete native 41BB/CD137 nucleic acid sequence is described in NCBI Reference Sequence: NM_001561.5.

In some embodiments, the intracellular/cytoplasmic domain of the CAR can be designed to comprise the CD28 domain by itself or combined with any other desired intracellular domain(s) useful in the context of the CAR of the disclosure. The complete native amino acid sequence of CD28 is described in NCBI Reference Sequence: NP_006130.1. The complete native CD28 nucleic acid sequence is described in NCBI Reference Sequence: NM_006139.1.

In some embodiments, the intracellular/cytoplasmic domain of the CAR can be designed to comprise the CD3 zeta domain by itself or combined with any other desired intracellular domain(s) useful in the context of the CAR of the disclosure. In some embodiments, the intracellular signaling domain of the CAR can comprise the CD3 signaling domain which has amino acid sequence with at least about 70%, at least 80%, at least 90%, 95%, 97%, or 99% sequence identity with an amino acid sequence shown in SEQ ID NO: 38. For example, the intracellular domain of the CAR can comprise a CD3 zeta chain portion and a portion of a costimulatory signaling molecule. The intracellular signaling sequences within the intracellular signaling portion of the CAR of the disclosure may be linked to each other in a random or specified order. In some embodiments, the intracellular domain is designed to comprise the activating domain of CD3 zeta and a signaling domain of CD28.

In some embodiments, the intracellular domain is designed to comprise the activating domain of CD3 zeta and a signaling domain of 4-1BB. In some embodiments, the 4-1BB (intracellular domain) comprises the amino acid sequence (SEQ ID NO: 37)
KRGRKKLLYIFKQPFMRPVQTTQEEDGCSCRFPEEEEGGCEL.

The CD3 zeta amino acid sequence may comprise SEQ ID NO: 38.

(SEQ ID NO: 38)
LRVKFSRSADAPAYQQGQNQLYNELNLGRREEYDVLDKRRGRDPEMGGKP
RRKNPQEGLYNELQKDKMAEAYSEIGMKGERRRGKGHDGLYQGLSTATKD
TYDALHMQALPPR.

In some embodiments the intracellular signaling domain of the CAR of the disclosure comprises a domain of a co-stimulatory molecule. In some embodiments, the intracellular signaling domain of a CAR of the disclosure comprises a part of co-stimulatory molecule selected from the group consisting of fragment of 41BB (GenBank: AAA53133.) and CD28 (NP_006130.1). In some embodiments, the intracellular signaling domain of the CAR of the disclosure comprises amino acid sequence which comprises at least 70%, at least 80%, at least 90%, 95%, 97%, or 99% sequence identity with an amino acid sequence shown in SEQ ID NO: 37 and SEQ ID NO: 38. In some embodiments, the intracellular signaling domain of the CAR of the disclosure comprises amino acid sequence which comprises at least 70%, at least 80%, at least 90%, 95%, 97%, or 99% sequence identity with an amino acid sequence shown in SEQ ID NO: 37 and/or at least 70%, at least 80%, at least 90%, 95%, 97%, or 99% sequence identity with an amino acid sequence shown in SEQ ID NO: 38.

In exemplary embodiments, a CAR of the disclosure comprises, from N-terminus to C-terminus: a CD8α signal sequence, a CD19 scFv, a CD8α hinge and transmembrane region, a 41BB cytoplasmic signaling domain, and a CD3ζ cytoplasmic signaling domain.

III. Immune Cells Comprising CARs
a. Immune Cells

Provided herein are engineered immune cells expressing the CARs of the disclosure (e.g., CAR-T cells).

In some embodiments, an engineered immune cell comprises a population of CARs, each CAR comprising different extracellular antigen-binding domains. In some embodiments, an immune cell comprises a population of CARs, each CAR comprising the same extracellular antigen-binding domains.

The engineered immune cells can be allogeneic or autologous.

In some embodiments, the engineered immune cell is a T cell (e.g., inflammatory T-lymphocyte cytotoxic T-lymphocyte, regulatory T-lymphocyte, helper T-lymphocyte, tumor infiltrating lymphocyte (TIL)), NK cell, NK-T-cell, TCR-expressing cell, dendritic cell, killer dendritic cell, a mast cell, or a B-cell. In some embodiments, the cell can be derived from the group consisting of CD4+ T-lymphocytes and CD8+ T-lymphocytes. In some exemplary embodiments, the engineered immune cell is a T cell. In some exemplary embodiments, the engineered immune cell is a gamma delta T cell. In some exemplary embodiments, the engineered immune cell is a macrophage.

In some embodiments, the engineered immune cell can be derived from, for example without limitation, a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells.

In some embodiments, the cell is obtained or prepared from peripheral blood. In some embodiments, the cell is obtained or prepared from peripheral blood mononuclear cells (PBMCs). In some embodiments, the cell is obtained or prepared from bone marrow. In some embodiments, the cell is obtained or prepared from umbilical cord blood. In some embodiments, the cell is a human cell. In some embodiments, the cell is transfected or transduced by the nucleic acid vector using a method selected from the group consisting of electroporation, sonoporation, biolistics (e.g., Gene Gun), lipid transfection, polymer transfection, nanoparticles, viral transfection (e.g., retrovirus, lentivirus, AAV) or polyplexes.

In some embodiments, the engineered immune cells expressing at their cell surface membrane a CD19-specific CAR of the disclosure comprise a percentage of stem cell memory and central memory cells greater than 10%, 20%, 30%, 40%, 50%, 60%, 70%, 80%, 90%, or 100%. In some embodiments, the engineered immune cells expressing at their cell surface membrane a CD19-specific CAR of the disclosure comprise a percentage of stem cell memory and central memory cells of about 10% to about 100%, about 10% to about 90%, about 10% to about 80%, about 10% to about 70%, about 10% to about 60%, about 10% to about 50%, about 10% to about 40%, about 10% to about 30%, about 10% to about 20%, about 15% to about 100%, about 15% to about 90%, about 15% to about 80%, about 15% to about 70%, about 15% to about 60%, about 15% to about 50%, about 15% to about 40%, about 15% to about 30%, about 20% to about 100%, about 20% to about 90%, about 20% to about 80%, about 20% to about 70%, about 20% to about 60%, about 20% to about 50%, about 20% to about 40%, about 20% to about 30%, about 30% to about 100%, about 30% to about 90%, about 30% to about 80%, about 30% to about 70%, about 30% to about 60%, about 30% to about 50%, about 30% to about 40%, about 40% to about 100%, about 40% to about 90%, about 40% to about 80%, about 40% to about 70%, about 40% to about 60%, about 40% to about 50%, about 50% to about 100%, about 50% to about 90%, about 50% to about 80%, about 50% to about 70%, about 50% to about 60%, about 60% to about 100%, about 60% to about 90%, about 60% to about 80%, about 60% to about 70%, about 70% to about 90%, about 70% to about 80%, about 80% to about 100%, about 80% to about 90%, about 90% to about 100%, about 25% to about 50%, about 75% to about 100%, or about 50% to about 75%.

In some embodiments, the immune cell is an inflammatory T-lymphocyte that expresses any one of the CARs described herein. In some embodiments, the immune cell is a cytotoxic T-lymphocyte that expresses any one of the CARs described herein. In some embodiments, the immune cell is a regulatory T-lymphocyte that expresses any one of the CARs described herein. In some embodiments, the immune cell is a helper T-lymphocyte that expresses any one of the CARs described herein.

Prior to expansion and genetic modification, a source of cells can be obtained from a subject through a variety of non-limiting methods. Cells can be obtained from a number of non-limiting sources, including peripheral blood mononuclear cells, bone marrow, lymph node tissue, cord blood, thymus tissue, stem cell- or iPSC-derived T cells or NK cells, tissue from a site of infection, ascites, pleural effusion, spleen tissue, and tumors. In some embodiments, any number of T cell lines available and known to those skilled in the art, may be used. In some embodiments, cells can be derived from a healthy donor, from a patient diagnosed with cancer or from a patient diagnosed with an infection. In some embodiments, cells can be part of a mixed population of cells which present different phenotypic characteristics.

Also provided herein are cell lines obtained from a transformed immune cell (e.g., T-cell) according to any of the above-described methods. Also provided herein are modified cells resistant to an immunosuppressive treatment. In some embodiments, an isolated cell according to the disclosure comprises a polynucleotide encoding a CAR.

The immune cells of the disclosure can be activated and expanded, either prior to or after genetic modification of the immune cells, using methods as generally known. Generally, the engineered immune cells of the disclosure can be expanded, for example, by contacting with an agent that stimulates a CD3 TCR complex and a co-stimulatory molecule on the surface of the T-cells to create an activation signal for the T cell. For example, chemicals such as calcium ionophore A23187, phorbol 12-myristate 13-acetate (PMA), or mitogenic lectins like phytohemagglutinin (PHA) can be used to create an activation signal for the T cell.

In some embodiments, T cell populations may be stimulated in vitro by contact with, for example, an anti-CD3 antibody, or antigen-binding fragment thereof, or an anti-CD28 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. The anti-CD3 antibody and an anti-CD28 antibody can be disposed on a bead or plate or other substrate. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-2, IL-15, TGFbeta, and TNF, or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, A1M-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells (e.g., IL-7 and/or IL-15). Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$). T cells that have been exposed to varied stimulation times may exhibit different characteristics In some embodiments, the cells of the disclosure can be expanded by co-culturing with tissue or cells. The cells can also be expanded in vivo, for example in the subject's blood after administering the cell into the subject.

In some embodiments, an engineered immune cell according to the present disclosure may comprise one or more disrupted or inactivated genes. In some embodiments, an engineered immune cell according to the present disclosure comprises one disrupted or inactivated gene selected from the group consisting of CD52, CD19, GR, PD-1, CTLA-4, LAG3, TIM3, BTLA, BY55, TIGIT, B7H5, LAIR1, SIGLEC10, 2B4, HLA, TCRα and TCRβ and/or expresses a CAR, a multi-chain CAR and/or a pTα transgene. In some embodiments, an isolated cell comprises polynucleotides encoding polypeptides comprising a multi-chain CAR. In some embodiments, the isolated cell according to the present disclosure comprises two disrupted or inactivated genes selected from the group consisting of: CD52 and GR, CD52 and TCRα, CDR52 and TCRβ, CD19 and CD52, CD19 and TCRα, CD19 and TCRβ, GR and TCRα, GR and TCRβ, TCRα and TCRβ, PD-1 and TCRα, PD-1 and TCRβ, CTLA-4 and TCRα, CTLA-4 and TCRβ, LAG3 and TCRα, LAG3 and TCRβ, TIM3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ and/or expresses a CAR, a multi-chain CAR and a pTα transgene. In some embodiments the method comprises disrupting or inactivating one or more genes by introducing into the cells an endonuclease able to selectively inactivate a gene by selective DNA cleavage. In some embodiments the endonuclease can be, for example, a zinc finger nuclease (ZFN), megaTAL nuclease, meganuclease, transcription activator-like effector nuclease (TALE-nuclease), or CRIPR (e.g., Cas9) endonuclease.

In some embodiments, TCR is rendered not functional in the cells according to the disclosure by disrupting or inactivating TCRα gene and/or TCRβ gene(s). In some embodiments, a method to obtain modified cells derived from an individual is provided, wherein the cells can proliferate independently of the major histocompatibility complex (MHC) signaling pathway. Modified cells, which can proliferate independently of the MHC signaling pathway, susceptible to be obtained by this method are encompassed in the scope of the present disclosure. Modified cells disclosed herein can be used in for treating patients in need thereof against Host versus Graft (HvG) rejection and Graft versus Host Disease (GvHD); therefore in the scope of the present disclosure is a method of treating patients in need thereof against Host versus Graft (HvG) rejection and Graft versus Host Disease (GvHD) comprising treating said patient by administering to said patient an effective amount of modified cells comprising disrupted or inactivated TCRα and/or TCRβ genes.

In some embodiments, the immune cells are engineered to be resistant to one or more chemotherapy drugs. The chemotherapy drug can be, for example, a purine nucleotide analogue (PNA), thus making the immune cell suitable for cancer treatment combining adoptive immunotherapy and chemotherapy. Exemplary PNAs include, for example, clofarabine, fludarabine, cyclophosphamide, and cytarabine, alone or in combination. PNAs are metabolized by deoxycytidine kinase (dCK) into mono-, di-, and tri-phosphate PNA. Their tri-phosphate forms compete with ATP for DNA synthesis, act as pro-apoptotic agents, and are potent inhibitors of ribonucleotide reductase (RNR), which is involved in trinucleotide production. Provided herein are CD19-specific CAR-T cells comprising a disrupted or inactivated dCK gene. In some embodiments, the dCK knockout cells are made by transfection of T cells using polynucleotides encoding specific TAL-nulcease directed against dCK genes by, for example, electroporation of mRNA. The dCK knockout CD19-specific CAR-T cells are resistant to PNAs, including for example clorofarabine and/or fludarabine, and maintain T cell cytotoxic activity toward CD19-expressing cells.

In some embodiments, isolated cells or cell lines of the disclosure can comprise a pTα or a functional variant thereof. In some embodiments, an isolated cell or cell line can be further genetically modified by disrupting or inactivating the TCRα gene.

The disclosure also provides engineered immune cells comprising any of the CAR polynucleotides described herein.

c. Methods of Making

Provided herein are methods of making the CARs and the CAR containing immune cells of the disclosure. A variety of known techniques can be utilized in making the polynucleotides, polypeptides, vectors, antigen binding domains, immune cells, compositions, and the like according to the disclosure.

Polynucleotides and Vectors

In some embodiments, a CAR can be introduced into an immune cell as a transgene via a plasmid vector. In some embodiments, the plasmid vector can also contain, for example, a selection marker which provides for identification and/or selection of cells which received the vector.

CAR polypeptides may be synthesized in situ in the cell after introduction of polynucleotides encoding the CAR polypeptides into the cell. Alternatively, CAR polypeptides may be produced outside of cells, and then introduced into cells. Methods for introducing a polynucleotide construct into cells are known in the art. In some embodiments, stable transformation methods (e.g., using a lentiviral vector) can be used to integrate the polynucleotide construct into the genome of the cell. In other embodiments, transient transformation methods can be used to transiently express the polynucleotide construct, and the polynucleotide construct not integrated into the genome of the cell. In other embodiments, virus-mediated methods can be used. The polynucleotides may be introduced into a cell by any suitable means such as for example, recombinant viral vectors (e.g., retroviruses, adenoviruses), liposomes, and the like. Transient transformation methods include, for example without limitation, microinjection, electroporation or particle bombardment. Polynucleotides may be included in vectors, such as for example plasmid vectors or viral vectors.

In some embodiments, isolated nucleic acids are provided comprising a promoter operably linked to a first polynucleotide encoding a CD19 antigen binding domain, at least one costimulatory molecule, and an activating domain. In some embodiments, the nucleic acid construct is contained within a viral vector. In some embodiments, the viral vector is selected from the group consisting of retroviral vectors, murine leukemia virus vectors, SFG vectors, adenoviral vectors, lentiviral vectors, adeno-associated virus (AAV) vectors, Herpes virus vectors, and vaccinia virus vectors. In some embodiments, the nucleic acid is contained within a plasmid.

In one aspect, the present disclosure provides a polynucleotide sequence comprising a promoter that is capable of expressing a CAR transgene in a mammalian T cell. In some embodiments, the promoter is the EF1α promoter. The native EF1α promoter drives expression of the alpha subunit of the elongation factor-1 complex, which is responsible for the enzymatic delivery of aminoacyl tRNAs to the ribosome. The EF1α promoter has been extensively used in mammalian expression plasmids and has been shown to be effective in driving CAR expression from transgenes cloned into a lentiviral vector. See, e.g., Milone et al., Mol. Ther. 17(8): 1453-1464 (2009). In some embodiments, the EF1α promoter comprises the sequence provided as SEQ ID NO: 15.

(SEQ ID NO: 15)
GCGTGAGGCTCCGGTGCCCGTCAGTGGGCAGAGCGCACATCGCCCACAGT

CCCCGAGAAGTTGGGGGGAGGGGTCGGCAATTGAACCGGTGCCTAGAGAA

GGTGGCGCGGGGTAAACTGGGAAAGTGATGTCGTGTACTGGCTCCGCCTT

TTTCCCGAGGGTGGGGGAGAACCGTATATAAGTGCAGTAGTCGCCGTGAA

CGTTCTTTTTCGCAACGGGTTTGCCGCCAGAACACAGGTAAGTGCCGTGT

GTGGTTCCCGCGGGCCTGGCCTCTTTACGGGTTATGGCCCTTGCGTGCCT

TGAATTACTTCCACGCCCCTGGCTGCAGTACGTGATTCTTGATCCCGAGC

TTCGGGTTGGAAGTGGGTGGGAGAGTTCGAGGCCTTGCGCTTAAGGAGCC

CCTTCGCCTCGTGCTTGAGTTGAGGCCTGGCCTGGGCGCTGGGGCCGCCG

CGTGCGAATCTGGTGGCACCTTCGCGCCTGTCTCGCTGCTTTCGATAAGT

CTCTAGCCATTTAAAATTTTTGATGACCTGCTGCGACGCTTTTTTTCTGG

CAAGATAGTCTTGTAAATGCGGGCCAAGATCTGCACACTGGTATTTCGGT

TTTTGGGGCCGCGGGCGGCGACGGGGCCCGTGCGTCCCAGCGCACATGTT

CGGCGAGGCGGGGCCTGCGAGCGCGGCCACCGAGAATCGGACGGGGGTAG

TCTCAAGCTGGCCGGCCTGCTCTGGTGCCTGGCCTCGCGCCGCCGTGTAT

CGCCCCGCCCTGGGCGGCAAGGCTGGCCCGGTCGGCACCAGTTGCGTGAG

CGGAAAGATGGCCGCTTCCCGGCCCTGCTGCAGGGAGCTCAAAATGGAGG

ACGCGGCGCTCGGGAGAGCGGGCGGGTGAGTCACCCACACAAAGGAAAAG

GGCCTTTCCGTCCTCAGCCGTCGCTTCATGTGACTCCACGGAGTACCGGG

CGCCGTCCAGGCACCTCGATTAGTTCTCGAGCTTTTGGAGTACGTCGTCT

TTAGGTTGGGGGAGGGGTTTTATGCGATGGAGTTTCCCCACACTGAGTG

GGTGGAGACTGAAGTTAGGCCAGCTTGGCACTTGATGTAATTCTCCTTGG

AATTTGCCCTTTTTGAGTTTGGATCTTGGTTCATTCTCAAGCCTCAGACA

GTGGTTCAAAGTTTTTTTCTTCCATTTCAGGTGTCGTGA

The EF1α promoter sequence shown above comprises the first exon (bold) and the first intron (underlined, SEQ ID NO: 39), followed by the N-terminal portion of the second exon, of the EF1α gene. In some embodiments, the polynucleotide provided herein comprises a short EF1α promoter. In some embodiments, the polynucleotide provided herein comprises an EF1α promoter that is shorter than the nucleic acid sequence of SEQ ID NO:15. In some embodiments, the polynucleotide provided herein comprises an EF1α promoter that does not comprise the first intron of the EF1α gene. In some embodiments, the polynucleotide provided herein comprises an EF1α promoter that does not comprise the nucleic acid sequence of SEQ ID NO:39.

In some embodiments, the promoter comprises the sequence provided as SEQ ID NO:16.

```
                                              (SEQ ID NO: 16)
GCGTGAGGCTCCGGTGCCCGTCAGTGGGCAGAGCGCACATCGCCCACAGT

CCCCGAGAAGTTGGGGGAGGGGTCGGCAATTGAACCGGTGCCTAGAGAA

GGTGGCGCGGGTAAACTGGGAAAGTGATGTCGTGTACTGGCTCCGCCTT

TTTCCCGAGGGTGGGGGAGAACCGTATATAAGTGCAGTAGTCGCCGTGAA

CGTTCTTTTTCGCAACGGGTTTGCCGCCAGAACACAG
```

Prior to the in vitro manipulation or genetic modification of the immune cells described herein, the cells may be obtained from a subject. The cells expressing a CD19 CAR may be derived from an allogenic or autologous process.

Source Material

In some embodiments, the immune cells comprise T cells. T cells can be obtained from a number of sources, including peripheral blood mononuclear cells (PBMCs), bone marrow, lymph nodes tissue, cord blood, thymus tissue, tissue from a site of infection, ascites, pleural effusion, spleen tissue, and tumors. In certain embodiments, T cells can be obtained from a unit of blood collected from the subject using any number of techniques known to the skilled person, such as FICOLL™ separation.

Cells may be obtained from the circulating blood of an individual by apheresis. The apheresis product typically contains lymphocytes, including T cells, monocytes, granulocytes, B cells, other nucleated white blood cells, red blood cells, and platelets. In certain embodiments, the cells collected by apheresis may be washed to remove the plasma fraction, and placed in an appropriate buffer or media for subsequent processing.

In certain embodiments, T cells are isolated from PBMCs by lysing the red blood cells and depleting the monocytes, for example, using centrifugation through a PERCOLL™ gradient. A specific subpopulation of T cells, (e.g., CD28+, CD4+, CDS+, CD45RA−, and CD45RO+ T cells or CD28+, CD4+, CDS+, CD45RA−, CD45RO+, and CD62L+ T cells) can be further isolated by positive or negative selection techniques known in the art. For example, enrichment of a T cell population by negative selection can be accomplished with a combination of antibodies directed to surface markers unique to the negatively selected cells. One method for use herein is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. Flow cytometry and cell sorting may also be used to isolate cell populations of interest for use in the present disclosure.

PBMCs may be used directly for genetic modification with the immune cells (such as CARs or TCRs) using methods as described herein. In certain embodiments, after isolating the PBMCs, T lymphocytes can be further isolated and both cytotoxic and helper T lymphocytes can be sorted into naive, memory, and effector T cell subpopulations either before or after genetic modification and/or expansion.

In some embodiments, CD8+ cells are further sorted into naive, stem cell memory, central memory, and effector cells by identifying cell surface antigens that are associated with each of these types of CD8+ cells. In some embodiments, the expression of phenotypic markers of central memory T cells include CD45RO, CD62L, CCR7, CD28, CD3, and CD127 and are negative for granzyme B. In some embodiments, stem cell memory T cells are CD45RO−, CD62L+, CD8+ T cells. In some embodiments, central memory T cells are CD45RO+, CD62L+, CD8+ T cells. In some embodiments, effector T cells are negative for CD62L, CCR7, CD28, and CD127, and positive for granzyme B and perforin. In certain embodiments, CD4+ T cells are further sorted into subpopulations. For example, CD4+T helper cells can be sorted into naive, central memory, and effector cells by identifying cell populations that have cell surface antigens.

Stem Cell Derived Immune Cells

In some embodiments, the immune cells may be derived from embryonic stem (ES) or induced pluripotent stem (iPS) cells. Suitable HSCs, ES cells, iPS cells and other stems cells may be cultivated immortal cell lines or isolated directly from a patient. Various methods for isolating, developing, and/or cultivating stem cells are known in the art and may be used to practice the present invention.

In some embodiments, the immune cell is an induced pluripotent stem cell (iPSC) derived from a reprogrammed T-cell. In some embodiments, the source material may be an induced pluripotent stem cell (iPSC) derived from a T cell or non-T cell. The source material may be an embryonic stem cell. The source material may be a B cell, or any other cell from peripheral blood mononuclear cell isolates, hematopoietic progenitor, hematopoietic stem cell, mesenchymal stem cell, adipose stem cell, or any other somatic cell type.

Genetic Modification of Isolated Cells

The immune cells, such as T cells, can be genetically modified following isolation using known methods, or the immune cells can be activated and expanded (or differentiated in the case of progenitors) in vitro prior to being genetically modified. In some embodiments, the isolated immune cells are genetically modified to reduce or eliminate expression of endogenous TCRα and/or CD52. In some embodiments, the cells are genetically modified using gene editing technology (e.g., CRISPR/Cas9, a zinc finger nuclease (ZFN), a TALEN, a MegaTAL, a meganuclease) to reduce or eliminate expression of endogenous proteins (e.g., TCRα and/or CD52). In another embodiment, the immune cells, such as T cells, are genetically modified with the chimeric antigen receptors described herein (e.g., transduced with a viral vector comprising one or more nucleotide sequences encoding a CAR) and then are activated and/or expanded in vitro. Methods for activating and expanding T cells are known in the art and are described, for example, in U.S. Pat. Nos. 6,905,874; 6,867,041; 6,797,514; and PCT WO2012/079000, the contents of which are hereby incorporated by reference in their entirety. Generally, such methods include contacting PBMC or isolated T cells with a stimulatory molecule and a costimulatory molecule, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). One example is The Dynabeads® system, a CD3/CD28 activator/stimulator system for physiological activation of human T cells. In other embodiments, the T cells may be activated and stimulated to proliferate with feeder cells and appropriate antibodies and cytokines using methods such as those described in U.S. Pat. Nos. 6,040,177; 5,827,642; and WO2012129514, the contents of which are hereby incorporated by reference in their entirety.

Certain methods for making the constructs and engineered immune cells of the disclosure are described in PCT application PCT/US15/14520, the contents of which are hereby incorporated by reference in their entirety.

It will be appreciated that PBMCs can further include other cytotoxic lymphocytes such as NK cells or NKT cells. An expression vector carrying the coding sequence of a chimeric receptor as disclosed herein can be introduced into a population of human donor T cells, NK cells or NKT cells. Successfully transduced T cells that carry the expression vector can be sorted using flow cytometry to isolate CD3 positive T cells and then further propagated to increase the number of these CAR expressing T cells in addition to cell activation using anti-CD3 antibodies and IL-2 or other methods known in the art as described elsewhere herein. Standard procedures are used for cryopreservation of T cells expressing the CAR for storage and/or preparation for use in a human subject. In one embodiment, the in vitro transduction, culture and/or expansion of T cells are performed in the absence of non-human animal derived products such as fetal calf serum and fetal bovine serum.

For cloning of polynucleotides, the vector may be introduced into a host cell (an isolated host cell) to allow replication of the vector itself and thereby amplify the copies of the polynucleotide contained therein. The cloning vectors may contain sequence components generally include, without limitation, an origin of replication, promoter sequences, transcription initiation sequences, enhancer sequences, and selectable markers. These elements may be selected as appropriate by a person of ordinary skill in the art. For example, the origin of replication may be selected to promote autonomous replication of the vector in the host cell.

In certain embodiments, the present disclosure provides isolated host cells containing the vector provided herein. The host cells containing the vector may be useful in expression or cloning of the polynucleotide contained in the vector. Suitable host cells can include, without limitation, prokaryotic cells, fungal cells, yeast cells, or higher eukaryotic cells such as mammalian cells. Suitable prokaryotic cells for this purpose include, without limitation, eubacteria, such as Gram-negative or Gram-positive organisms, for example, Enterobactehaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*.

The vector can be introduced to the host cell using any suitable methods known in the art, including, without limitation, DEAE-dextran mediated delivery, calcium phosphate precipitate method, cationic lipids mediated delivery, liposome mediated transfection, electroporation, microprojectile bombardment, receptor-mediated gene delivery, delivery mediated by polylysine, histone, chitosan, and peptides. Standard methods for transfection and transformation of cells for expression of a vector of interest are well known in the art. In a further embodiment, a mixture of different expression vectors can be used in genetically modifying a donor population of immune effector cells wherein each vector encodes a different CAR as disclosed herein. The resulting transduced immune effector cells form a mixed population of engineered cells, with a proportion of the engineered cells expressing more than one different CARs.

In some embodiments, the vector comprises a lentiviral vector. The lentiviral vector comprising a CAR coding sequence can be introduced into a lentiviral packaging cell line and the lentivirus produced by the packaging cell line can be used for transduction of T cells to generate CAR-T cells. To make lentivirus encoding CARs, HEK-293T cells can be plated at 0.4 million cells per mL in 2 mL of DMEM (Gibco) supplemented with 10% FBS (Hyclone or JR Scientific) per well of a 6-well plate on Day 0. On Day 1, the lentivirus can be prepared by mixing together lentiviral packaging vectors 1.5 ug psPAX2, 0.5 ug pMD2G, and 0.5 ug of the appropriate transfer CAR vector in 250 uL Opti-MEM (Gibco) per well of the 6-well plate ("DNA mix"). 10 uL Lipofectamine 2000 (Invitrogen) in 250 uL Opti-MEM can be incubated at room temperature for 5 minutes and then added to the DNA mix. The mixture can be incubated at room temperature for 20 minutes and the total volume of 500 uL was slowly added to the sides of the wells containing HEK-293T. The general methods of CAR-containing lentivirus production and transduction are generally known in the art, for example, see Milone et al., Leukemia, 2018, 32:1529-1541; Sanber et al., Construction of stable packaging cell lines for clinical lentiviral vector production, Nature 2015, DOI: 10.1038; Roddie et al., Cytotherapy 2019, 21:327-340, all of which are incorporate herein by reference in their entireties. In one embodiment, the disclosure provides a method of storing genetically engineered cells expressing CARs or TCRs which target a CD19 protein. This involves cryopreserving the immune cells such that the cells remain viable upon thawing. A fraction of the immune cells expressing the CARs can be cryopreserved by methods known in the art to provide a permanent source of such cells for the future treatment of patients afflicted with a malignancy. When needed, the cryopreserved transformed immune cells can be thawed, grown and expanded for more such cells.

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion media can be any isotonic medium formulation, typically normal saline, Normosol™ R (Abbott) or Plasma-Lyte™ A (Baxter), but also 5% dextrose in water or Ringer's lactate can be utilized. The infusion medium can be supplemented with human serum albumin.

Allogeneic CAR T Cells

The process for manufacturing allogeneic CAR T therapy, or AlloCARs™, involves harvesting healthy, selected, screened and tested T cells from healthy donors. Next, the T cells are engineered to express CARs, which recognize certain cell surface proteins (e.g., CD19) that are expressed in hematologic or solid tumors. Allogeneic T cells are gene edited to reduce the risk of graft versus host disease (GvHD) and to prevent allogeneic rejection. A T cell receptor gene (e.g., TCRα, TCRβ) is knocked out to avoid GvHD. The CD52 gene can be knocked out to render the CAR T product resistant to anti-CD52 antibody treatment. Anti-CD52 antibody treatment can therefore be used to suppress the host immune system and allow the CAR T to stay engrafted to achieve full therapeutic impact. The engineered T cells then undergo a purification step and are ultimately cryopreserved in vials for delivery to patients.

Autologous CAR T Cells

Autologous chimeric antigen receptor (CAR) T cell therapy, involves collecting a patient's own cells (e.g., white blood cells, including T cells) and genetically engineering the T cells to express CARs that recognize target expressed on the cell surface of one or more specific cancer cells and kill cancer cells. The engineered cells are then cryopreserved and subsequently administered to the patient.

IV. Methods of Treatment

The disclosure comprises methods for treating or preventing a condition associated with undesired and/or elevated CD19 levels in a patient, comprising administering to a patient in need thereof an effective amount of at least one CAR, or immune-cell comprising a CAR disclosed herein.

Methods are provided for treating diseases or disorders, including cancer. In some embodiments, the disclosure relates to creating a T cell-mediated immune response in a subject, comprising administering an effective amount of the engineered immune cells of the present application to the subject. In some embodiments, the T cell-mediated immune response is directed against a target cell or cells. In some embodiments, the engineered immune cell comprises a chimeric antigen receptor (CAR). In some embodiments, the target cell is a tumor cell. In some aspects, the disclosure comprises a method for treating or preventing a malignancy, said method comprising administering to a subject in need thereof an effective amount of at least one isolated antigen binding domain described herein. In some aspects, the disclosure comprises a method for treating or preventing a malignancy, said method comprising administering to a subject in need thereof an effective amount of at least one immune cell, wherein the immune cell comprises at least one chimeric antigen receptor, T cell receptor, and/or isolated antigen binding domain as described herein.

The CAR containing immune cells of the disclosure can be used to treat malignancies involving aberrant expression of CD19. In some embodiments, CAR containing immune cells of the disclosure can be used to treat cancer. As used herein, the term "cancer" includes, but is not limited to, solid tumors and blood born tumors. The term "cancer" refers to disease of skin tissues, organs, blood, and vessels, including, but not limited to, cancers of the bladder, bone or blood, brain, breast, cervix, chest, colon, endrometrium, esophagus, eye, head, kidney, liver, lymph nodes, lung, mouth, neck, ovaries, pancreas, prostate, rectum, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin lymphoma, non-Hodgkin lymphoma (NHL), cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In a specific embodiment, the cancer is metastatic. In another embodiment, the cancer is refractory or resistance to chemotherapy or radiation.

In exemplary embodiments, the CAR containing immune cells, e.g., CAR-T cells of the disclosure, are used to treat NHL.

Also provided are methods for reducing the size of a tumor in a subject, comprising administering to the subject an engineered cell of the present disclosure to the subject, wherein the cell comprises a chimeric antigen receptor comprising a CD19 antigen binding domain and binds to a CD19 antigen on the tumor.

In some embodiments, the subject has a solid tumor, or a blood malignancy such as lymphoma or leukemia. In some embodiments, the engineered cell is delivered to a tumor bed. In some embodiments, the cancer is present in the bone marrow of the subject. In some embodiments, the engineered cells are autologous immune cells, e.g., autologous T cells. In some embodiments, the engineered cells are allogeneic immune cells, e.g., allogeneic T cells. In some embodiments, the engineered cells are heterologous immune cells, e.g., heterologous T cells. In some embodiments, the engineered cells of the present application are transfected or transduced in vivo. In other embodiments, the engineered cells are transfected or transduced ex vivo. As used herein, the term "in vitro cell" refers to any cell which is cultured ex vivo.

A "therapeutically effective amount," "effective dose," "effective amount," or "therapeutically effective dosage" of a therapeutic agent, e.g., engineered CART cells, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The terms "patient" and "subject" are used interchangeably and include human and non-human animal subjects as well as those with formally diagnosed disorders, those without formally recognized disorders, those receiving medical attention, those at risk of developing the disorders, etc.

The term "treat" and "treatment" includes therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors. The term "prevent" does not require the 100% elimination of the possibility of an event. Rather, it denotes that the likelihood of the occurrence of the event has been reduced in the presence of the compound or method.

Desired treatment amounts of cells in the composition is generally at least 2 cells (for example, at least 1 CD8+ central memory T cell and at least 1 CD4+ helper T cell subset) or is more typically greater than $10^2$ cells, and up to $10^6$, up to and including $10^8$ or $10^9$ cells and can be more than $10^{10}$ cells. The number of cells will depend upon the desired use for which the composition is intended, and the type of cells included therein. The density of the desired cells is typically greater than $10^6$ cells/ml and generally is greater than $10^7$ cells/ml, generally 108 cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some aspects of the present disclosure, particularly since all the infused cells will be redirected to a particular target antigen (CD19), lower numbers of cells, in the range of $10^6$/kilogram ($10^6$-$10^{11}$ per patient) may be administered. CAR treatments may be administered multiple times at dosages within these ranges. The cells may be autologous, allogeneic, or heterologous to the patient undergoing therapy.

In some embodiments, the therapeutically effective amount of the CAR T cells is about $1 \times 10^5$ cells/kg, about $2 \times 10^5$ cells/kg, about $3 \times 10^5$ cells/kg, about $4 \times 10^5$ cells/kg, about $5 \times 10^5$ cells/kg, about $6 \times 10^5$ cells/kg, about $7 \times 10^5$ cells/kg, about $8 \times 10^5$ cells/kg, about $9 \times 10^5$ cells/kg, $2 \times 10^6$ cells/kg, about $3 \times 10^6$ cells/kg, about $4 \times 10^6$ cells/kg, about $5 \times 10^6$ cells/kg, about $6 \times 10^6$ cells/kg, about $7 \times 10^6$ cells/kg, about $8 \times 10^6$ cells/kg, about $9 \times 10^6$ cells/kg, about $1 \times 10^7$ cells/kg, about $2 \times 10^7$ cells/kg, about $3 \times 10^7$ cells/kg, about $4 \times 10^7$ cells/kg, about $5 \times 10^7$ cells/kg, about $6 \times 10^7$ cells/kg, about $7 \times 10^7$ cells/kg, about $8 \times 10^7$ cells/kg, or about $9 \times 10^7$ cells/kg.

In some embodiments, target doses for CAR+/CAR-T+/TCR+ cells range from $1 \times 10^6$-$2 \times 10^8$ cells/kg, for example $2 \times 10^6$ cells/kg. It will be appreciated that doses above and below this range may be appropriate for certain subjects, and appropriate dose levels can be determined by the healthcare provider as needed. Additionally, multiple doses of cells can be provided in accordance with the disclosure.

In some aspects, the disclosure comprises a pharmaceutical composition comprising at least one antigen binding domain as described herein and a pharmaceutically acceptable excipient. In some embodiments, the pharmaceutical composition further comprises an additional active agent.

The CAR expressing cell populations of the present disclosure may be administered either alone, or as a pharmaceutical composition in combination with diluents and/or with other components such as IL-2 or other cytokines or cell populations. Pharmaceutical compositions of the present disclosure may comprise a CAR or TCR expressing cell population, such as T cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure are preferably formulated for intravenous administration.

The pharmaceutical compositions (solutions, suspensions or the like), may include one or more of the following: sterile diluents such as water for injection, saline solution, preferably physiological saline, Ringer's solution, isotonic sodium chloride, fixed oils such as synthetic mono- or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

In some embodiments, upon administration to a patient, engineered immune cells expressing at their cell surface any one of the CD19-specific CARs described herein may reduce, kill or lyse endogenous CD19-expressing cells of the patient. In one embodiment, a percentage reduction or lysis of CD19-expressing endogenous cells or cells of a cell line expressing CD19 by engineered immune cells expressing any one of the CD19-specific CARs described herein is at least about or greater than 10%, 15%, 20%, 25%, 30%, 35%, 40%, 45%, 50%, 55%, 60%, 65%, 70%, 75%, 80%, 85%, 90%, or 95%. In one embodiment, a percentage reduction or lysis of CD19-expressing endogenous cells or cells of a cell line expressing CD19 by engineered immune cells expressing any one of the CD19-specific CARs described herein is about 5% to about 95%, about 10% to about 95%, about 10% to about 90%, about 10% to about 80%, about 10% to about 70%, about 10% to about 60%, about 10% to about 50%, about 10% to about 40%, about 20% to about 90%, about 20% to about 80%, about 20% to about 70%, about 20% to about 60%, about 20% to about 50%, about 25% to about 75%, or about 25% to about 60%. In one embodiment, the endogenous CD19-expressing cells are endogenous CD19-expressing bone marrow cells.

In one embodiment, the percent reduction or lysis of target cells, e.g., a cell line expressing CD19, by engineered immune cells expressing at their cell surface membrane a CD19-specific CAR of the disclosure can be measured using the assay disclosed herein.

The methods can further comprise administering one or more chemotherapeutic agent. In certain embodiments, the chemotherapeutic agent is a lymphodepleting (preconditioning) chemotherapeutic. For example, methods of conditioning a patient in need of a T cell therapy comprising administering to the patient specified beneficial doses of cyclophosphamide (between 200 mg/m²/day and 2000 mg/m²/day, about 100 mg/m²/day and about 2000 mg/m²/day; e.g., about 100 mg/m²/day, about 200 mg/m²/day, about 300 mg/m²/day, about 400 mg/m²/day, about 500 mg/m²/day, about 600 mg/m²/day, about 700 mg/m²/day, about 800 mg/m²/day, about 900 mg/m²/day, about 1000 mg/m²/day, about 1500 mg/m²/day or about 2000 mg/m²/day) and specified doses of fludarabine (between 20 mg/m²/day and 900 mg/m²/day, between about 10 mg/m²/day and about 900 mg/m²/day; e.g., about 10 mg/m²/day, about 20 mg/m²/day, about 30 mg/m²/day, about 40 mg/m²/day, about 40 mg/m²/day, about 50 mg/m²/day, about 60 mg/m²/day, about 70 mg/m²/day, about 80 mg/m²/day, about 90 mg/m²/day, about 100 mg/m²/day, about 500 mg/m²/day or about 900 mg/m²/day). A preferred dose regimen involves treating a patient comprising administering daily to the patient about 300 mg/m²/day of cyclophosphamide and about 30 mg/m²/day of fludarabine for three days prior to administration of a therapeutically effective amount of engineered T cells to the patient.

In some embodiments, lymphodepletion further comprises administration of a CD52 antibody. In some embodiments, the CD52 antibody is administered at a dose of about 13 mg/day IV.

In other embodiments, the antigen binding domain, transduced (or otherwise engineered) cells and the chemotherapeutic agent are administered each in an amount effective to treat the disease or condition in the subject.

In certain embodiments, compositions comprising CAR-expressing immune effector cells disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2''-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel (TAXOL™, Bristol-Myers Squibb) and doxetaxel (TAXOTERE®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RF S2000; difluoromethylomithine (DMFO); retinoic acid derivatives such as Targretin™ (bexarotene), Panretin™, (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (Cytoxan®), Doxorubicin (hydroxydoxorubicin), Vincristine (Oncovin®), and Prednisone.

In some embodiments, the chemotherapeutic agent is administered at the same time or within one week after the administration of the engineered cell, polypeptide, or nucleic acid. In other embodiments, the chemotherapeutic agent is administered from 1 to 4 weeks or from 1 week to 1 month, 1 week to 2 months, 1 week to 3 months, 1 week to 6 months, 1 week to 9 months, or 1 week to 12 months after the administration of the engineered cell, polypeptide, or nucleic acid. In other embodiments, the chemotherapeutic agent is administered at least 1 month before administering the cell, polypeptide, or nucleic acid. In some embodiments, the methods further comprise administering two or more chemotherapeutic agents.

A variety of additional therapeutic agents may be used in conjunction with the compositions described herein. For example, potentially useful additional therapeutic agents include PD-1 inhibitors such as nivolumab (Opdivo®), pembrolizumab (Keytruda®), pembrolizumab, pidilizumab, and atezolizumab.

Additional therapeutic agents suitable for use in combination with the disclosure include, but are not limited to, ibrutinib (Imbruvica®), ofatumumab (Arzerra®), rituximab (Rituxan®), bevacizumab (Avastin®), trastuzumab (Herceptin®), trastuzumab emtansine (KADCYLA®, imatinib (Gleevec®), cetuximab (Erbitux®, panitumumab) (Vectibix®), catumaxomab, ibritumomab, ofatumumab, tositumomab, brentuximab, alemtuzumab, gemtuzumab, erlotinib, gefitinib, vandetanib, afatinib, lapatinib, neratinib, axitinib, masitinib, pazopanib, sunitinib, sorafenib, toceranib, lestaurtinib, axitinib, cediranib, lenvatinib, nintedanib, pazopanib, regorafenib, semaxanib, sorafenib, sunitinib, tivozanib, toceranib, vandetanib, entrectinib, cabozantinib, imatinib, dasatinib, nilotinib, ponatinib, radotinib, bosutinib, lestaurtinib, ruxolitinib, pacritinib, cobimetinib, selumetinib, trametinib, binimetinib, alectinib, ceritinib, crizotinib, aflibercept, adipotide, denileukin diftitox, mTOR inhibitors such as Everolimus and Temsirolimus, hedgehog inhibitors such as sonidegib and vismodegib, CDK inhibitors such as CDK inhibitor (palbociclib).

In some embodiments, the composition comprising CAR-containing immune cells may be administered with a therapeutic regimen to prevent cytokine release syndrome (CRS) or neurotoxicity. The therapeutic regimen to prevent cytokine release syndrome (CRS) or neurotoxicity may include lenzilumab, tocilizumab, atrial natriuretic peptide (ANP), anakinra, iNOS inhibitors (e.g., L-NIL or 1400 W). In additional embodiments, the composition comprising CAR-containing immune cells can be administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate. Exemplary NSAIDs include ibuprofen, naproxen, naproxen sodium, Cox-2 inhibitors, and sialylates. Exemplary analgesics include acetaminophen, oxycodone, tramadol of proporxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular) and minocycline.

In certain embodiments, the compositions described herein are administered in conjunction with a cytokine. Examples of cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, IL-21 a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

V. Methods of Sorting and Depletion

In some embodiments, provided are methods for in vitro sorting of a population of immune cells, wherein a subset of the population of immune cells comprises engineered immune cells expressing any one of the CD19-specific CARs comprising epitopes specific for monoclonal antibodies (e.g., exemplary mimotope sequences). The method comprises contacting the population of immune cells with a monoclonal antibody specific for the epitopes and selecting the immune cells that bind to the monoclonal antibody to obtain a population of cells enriched in engineered immune cells expressing the CD19-specific CAR.

In some embodiments, said monoclonal antibody specific for said epitope is optionally conjugated to a fluorophore. In this embodiment, the step of selecting the cells that bind to the monoclonal antibody can be done by Fluorescence Activated Cell Sorting (FACS).

In some embodiments, said monoclonal antibody specific for said epitope is optionally conjugated to a magnetic particle. In this embodiment, the step of selecting the cells that bind to the monoclonal antibody can be done by Magnetic Activated Cell Sorting (MACS).

In some embodiments, the mAb used in the method for sorting immune cells expressing the CAR is chosen from alemtuzumab, ibritumomab tiuxetan, muromonab-CD3, tositumomab, abciximab, basiliximab, brentuximab vedotin, cetuximab, infliximab, rituximab, bevacizumab, certolizumab pegol, daclizumab, eculizumab, efalizumab, gemtuzumab, natalizumab, omalizumab, palivizumab, ranibizumab, tocilizumab, trastuzumab, vedolizumab, adalimumab, belimumab, canakinumab, denosumab, golimumab, ipilimumab, ofatumumab, panitumumab, QBEND-10 and/or ustekinumab. In some embodiments, said mAb is rituximab. In another embodiment, said mAb is QBEND-10.

In some embodiments, the population CAR-expressing immune cells obtained when using the method for in vitro sorting CAR-expressing immune cells described above, comprises at least 70%, 75%, 80%, 85%, 90%, 95% of CAR-expressing immune cells. In some embodiments, the population of CAR-expressing immune cells obtained when using the method for in vitro sorting CAR-expressing immune cells, comprises at least 85% CAR-expressing immune cells.

In some embodiments, the population of CAR-expressing immune cells obtained when using the method for in vitro sorting CAR-expressing immune cells described above shows increased cytotoxic activity in vitro compared with the initial (non-sorted) cell population. In some embodiments, said cytotoxic activity in vitro is increased by 10%, 20%, 30% or 50%. In some embodiments, the immune cells are T-cells.

In some embodiments, the mAbs are previously bound onto a support or surface. Non-limiting examples of solid support may include a bead, agarose bead, a magnetic bead, a plastic welled plate, a glass welled plate, a ceramic welled plate, a column, or a cell culture bag.

The CAR-expressing immune cells to be administered to the recipient may be enriched in vitro from the source population. Methods of expanding source populations may include selecting cells that express an antigen such as CD34 antigen, using combinations of density centrifugation, immuno-magnetic bead purification, affinity chromatography, and fluorescent activated cell sorting.

Flow cytometry may be used to quantify specific cell types within a population of cells. In general, flow cytometry is a method for quantitating components or structural features of cells primarily by optical means. Since different cell types can be distinguished by quantitating structural features, flow cytometry and cell sorting can be used to count and sort cells of different phenotypes in a mixture.

A flow cytometry analysis involves two primary steps: 1) labeling selected cell types with one or more labeled markers, and T) determining the number of labeled cells relative to the total number of cells in the population. In some embodiments, the method of labeling cell types includes binding labeled antibodies to markers expressed by the specific cell type. The antibodies may be either directly labeled with a fluorescent compound or indirectly labeled using, for example, a fluorescent-labeled second antibody which recognizes the first antibody.

In some embodiments, the method used for sorting T cells expressing CAR is the Magnetic-Activated Cell Sorting (MACS). Magnetic-activated cell sorting (MACS) is a method for separation of various cell populations depending on their surface antigens (CD molecules) by using super-paramagnetic nanoparticles and columns. MACS may be used to obtain a pure cell population. Cells in a single-cell suspension may be magnetically labeled with microbeads. The sample is applied to a column composed of ferromagnetic spheres, which are covered with a cell-friendly coating allowing fast and gentle separation of cells. The unlabeled cells pass through while the magnetically labeled cells are retained within the column. The flow-through can be collected as the unlabeled cell fraction. After a washing step, the column is removed from the separator, and the magnetically labeled cells are eluted from the column.

Detailed protocol for the purification of specific cell population such as T-cell can be found in Basu S et al. (2010). (Basu S, Campbell H M, Dittel B N, Ray A. (2010). Purification of specific cell population by fluorescence activated cell sorting (FACS). J Vis Exp. (41): 1546).

In some aspects, the present disclosure provides a method for depleting CD19 specific CAR-expressing immune cells by in vivo depletion. in vivo depletion may include the administration of a treatment (e.g., a molecule that binds an epitope on the CAR) to a mammalian organism aiming to stop the proliferation of the CAR-expressing immune cells by inhibition or elimination.

One aspect of the invention is related to a method for in vivo depleting an engineered immune cell expressing a CD19 CAR comprising a mAb specific epitope, comprising contacting said engineered immune cell or said CAR-expressing immune cell with at least one epitope-specific mAb. Another aspect of the invention relates to a method for in vivo depleting CAR-expressing immune cell which comprises a chimeric scFv (e.g., formed by insertion of a mAb-specific epitope) by contacting said engineered immune cell with epitope-specific antibodies. In some embodiments, the immune cells are T-cells and/or the antibodies are monoclonal.

According to one embodiment, the in vivo depletion of the immune engineered cells is performed on engineered immune cells which has been previously sorted using the in vitro method of the present invention. In this case, the same infused mAb may be used. In some embodiments, the mAb-specific antigen is CD20 antigen and the epitope-specific mAb is rituximab. In some embodiments, the invention relates to a method for in vivo depleting an engineered immune cell expressing a CAR comprising an mAb-specific epitope (CAR-expressing immune cell) in a patient comprising contacting said CAR-expressing immune cell with at least one epitope-specific mAb In some embodiments, the step of contacting said engineered immune cell or said CAR-expressing immune cell with at least one epitope-specific mAb comprises infusing the patient with epitope-specific mAb (e.g., rituximab). In some embodiments, the amount of epitope-specific mAb administered to the patient is sufficient to eliminate at least 20%, 30%, 40%, 50%, 60%, 70%, 80% or 90% of the CAR-expressing immune cell in the patient.

In some embodiments, the step of contacting said engineered immune cell or said CAR-expressing immune cell with at least one epitope-specific mAb comprises infusing the patient with 375 mg/m$^2$ of rituximab, once or several times. In some embodiments, the mAb (e.g., rituximab) is administered once weekly.

In some embodiments, when immune cells expressing a CAR comprising an mAb-specific epitope (CAR-expressing immune cells) are depleted in a complement dependent cytotoxicity (CDC) assay using epitope-specific mAb, the amount of viable CAR-expressing immune cells decreases. In some embodiments, the amount of viable CAR-expressing immune cells decreases by at least 10%, 20%, 30%, 40%, 50%, 60%, 70%, 80% or 90%. In some embodiments, said mAb-specific epitope is a CD20 epitope or mimotope and/or the epitope-specific mAb is rituximab.

In certain embodiments, the in vivo depletion of CAR-engineered immune cells is performed by infusing bi-specific antibodies. By definition, a bispecific monoclonal antibody (BsAb) is an artificial protein that is composed of fragments of two different monoclonal antibodies and consequently binds to two different types of antigen. These BsAbs and their use in immunotherapy have been reviewed in Muller D and Kontermann R. E. (2010) Bispecific Antibodies for Cancer Immunotherapy, BioDrugs 24 (2): 89-98.

According to another particular embodiment, the infused bi-specific mAb is able to bind both the mAb-specific epitope borne on engineered immune cells expressing the chimeric scFv and to a surface antigen on an effector and cytotoxic cell (e.g., immune cells such as lymphocytes, macrophages, dendritic cells, natural killer cells (NK Cell), cytotoxic T lymphocytes (CTL)). By doing so, the depletion of engineered immune cells triggered by the BsAb may occur through antibody-dependent cellular cytotoxicity (ADCC). (Deo Y M, Sundarapandiyan K, Keler T, Wallace P K, and Graziano R F, (2000), Journal of Immunology, 165 (10):5954-59611).

In some embodiments, a cytotoxic drug is coupled to the epitope-specific mAbs which may be used to deplete CAR-expressing immune cells. By combining targeting capabilities of monoclonal antibodies with the cancer-killing ability of cytotoxic drugs, antibody-drug conjugate (ADC) allows a sensitive discrimination between healthy and diseased tissue when compared to the use of the drug alone. Market approvals were received for several ADCs; the technology for making them, particularly the linkers, are described in (Payne, G. (2003) Cancer Cell 3:207-212; Trail et al (2003) Cancer Immunol. Immunother. 52:328-337; Syrigos and Epenetos (1999) Anticancer Research 19:605-614; Niculescu-Duvaz and Springer (1997) Adv. Drug Del. Rev. 26:151-172; U.S. Pat. No. 4,975,278).

In some embodiments, the epitope-specific mAb to be infused is conjugated beforehand with a molecule able to promote complement dependent cytotoxicity (CDC). Therefore, the complement system helps or complements the ability of antibodies to clear pathogens from the organism. When stimulated an activation cascade is triggered as a massive amplification of the response and activation of the cell-killing membrane attack complex. Different molecule may be used to conjugate the mAb, such as glycans [Courtois, A, Gac-Breton, S., Berthou, C, Guezennec, J., Bordron, A. and Boisset, C. (2012), Complement dependent cytotoxicity activity of therapeutic antibody fragments may be acquired by immunogenic glycan coupling, Electronic Journal of Biotechnology ISSN: 0717-3458; http://www.ejbiotechnology.info DOI: 10.2225/vol15-issue 5).

VI. Kits and Articles of Manufacture

The present application provides kits comprising any one of the CD19 containing CARs or CD19 CAR containing immune cells described herein, and pharmaceutical compositions of the same. In some exemplary embodiments, a kit of the disclosure comprises allogeneic CD19 CAR-containing T-cells and a CD52 antibody for administering to the subject a lymphodepletion regiment and a CAR-T regimen.

The present application also provides articles of manufacture comprising any one of the therapeutic compositions or kits described herein. Examples of an article of manufacture include vials (e.g., sealed vials).

EXAMPLES

Example 1: Generation of Rituximab-Resistant CD19 CAR Immune Cells

Rituximab-resistant anti-CD19 chimeric antigen receptor constructs that do not express a rituximab binding site as shown in FIG. 1 and Table 4 were generated. The lentiviral vectors constructs were introduced into viral packaging cell line and anti-CD19 CAR containing lentiviruses were produced at in-house.

Pan T cells from four human donors (541, 604, 410 and 2593) were thawed and activated at $1.5 \times 10^6$ cells/ml with Large-scale T Cell TransAct™ (1:15 ratio) in the presence of IL-2 (100 IU/ml). After 2 days $1.5 \times 10^6$ cells (in 3 ml) were transduced with 2 ml of fresh lentivirus comprising the vectors described in Table 4. Schematics of the modified vectors are shown in FIG. 1. IL-2 (100 IU/ml) was added on days 0, 2, 5, 7, 9 and 12. $6 \times 10^6$ total cells were transferred to a 6-well G-Rex plate on day 5 and media exchange performed on day 9 and 12. Cells were frozen on day 13.

TABLE 4

Rituximab-resistant CD19 CAR vectors

| Vector: | Name: |
|---|---|
| anti-CD19 CAR v1.0 | pCLS-m4G7 CAR (with the RQR8 safety switch) |
| anti-CD19 CAR v1.1 | pCLS-4G7_CAR (same EF1a promoter sequence as in v1.0) |
| anti-CD19 CAR v1.2 | pCLS-EF1a(short)-4G7(co) |
| anti-CD19 CAR v1.3 | pCLS-(deltaRQR)8-4G7(co) (same EF1a promoter sequence as in v1.0) |
| anti-CD19 CAR v1.4 | pCLS-1Q8-4G7(co) (same EF1a promoter sequence as in v1.0) |
| anti-CD19 CAR v1.5 | pCLS-LQL8-4G7(co) (same EF1a promoter sequence as in v1.0) |
| anti-CD19 CAR v1.6 | pCLS-Q38-4G7(co) (same EF1a promoter sequence as in v1.0) | co = codon optimized

Figure 2A:
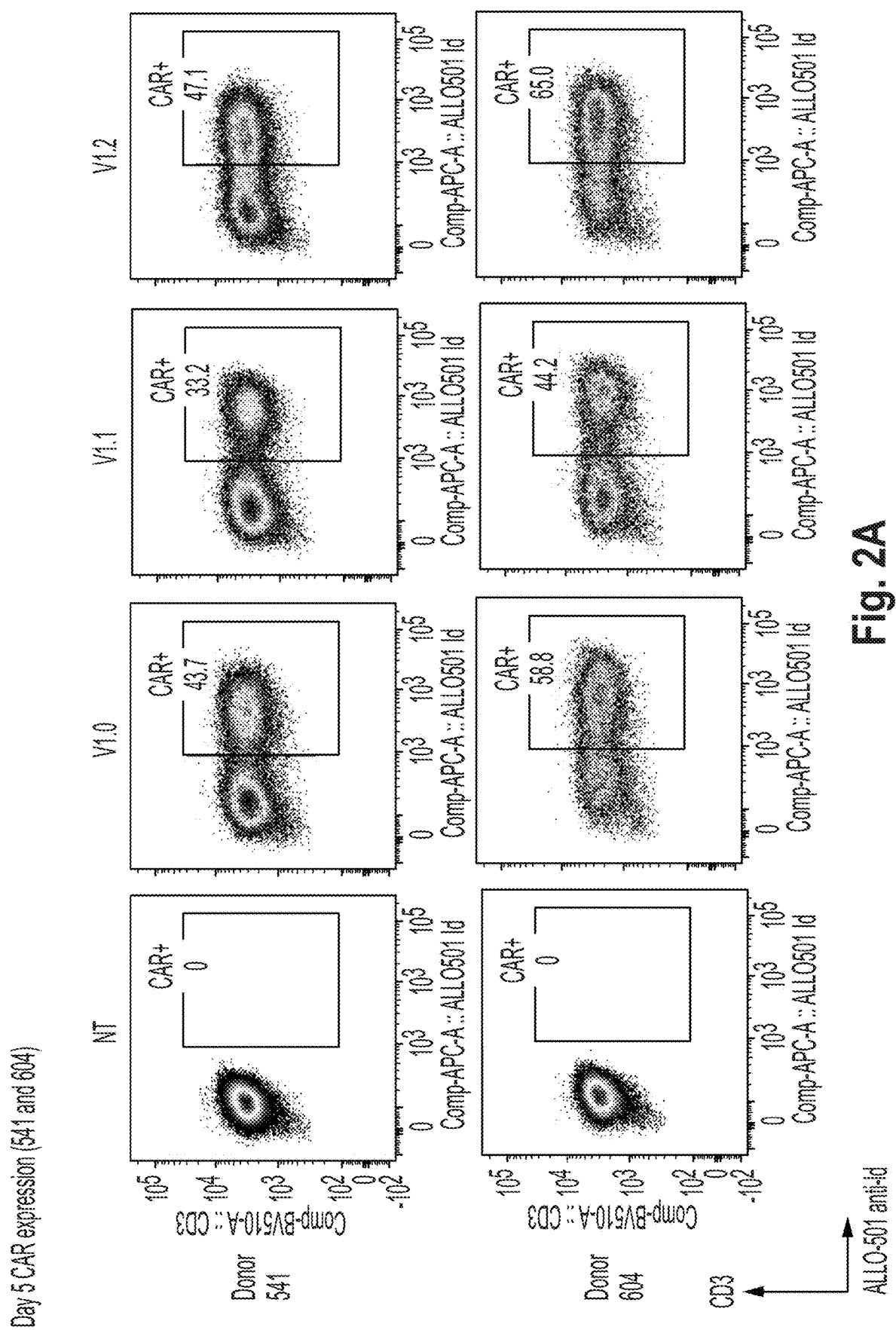
FIGS. 2A and 2B show flow cytometry plots demonstrating CAR expression on day 5 from Pan T cells transduced with the rituximab resistant CAR expression vectors.
Figure 2B:
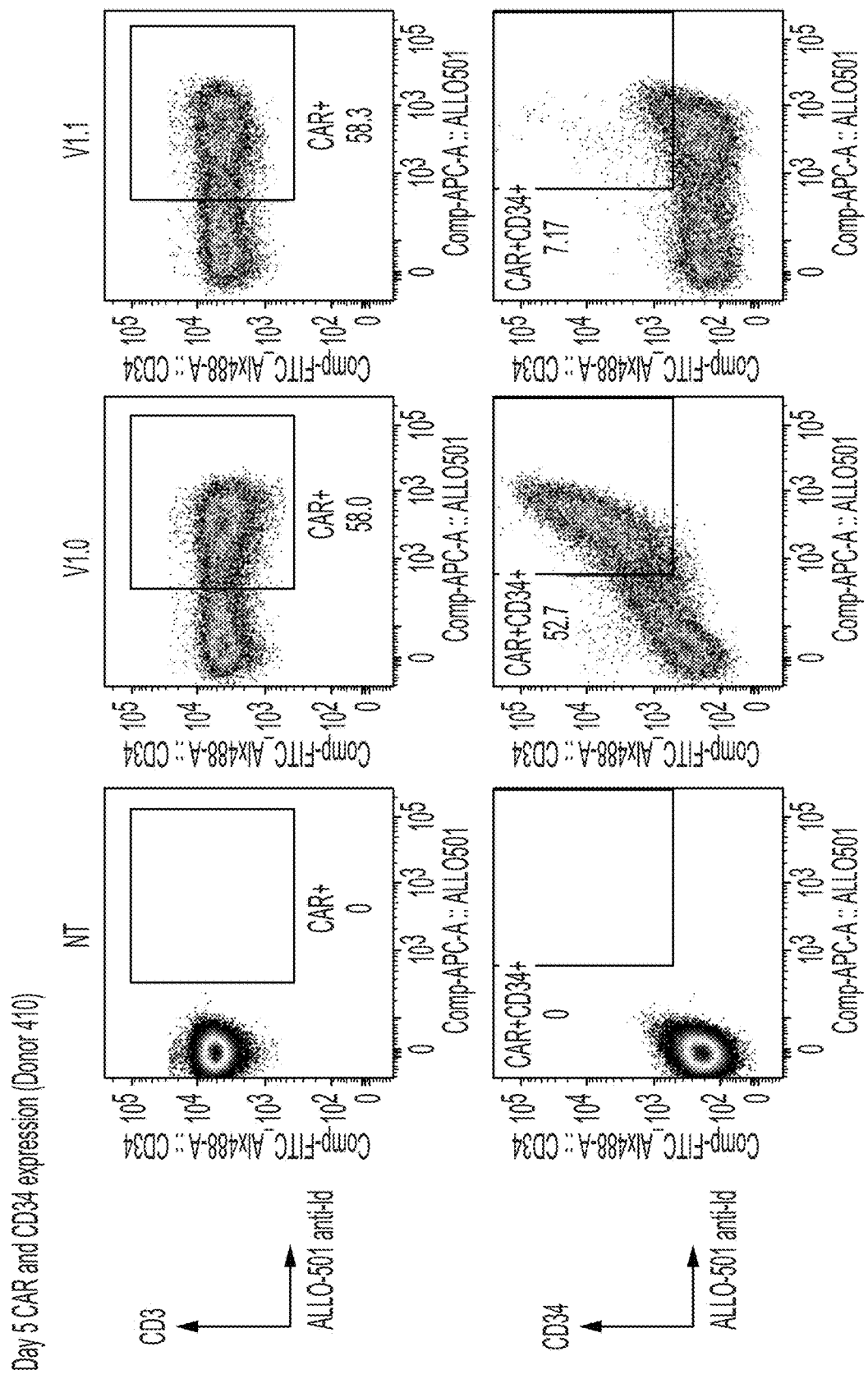

Flow cytometry experiments were performed on transduced cells gated on lymphocytes, live CD3+, CAR+, CD4/CD8 and downstream markers. A human transduction check and CD34 panel was performed on Day 5 and Day 13 using a panel of CD3, CD4, CD8, viability, CD34 and an anti-idiotype to antibody to the anti-CD19 CAR (4G7 anti-Id). FIGS. 2A and 2B show flow cytometry plots demonstrating CAR expression on day 5 from Pan T cells transduced with the CAR expression vectors shown in Table 4 using the anti-CD19 CAR anti-Id antibody.

Figure 3:
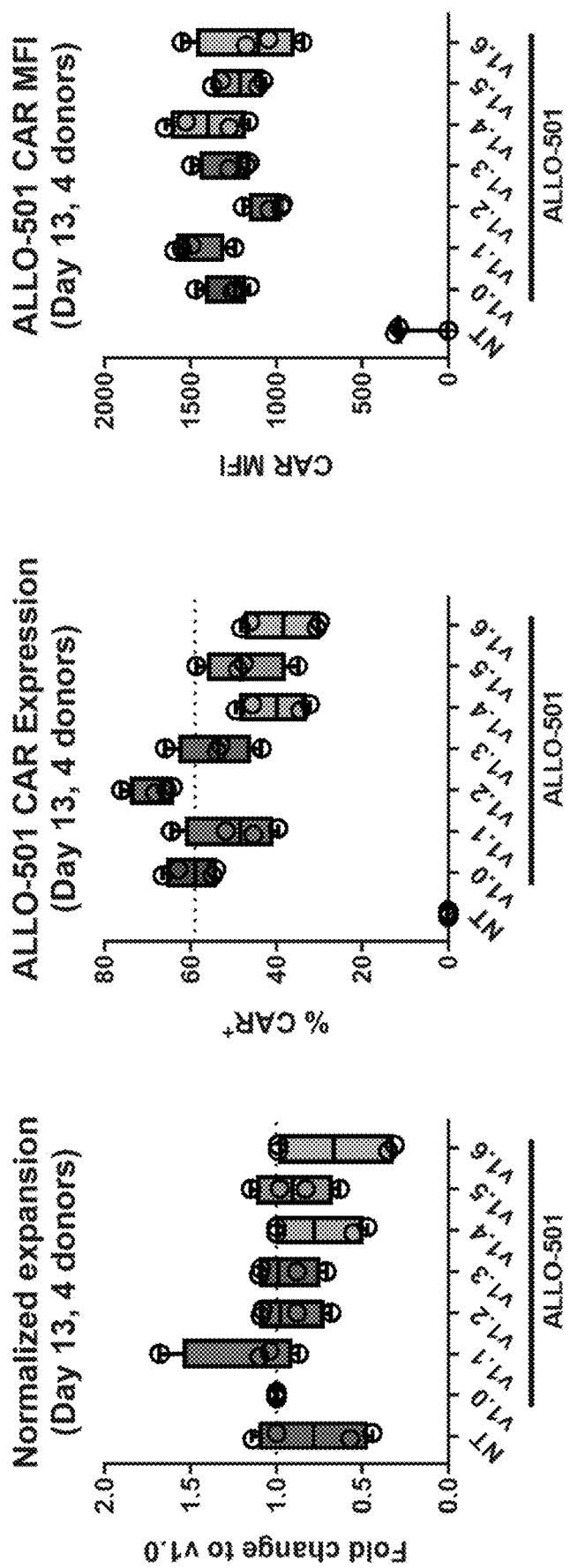
FIG. 3 shows normalized cell expansion and final CAR expression from all four donors on day 13.
Figure 4A:
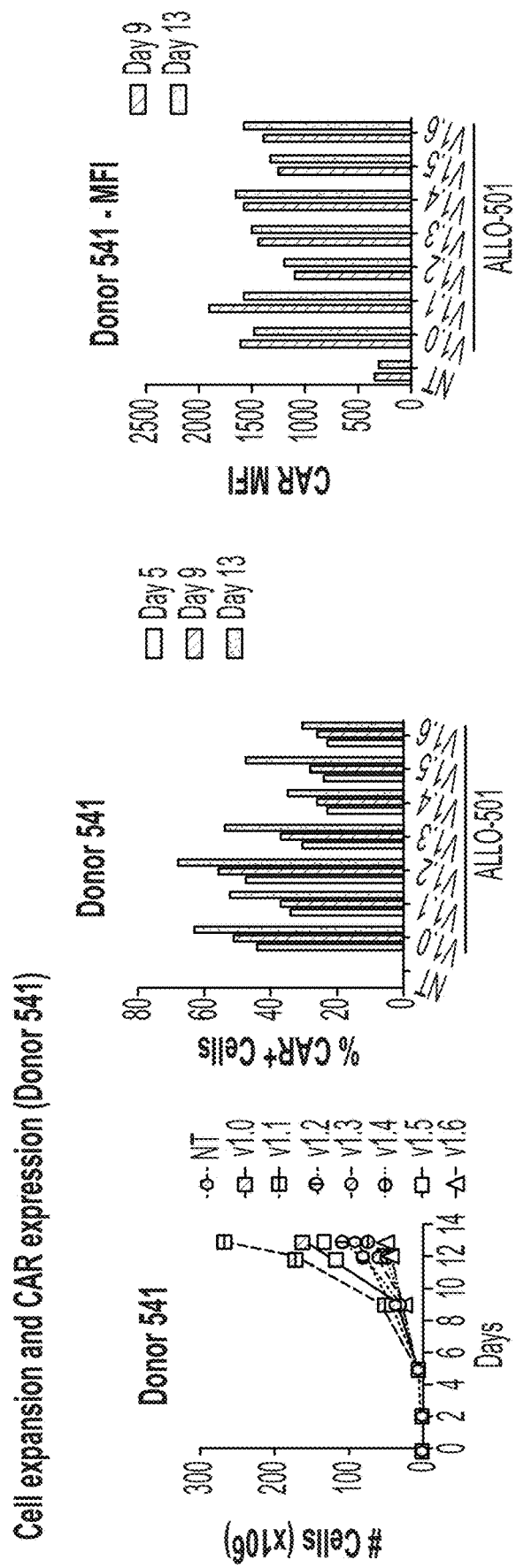
FIG. 4A-4D show cell expansion and CAR expression over time of Pan T cells from donor 541 (FIG. 4A), 604 (FIG. 4B), 410 (FIG. 4C), 2593 (FIG. 4D) transduced with rituximab resistant CAR expression vectors.
Figure 4B:
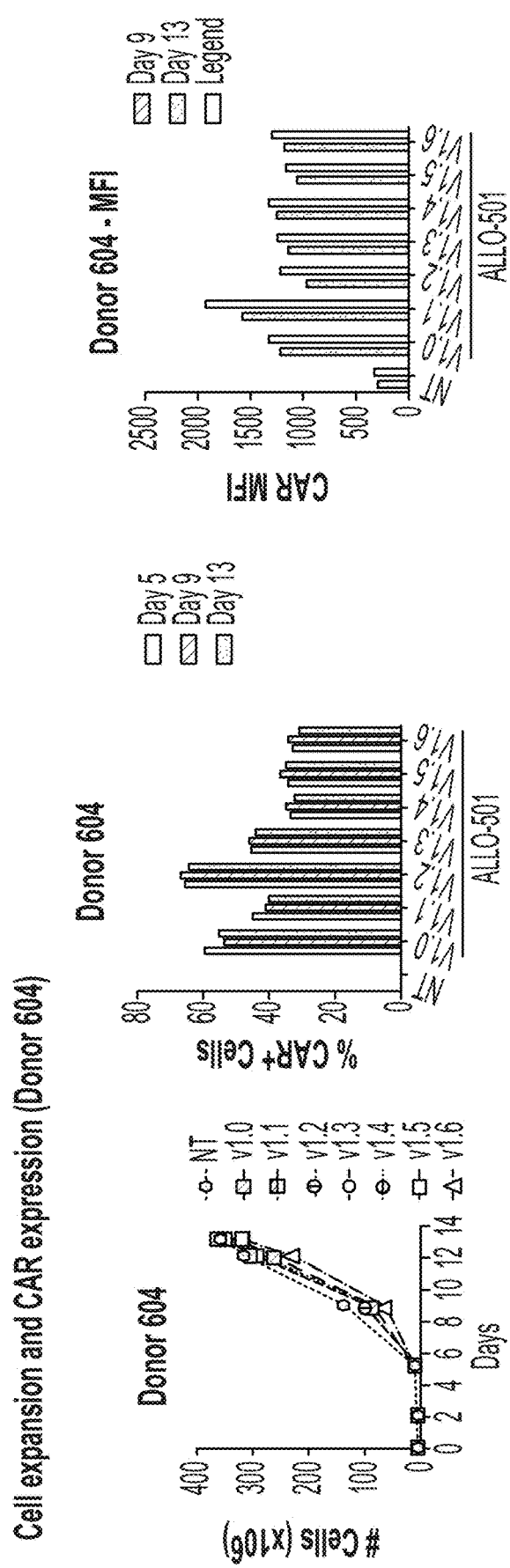
Figure 4C:
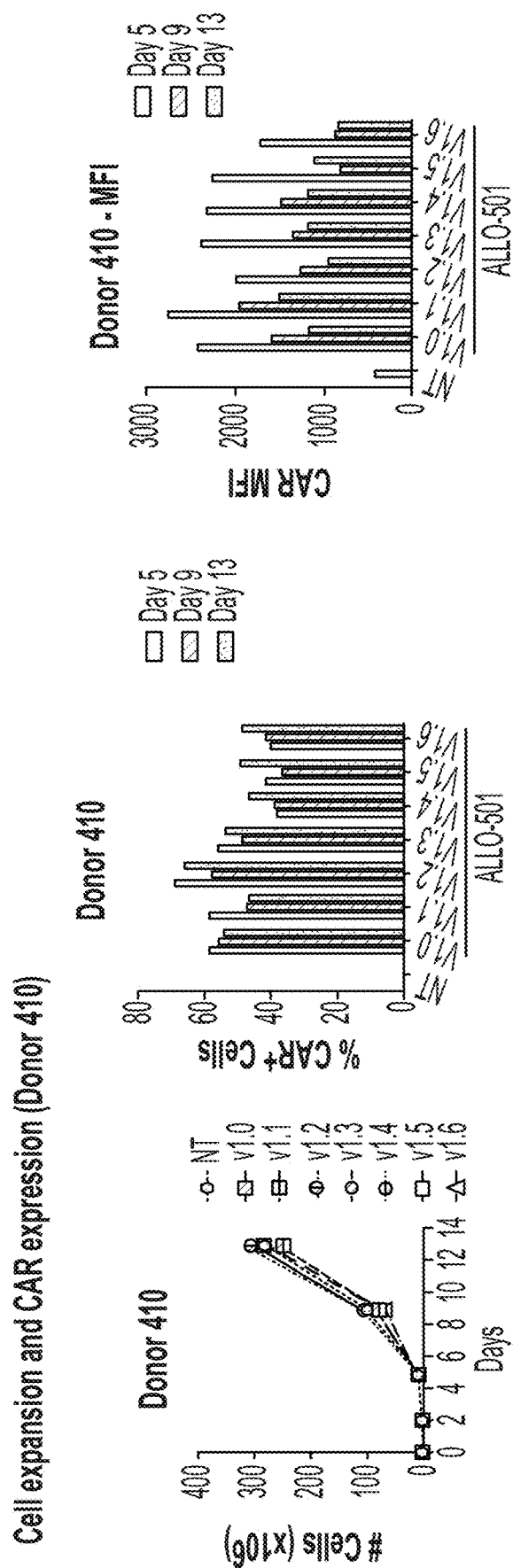
Figure 4D:
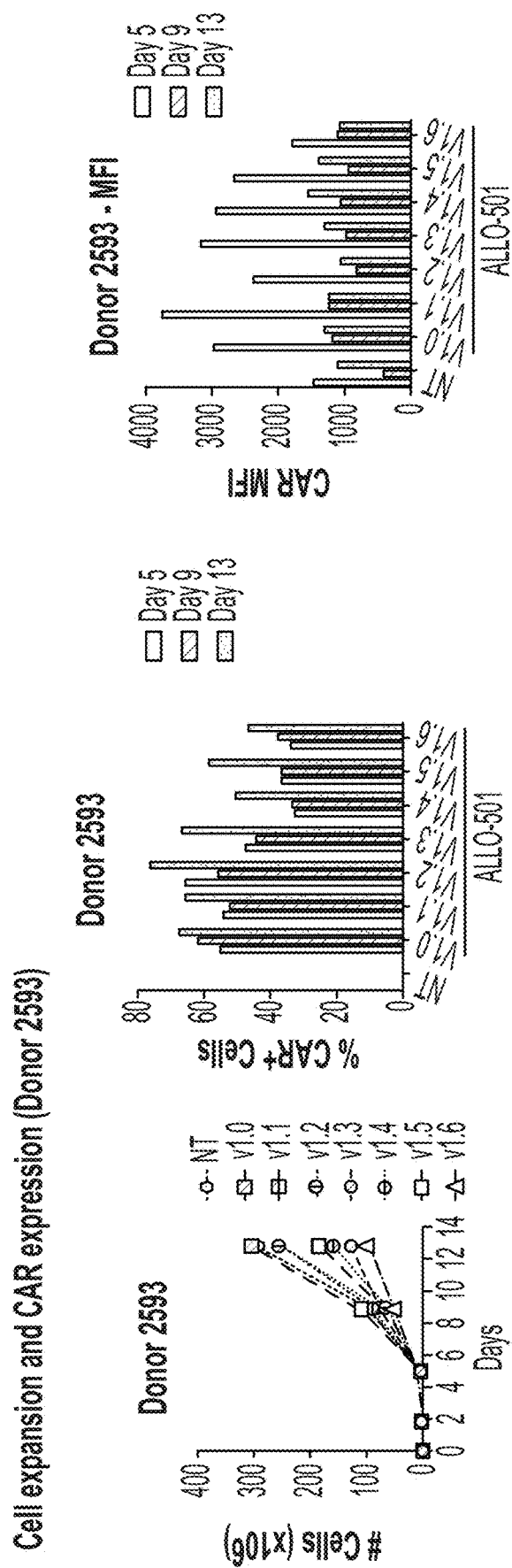

Flow cytometry with a human phenotype and activation panel was performed on day 9 and 13. The panel included CD3, CD4, CD8, viability, CD45RO, CD62L, CD25, 4-1BB, PD-1, an anti-idiotype to antibody to the anti-CD19 CAR, and TIM3. Cells were normalized for cell expansion and final CAR expression from all four donors on day 13 (FIG. 3). The data in FIG. 3 show that although v1.2 exhibited higher transduction rate (% CAR+), v1.2 transduced cells exhibited lower levels of CAR expression (CAR MFI), as compared to, e.g., v1.0 and v1.1. Cell expansion and CAR expression was monitored over time of the Pan T cells from donor 541 (FIG. 4A), 604 (FIG. 4B), 410 (FIG. 4C), 2593 (FIG. 4D) transduced with rituximab resistant CAR expression vectors.

Figure 5A:
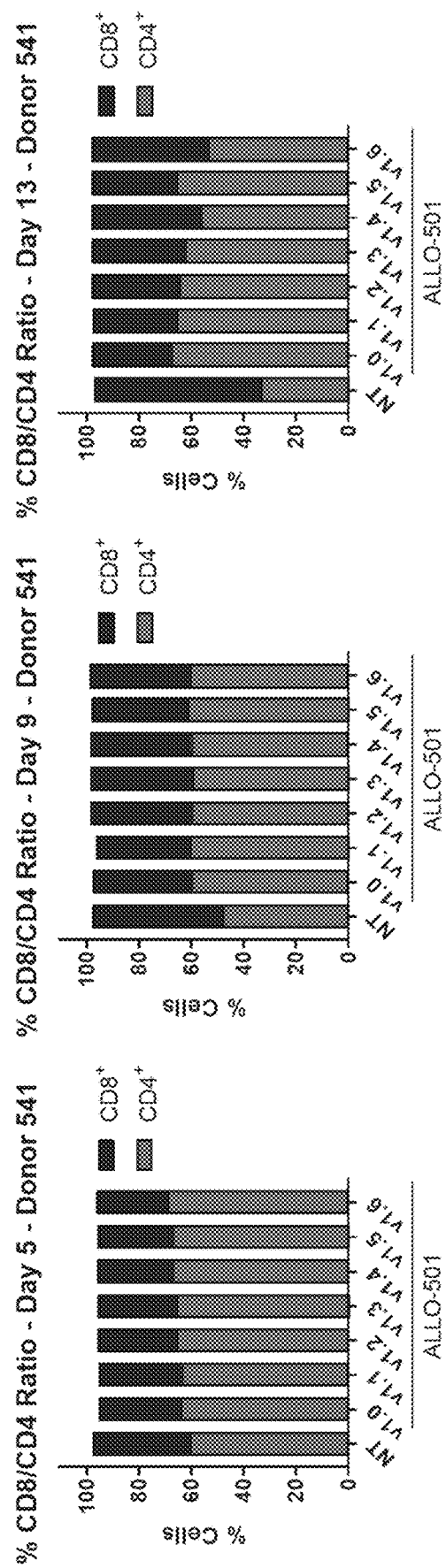
FIGS. 5A-5D show CD4/CD8 ratios on day 5, 9, and 13 of Pan T cells from donor 541 (FIG. 5A), 604 (FIG. 5B), 410 (FIG. 5C), 2593 (FIG. 5D) transduced with rituximab resistant CAR expression vectors.
Figure 5B:
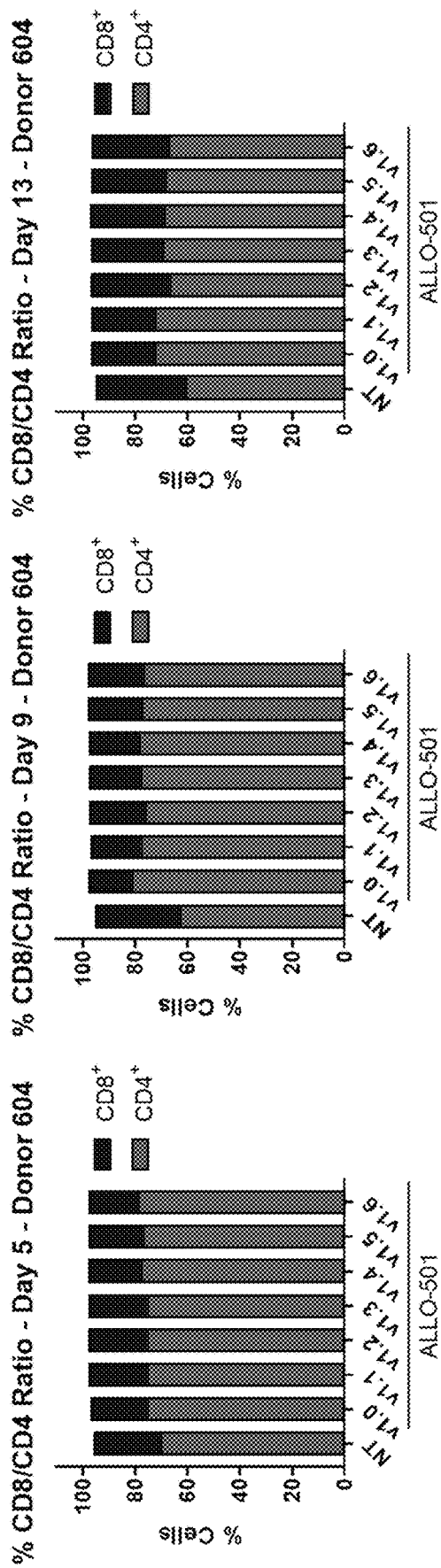
Figure 5C:
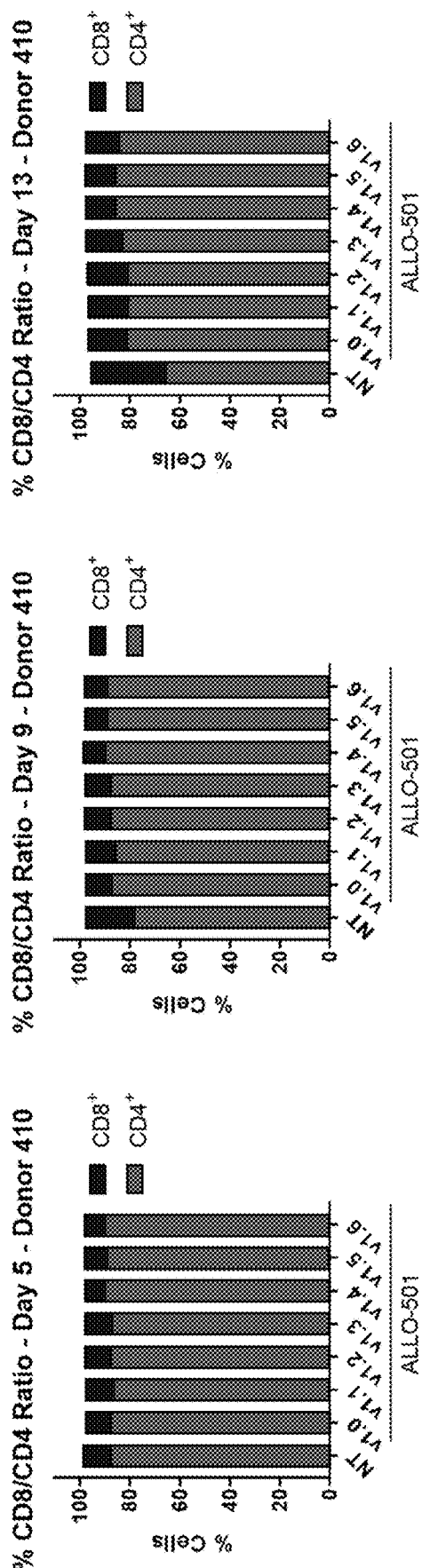
Figure 5D:
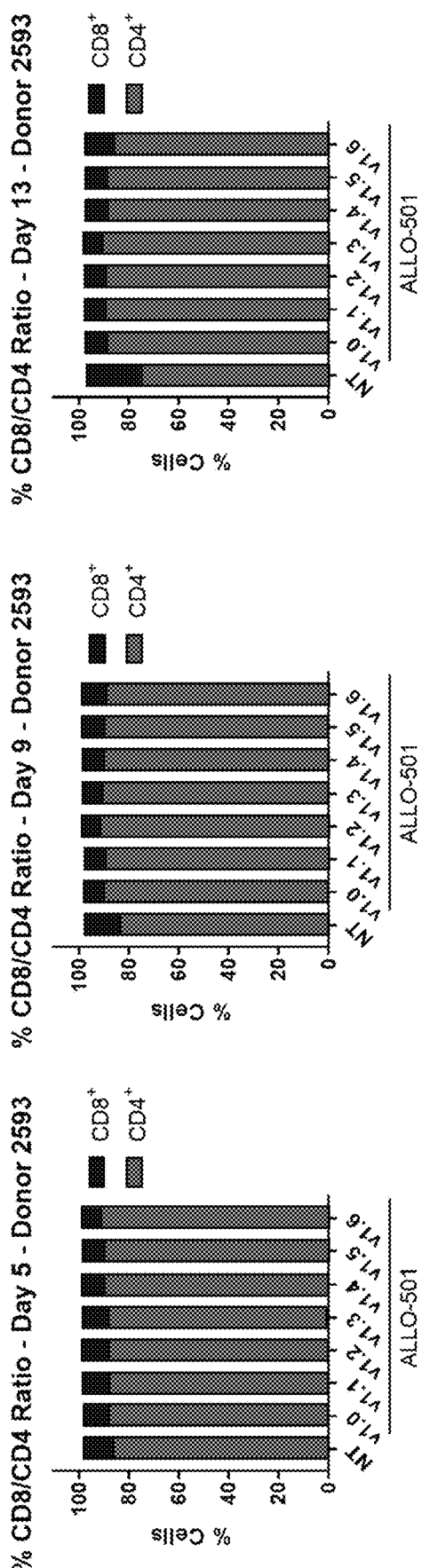
Figure 6A:
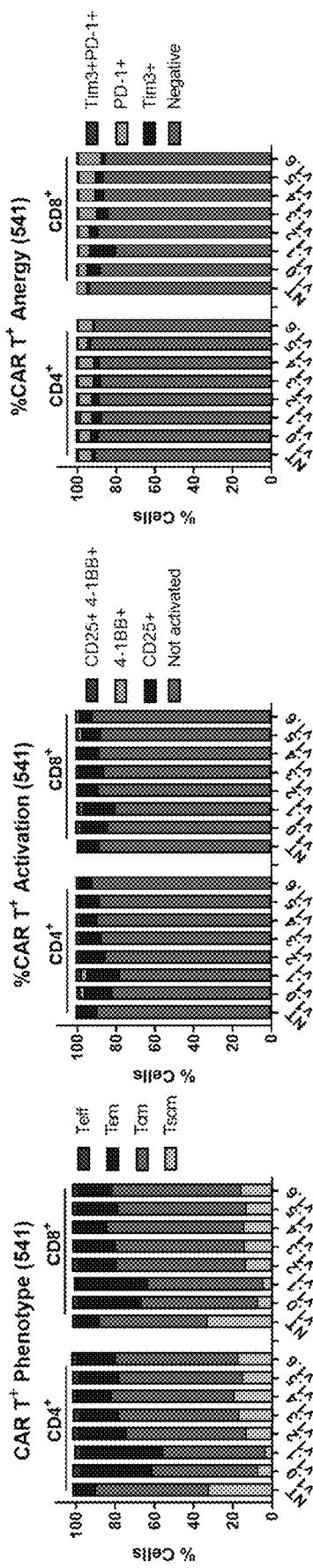
FIGS. 6A-6D show phenotype and activation on day 9 of Pan T cells from donor 541 (FIG. 6A), 604 (FIG. 6B), 410 (FIG. 6C), 2593 (FIG. 6D) transduced with rituximab resistant CAR expression vectors.
Figure 6B:
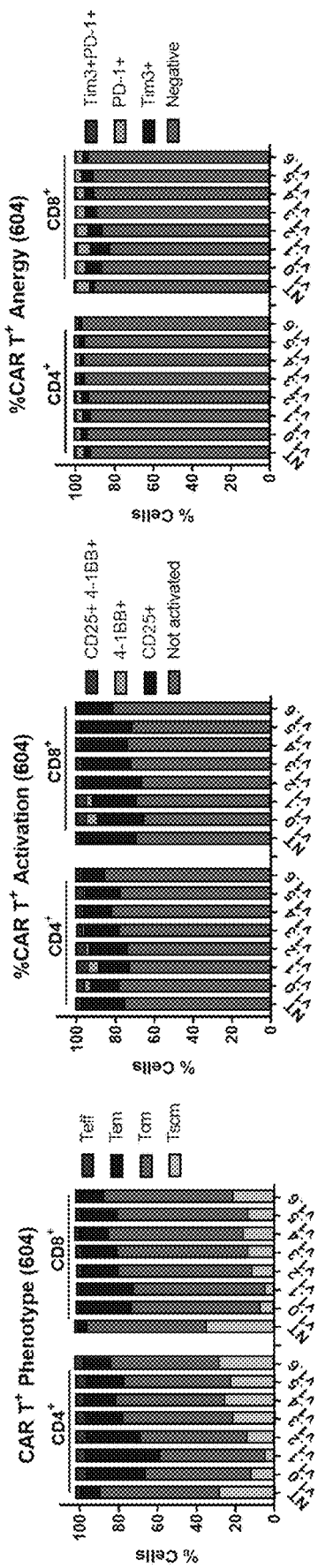
Figure 6C:
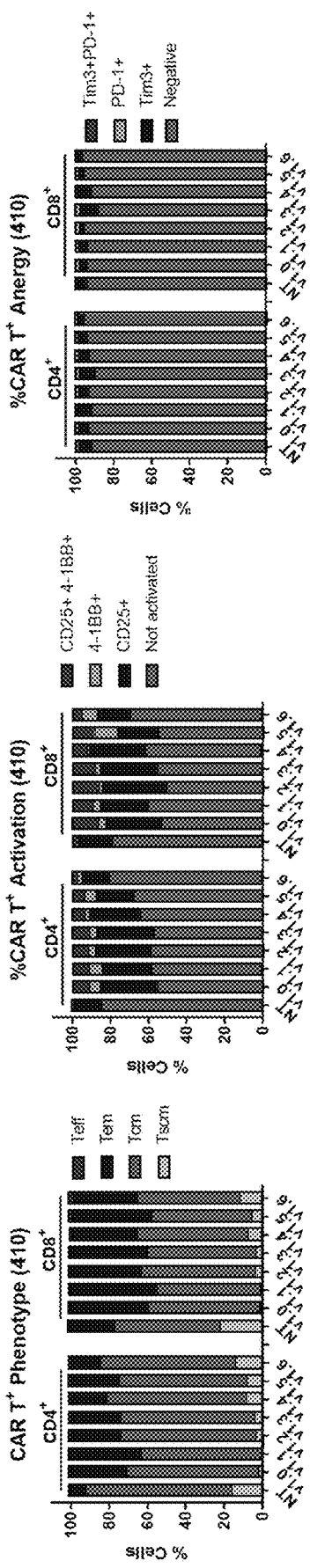
Figure 6D:
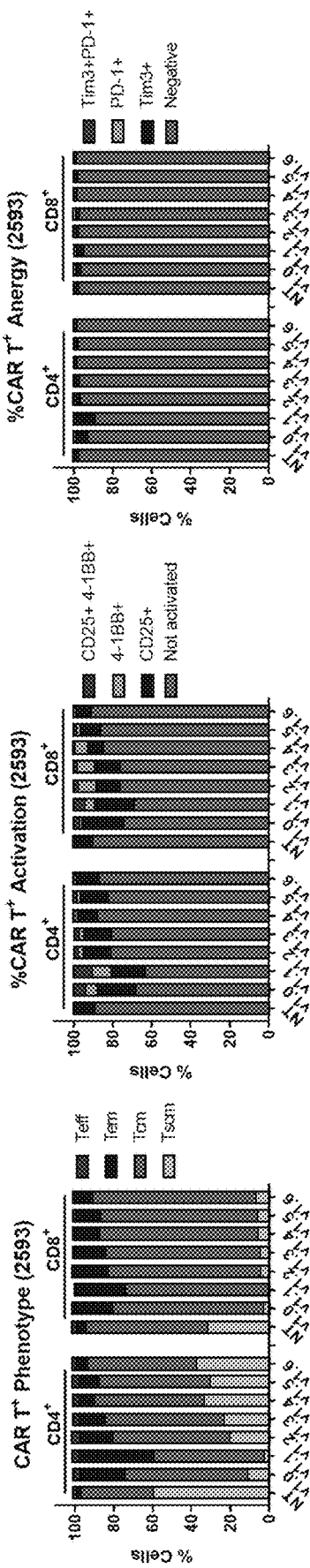
Figure 7:
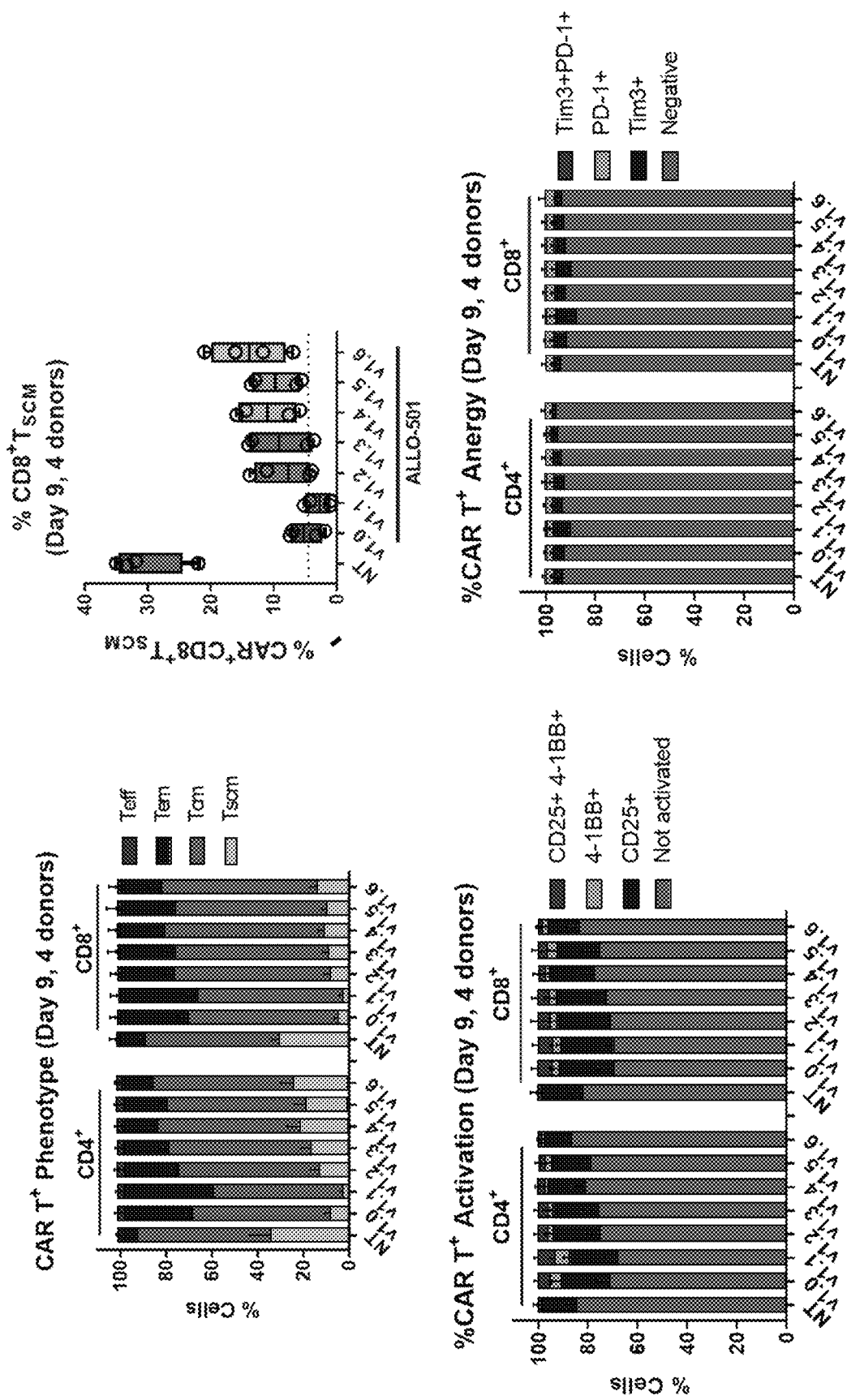
FIG. 7 shows phenotype, activation % CD8+, and anergy measured using TIM3 and PD1 staining averaged from all four donors on day 9.
Figure 8A:
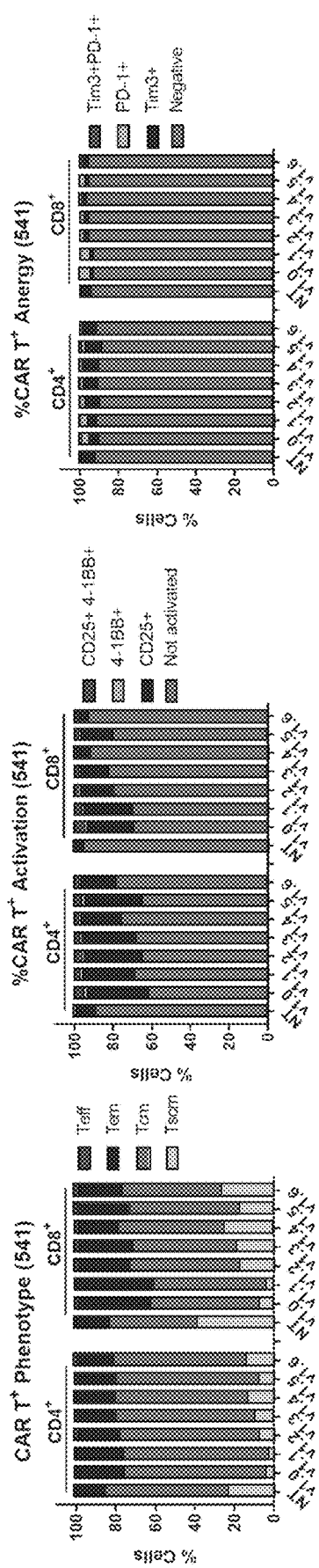
FIGS. 8A-8D show phenotype and activation on day 13 of Pan T cells from donor 541 (FIG. 8A), 604 (FIG. 8B), 410 (FIG. 8C), 2593 (FIG. 8D) transduced with rituximab resistant CAR expression vectors.
Figure 8B:
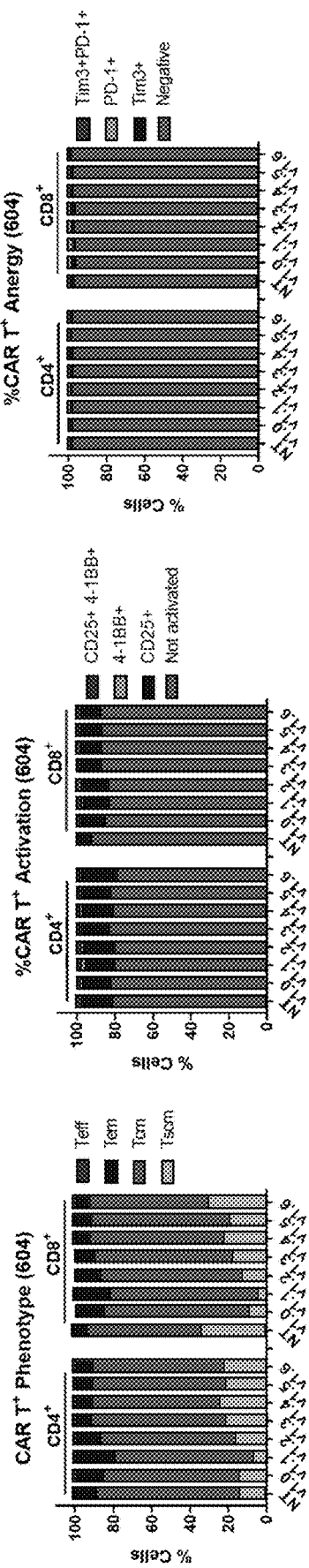
Figure 8C:
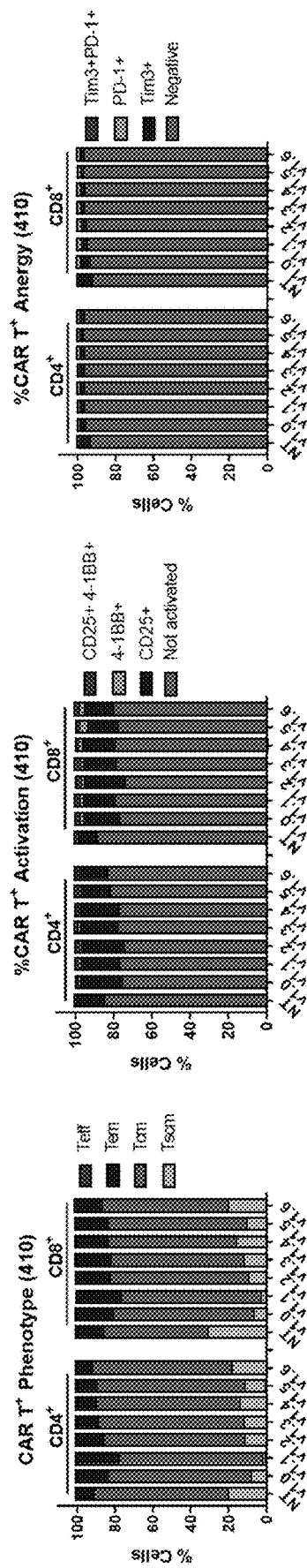
Figure 8D:
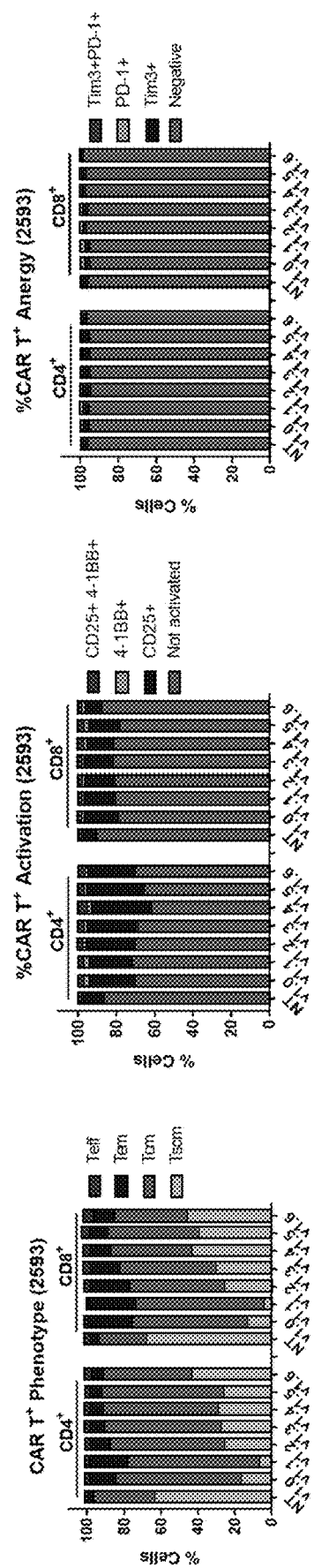
Figure 9:
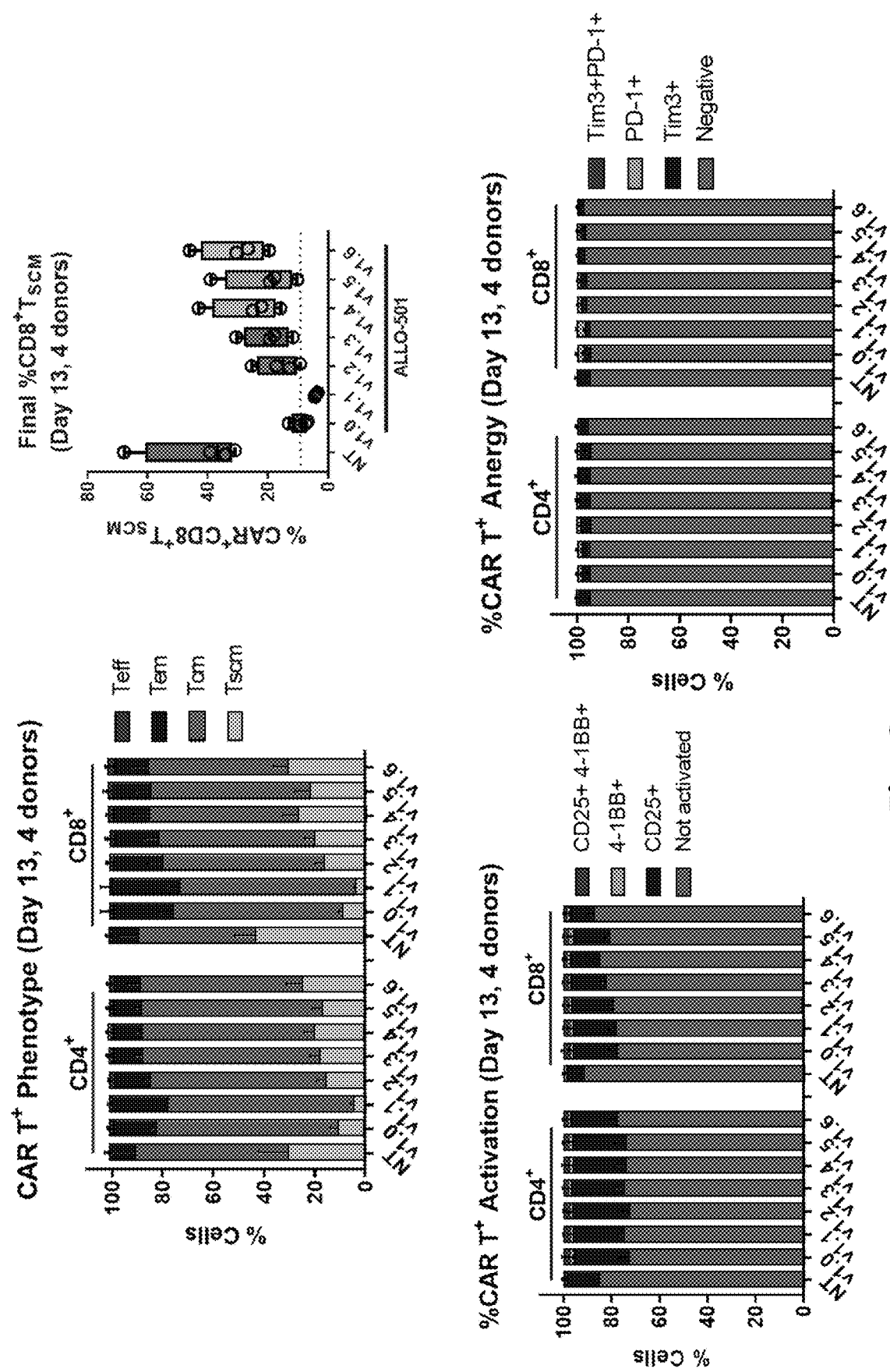
FIG. 9 shows phenotype, activation % CD8+, and anergy measured using TIM3 and PD1 staining from all four donors on day 13.

CD4/CD8 ratios were measured on day 5, 9, and 13 of Pan T cells from donor 541 (FIG. 5A), 604 (FIG. 5B), 410 (FIG. 5C), 2593 (FIG. 5D) transduced with rituximab resistant CAR expression vectors. FIGS. 6A-6D show phenotype and activation on day 9 of Pan T cells from donor 541 (FIG. 6A), 604 (FIG. 6B), 410 (FIG. 6C), 2593 (FIG. 6D) transduced with rituximab resistant CAR expression vectors. FIG. 7 shows phenotype, activation % CD8+, and T cell anergy measured using TIM3 and PD1 staining averaged from all four donors on day 9. Phenotype and activation were measured on day 13 of Pan T cells from donor 541 (FIG. 8A), 604 (FIG. 8B), 410 (FIG. 8C), 2593 (FIG. 8D) transduced with rituximab resistant CAR expression vectors. FIG. 9 shows phenotype, activation % CD8+, and T cell anergy measured using TIM3 and PD1 staining from all four donors on day 13.

Example 2: Short- and Long-Term In Vitro Killing Assays

Figure 10:
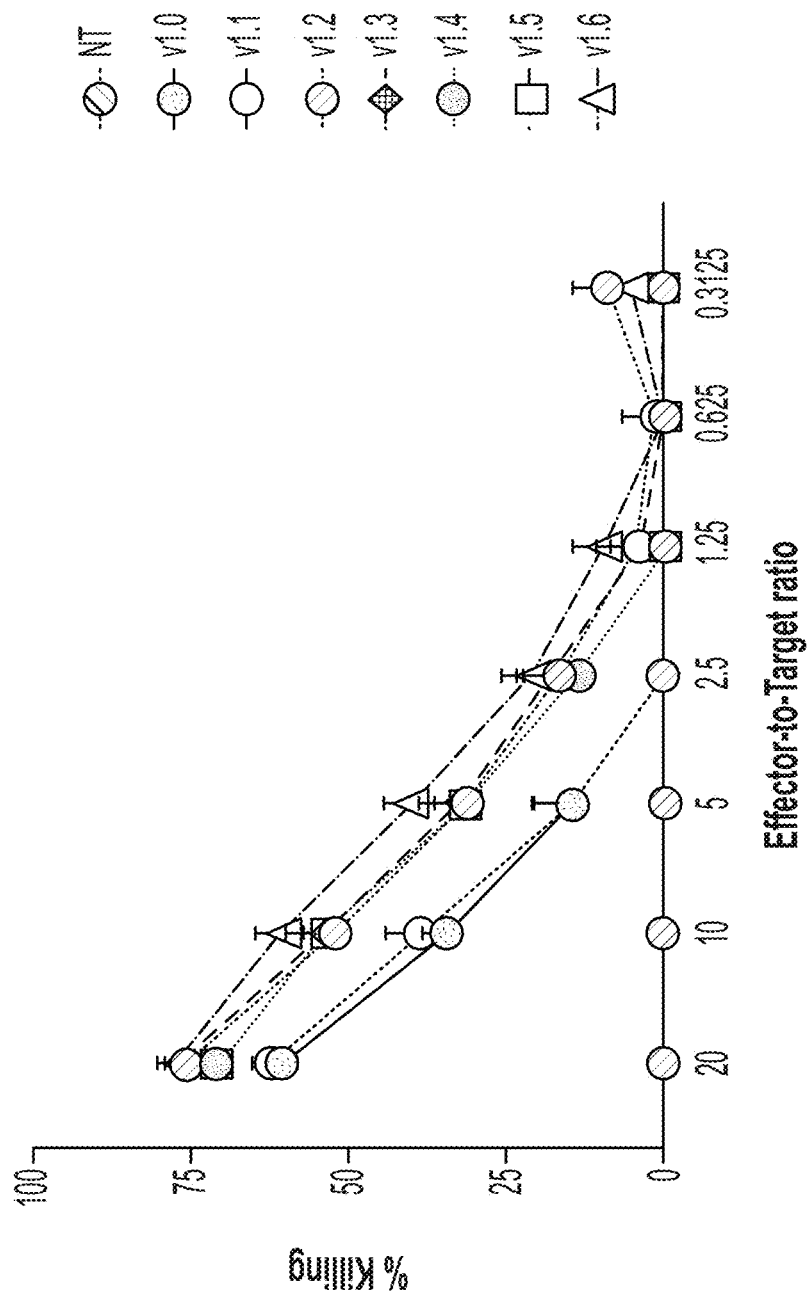
FIG. 10 shows average short-term (24 hr) killing assays using Raji cells as target cells for each CAR construct.
Figure 11B:
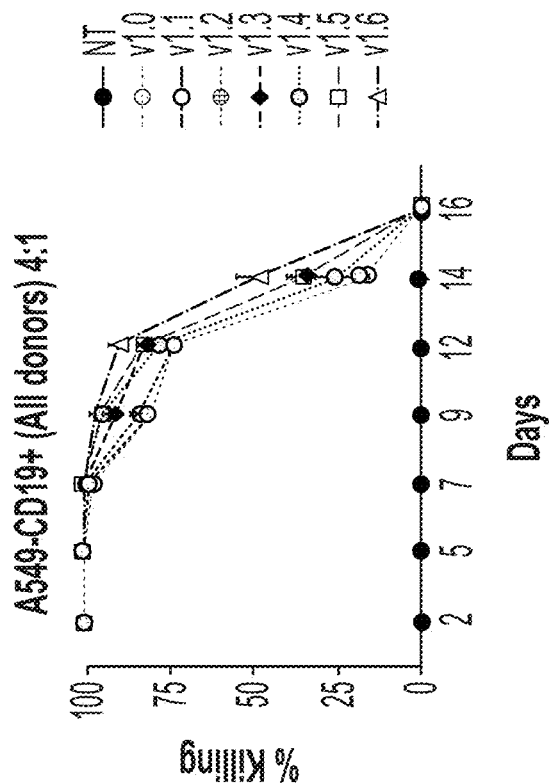
FIGS. 11A-11D shows average long-term killing assays using A549-CD19+ cells as target cells with an E:T of 8:1 (FIG. 11A), 4:1 (FIG. 11B), 2:1 (FIG. 11C), and 1:1 (FIG. 11D) for each CAR construct.
Figure 11A:
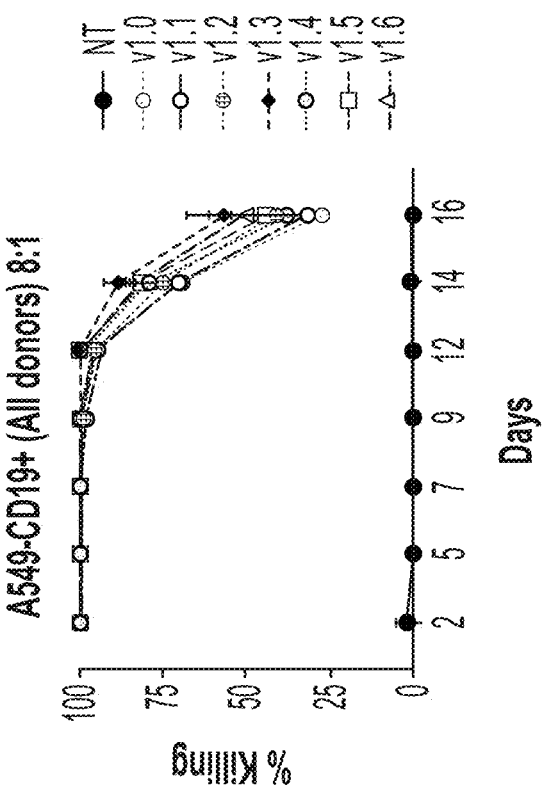
Figure 11D:
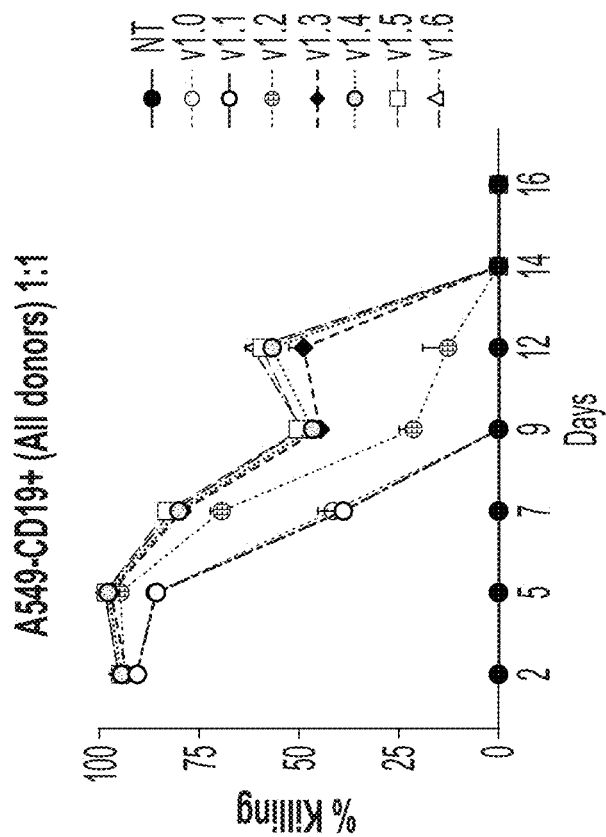
Figure 11C:
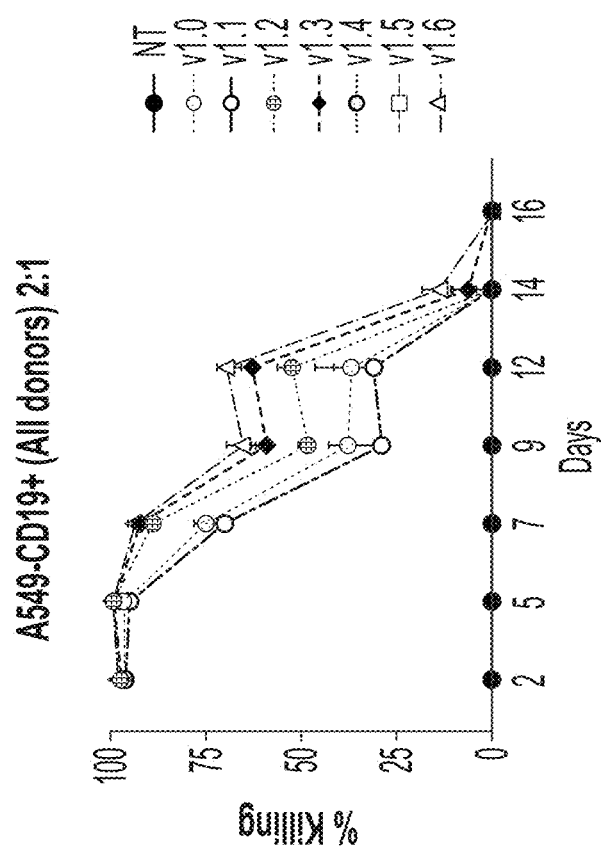

Transduced CAR cells from Example 1 were tested for short- and long-term killing capabilities. CAR T cell co-cultures with Raji cells (2:1 E-to-T) were prepared for posterior a Luminex assay. Average short-term (24 hr) killing assays using Raji cells as target cells was determined for each CAR construct (FIG. 10). FIGS. 11A-11D shows average long-term killing assays using A549-CD19+ cells as target cells with an E:T of 8:1 (FIG. 11A), 4:1 (FIG. 11B), 2:1 (FIG. 11C), and 1:1 (FIG. 11D) for each CAR construct.

Killing assay results were analyzed for correlation with phenotypic characteristics. Day 7 percent killing at 1:1 E-to-T negatively correlates with CAR+CD4+41BB+, CAR+CD4+Tim3+ (p=0.0352), CAR+CD4+$T_{EM}$+ (p=0.0328), CAR+CD8+PD-1+(p=0.0269) and % CAR expression on day 13 (p=0.0245). Day 7 percent killing at 1:1 E-to-T positively correlates with CAR+CD8+$T_{SCM}$+. Day 9 percent killing at 1:1 E-to-T negatively correlates with CAR+CD4+Tim3+, CAR+CD4+$T_{EM}$+ (p=0.0031), CAR+CD8+$T_{cm}$+ (p=0.0182) and % CAR expression day 13 (p=0.0469). Day 9 percent killing at 1:1 E-to-T positively correlates with CAR+CD8+$T_{SCM}$+, CAR+CD8+Tim3-PD-1-(p=0.0318), and CAR+CD4+$T_{SCM}$+ (p=0.0289).

Example 3: Analysis of Titers of Lentivirus Containing Different Lentiviral Constructs In this experiment, the lentiviral vectors constructs were introduced into viral packaging cell line and anti-CD19 CAR containing lentiviruses were produced and titers determined at Lentigen (Gaithersberg, MD) under a similar protocol as in Example 1.

To lentiviral titers were assessed either by measuring the physical titers of the levels of viral protein p24 or by measuring the transducing titers. It was unexpectedly found that when the safety switch RQR8 was removed from the lentiviral construct v1.0, viral titer significantly decreased (compare v1.0 with v1.1 in Table 5). The titer was improved when the EF1α promoter in v1.1 was replaced with a short or truncated EF1α promoter as in v1.2 ("EF1a(short) promoter").

TABLE 5

Viral Titers of lentivirus bearing rituximab-sensitive and -resistant CD19 CAR constructs

| Construct | Physical titer p24 | Transducing titer |
|---|---|---|
| anti-CD19 CAR v1.0 | 9293 ng/mL | $1.9 \times 10^9$ TU/mL[1] |
| anti-CD19 CAR v1.1 | 2464 ng/mL | $5.4 \times 10^8$ TU/mL |
| anti-CD19 CAR v1.2 | 8208 ng/mL | $7 \times 10^9$ TU/mL |
| anti-CD19 CAR v1.3 | 4494 ng/mL | $7 \times 10^8$ TU/mL |
| anti-CD19 CAR v1.4 | 9686 ng/mL | $2.4 \times 10^9$ TU/mL |

[1]TU = Transducing Unit

Figure 12:
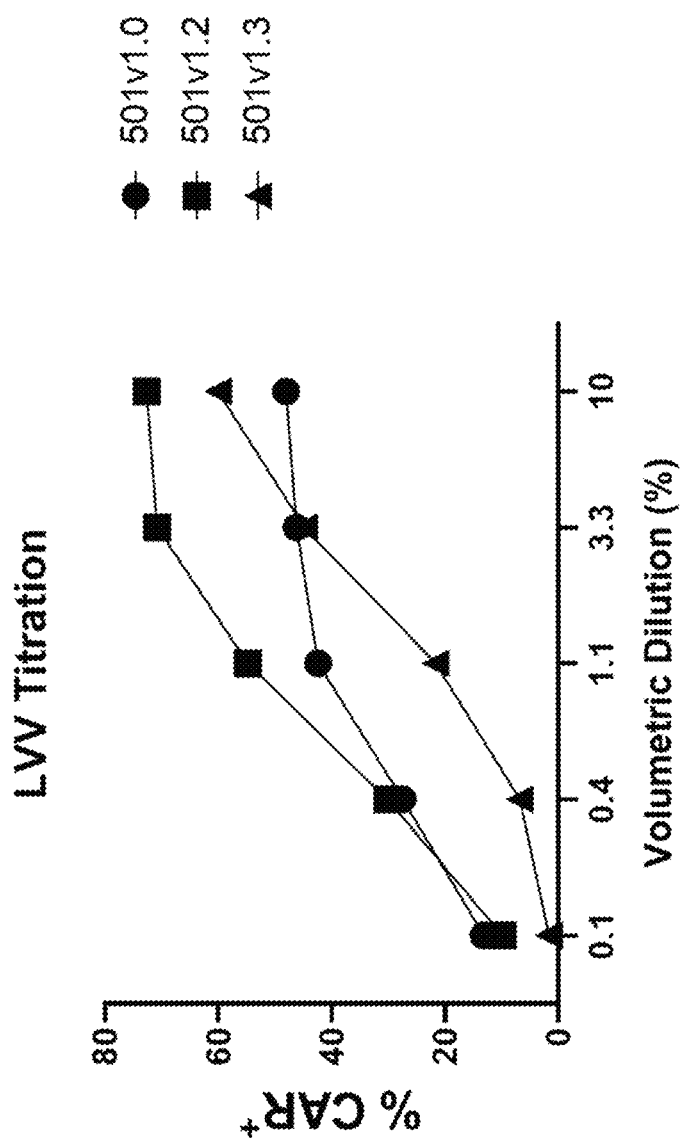
FIG. 12 shows the level of % CAR+ T cells on Day 5 after Pan T cells were transduced with serial dilution of lentiviral preparations of rituximab-resistant lentiviral constructs (ALLO-501v1.2 and v1.3) or rituximab-sensitive lentiviral construct (ALLO-501v1.0).

To analyze the robustness of the lentiviral preparations of anti-CD19 CAR v1.0, v1.2 and v1.3, a viral titration assay was performed. Serial volumetric dilution of lentiviral preparations of v1.0, v1.2 and v1.3 was analyzed for % CAR+ T cells on Day 5 after transduction of pan T cells. The results show that at low dilution (e.g., 10% v/v), all three constructs exhibited similar acceptable transduction efficiency. At increasing dilutions (e.g., 3.3%, 1.1% v/v), however, the transduction efficiency of rituximab-resistant anti-CD19 CAR construct v1.3 dropped more significantly as compared to the other rituximab-resistant anti-CD19 CAR construct v1.2. See FIG. 12. Construct v1.2 was selected for in vivo analysis.

Example 4: In Vivo Potency Assay

Figure 13A:
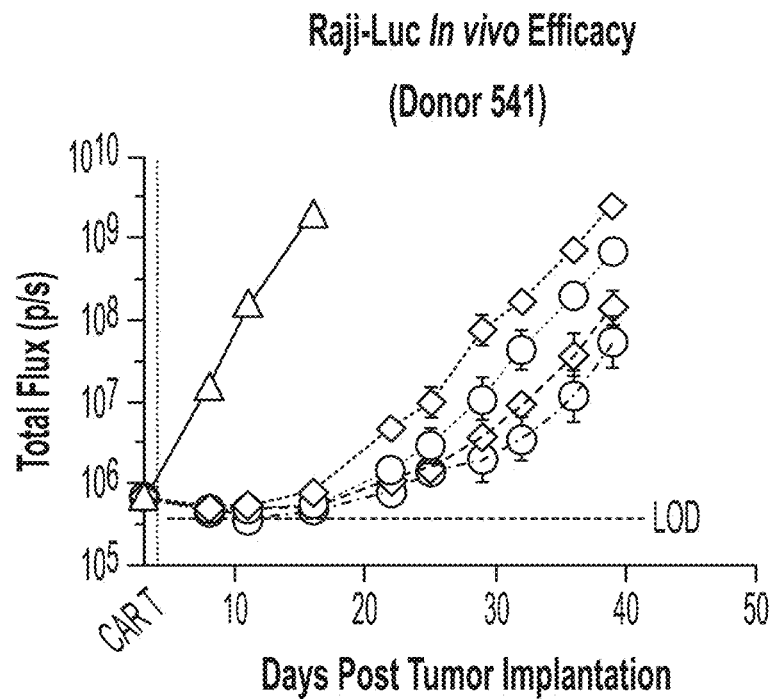
FIGS. 13A-13B show in vivo efficacy of pan T cells from donors 541 (FIG. 13A) and 604 (FIG. 13B) transduced with rituximab-resistant CAR expression vector (ALLO-501v1.2) or rituximab-sensitive CAR expression vector (ALLO-501v1.0) when tested in a Raji cells-bearing NSG mouse tumor model.
Figure 13B:
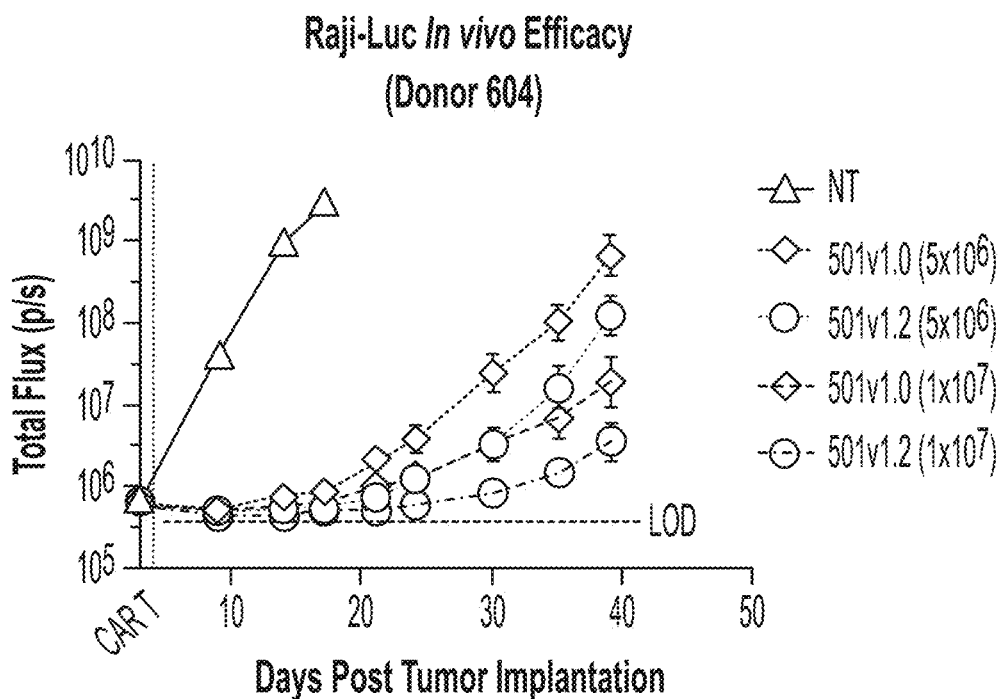

In this experiment, in vivo anti-tumor potency of ALLO-501v1.2 was analyzed as compared to ALLO-501v1.0 in a mice tumor model. CD19 positive Raji cells that carry a luciferase reporter gene were injected into NSG mice. Lentivirus containing the v1.0 or v1.2 lentiviral construct was transduced to pan T cells of two donors 541 and 604. NSG mice were inoculated via tail vein injection with 100,000 luciferase Raji cells. On day 4 post-inoculation Raji-bearing NSG mice were administered the CAR construct at the indicated doses. Raji engraftment and progression was evaluated by i.p. injection of luciferase substrate, followed by measurement of cumulative luciferase signals. Results are shown in FIG. 13A (donor 541) and FIG. 13B (donor 604).

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

| SEQ ID NO. CHART | | |
|---|---|---|
| SEQ ID NO | Description | Sequence |
| 1 | ALLO-501_v1.0 | atgctgaccagcctgctgtgctggatggccctgtgcctgctgggcgccgaccacg ccgatgcctgcccctacagcaacccagcctgtgcagcggaggcggcggcagc gagctgcccaccagggcaccttctccaacgtgtccaccaacgtgagcccagcc aagcccaccaccaccgcctgtccttattccaatccttccctgtgtagcggaggggg aggcagccagccccagacctcccaccccagccccaccatcgccagccagc ctctgagcctgagacccgaggcctgccgcccagccgccggcggcgccgtgcac accagaggcctggatttcgcctgcgatatctacatctgggcccactggccggca cctgtggcgtgctgctgctgagcctggtgatcaccctgtactgcaaccaccgcaac cgcaggcgcgtgtgcaagtgccccaggcccgtggtgagagccgagggcagag gcagcctgctgacctgcggcgacgtggaggagaacccaggccccatggagacc gacaccctgctgctgtgggtgctgctgctgtgggtgccaggcagcaccggcgag gtgcagctgcagcagagcggacccgagctgatcaagccaggcgccagcgtgaa gatgagctgcaaggccagcggctacaccttcaccagctacgtgatgcactgggtg aagcagaagccaggccagggcctggagtggatcggctacatcaaccctacaac gacggcaccaagtacaacgagaagttcaagggcaaggccaccctgaccagcga caagagcagcagcaccgcctacatggagctgagcagcctgaccagcgaggaca gcgccgtgtactactgcgccagaggcacctactactacggcagccgggtgttcga ctactggggccagggcaccaccctgaccgtgagctctggcggaggcggctctgg cggaggcggctctggcggaggcggcagcgacatcgtgatgacccaggctgccc ccagcatccccgtgaccccaggcgagagcgtgagcatcagctgccggagcagc aagagcctgctgaacagcaacggcaacacctacctgtactggttcctgcagcggc caggccagagccccagctgctgatctaccggatgagcaacctggccagcggc gtgcccgaccggttcagcggcagcggcagcggcaccgccttcaccctgcggatc agccgggtggaggccgaggacgtgggcgtgtactactgcatgcagcacctgga gtacccatcaccttcggagccggcaccaagctggagctgaagcggtcggatccc accaccaccccagcccacggccacctaccctgccccaaccatcgccagcca gcccctgagcctgcggcctgaagcctgcaggcctgccgccggaggagccgtgc acacaaggggcctggacttcgcctgcgacatctatatctgggcccccctggccgg gacatgcggggtgctgctgctgtccctggtgattacactgtattgcaaacgggcc ggaagaagctgctgtacatcttcaagcagccctcatgcggcccgtgcagaccac ccaggaggaggacggctgcagctgccggttccccgaggaagaggaaggcggc tgcgagctgcgggtgaagttcagccggagcgccgacgcccagcctaccagca gggccagaaccagctgtacaacgagctgaacctgggacggcgggaggagtac gacgtgctggacaagcggcggggacgggaccccgagatgggcggcaagcctc gccggaagaatccccaggagggcctgtacaacgagctgcagaaggacaagatg gccgaggcctacagcgagatcggcatgaagggcgagcggcgccggggcaag ggccacgacggcctgtaccagggcctgagcaccgccaccaaggacacctacga cgccctgcacatgcaggccctgccaccccggtga |
| 2 | ALLO-501_v1.1 | atggagaccgacacccctgctgctgtgggtgctgctgctgtgggtgccaggcagca ccggcgaggtgcagctgcagcagagcggacccgagctgatcaagccaggcgc cagcgtgaagatgagctgcaaggccagcggctacaccttcaccagctacgtgatg cactgggtgaagcagaagccaggccagggcctggagtggatcggctacatcaa ccctacaacgacggcaccaagtacaacgagaagttcaagggcaaggccaccct gaccagcgacaagagcagcagcaccgcctacatggagctgagcagcctgacca gcgaggacagcgccgtgtactactgcgccagaggcacctactactacggcagcc gggtgttcgactactggggccagggcaccaccctgaccgtgagctctggcggag gcggctctggcggaggcggctctggcggaggcggcagcgacatcgtgatgacc caggctgcccccagcatccccgtgaccccaggcgagagcgtgagcatcagctg ccggagcagcaagagcctgctgaacagcaacggcaacacctacctgtactggtt cctgcagcggccaggccagagccccagctgctgatctaccggatgagcaacct |

-continued

SEQ ID NO. CHART

| SEQ ID NO | Description | Sequence |
|---|---|---|
| | | ggccagcggcgtgcccgaccggttcagcggcagcggcagcggcaccgccttca ccctgcggatcagccgggtggaggccgaggacgtgggcgtgtactactgcatgc agcacctggagtacccccttcaccttcggagccggcaccaagctggagctgaagc ggtcggatcccaccaccacccagccccacggccacctaccccctgccccaacca tcgccagccagccccctgagcctgcggcctgaagcctgcaggcctgccgccgga ggagccgtgcacacaaggggcctggacttcgcctgcgacatctatatctgggccc ccctggccgggacatgcggggtgctgctgctgtccctggtgattacactgtattgc aaacggggccggaagaagctgctgtacatcttcaagcagcccttcatgcggcccg tgcagaccacccaggaggaggacggctgcagctgccggttccccgaggaagag gaaggcggctgcgagctgcgggtgaagttcagccggagcgccgacgccccag cctaccagcagggccagaaccagctgtacaacgagctgaacctgggacggcgg gaggagtacgacgtgctggacaagcggcggggacgggaccccgagatgggcg gcaagcctcgccgaagaatccccaggagggcctgtacaacgagctgcagaag gacaagatggccgaggcctacagcgagatcggcatgaagggcgagcggcgcc ggggcaagggccacgacggcctgtaccagggcctgagcaccgccaccaagga cacctacgacgccctgcacatgcaggccctgccaccccggtga |
| 3 | ALLO-501_v1.2 | atggagacagataccctgctgctgtgggtgctgctgctgtgggtgcctggctccac aggagaggtgcagctgcagcagtctggaccagagctgatcaagcctggagcatc cgtgaagatgtcttgcaaggccagcggctatacattcaccagctacgtgatgcact gggtgaagcagaagcctggccagggcctggagtggatcggctatatcaatccata caacgacggcaccaagtataatgagaagtttaagggcaaggccacactgacctct gataagagctcctctacagcctacatggagctgagctccctgacctctgaggacag cgccgtgtactattgcgccagaggcacatactattacggcagcagggtgttcgatt actggggccagggcaccacactgaccgtgtctagcggaggaggaggctccgga ggaggaggctctggcggcggcggcagcgacatcgtgatgacacaggcagcac caagcatcccagtgaccctggcgagagcgtgtccatctcttgtcggtcctctaagt ccctgctgaactctaatggcaacacctatctgtactggtttctgcagcggcccggac agtccccacagctgctgatctataggatgagcaacctggcatccggagtgcctgat cgcttcagcggctccggctctggaacagccttacctgaggatctctcggtgga ggcagaggacgtgggcgtgtattactgcatgcagcacctggagtaccccttcacat tggcgcaggaaccaagctggagctgaagcggagcgaccccaccacaaccct gcaccacgcccctacaccagcacctaccatcgcatctcagccactgagcctgc ggcccgaggcctgtaggcctgcagcaggaggagcagtgcacaccaggggcct ggacttcgcctgcgatatctatatctgggcaccactggcaggaacatgtggcgtgc tgctgctgagcctggtcatcaccctgtattgcaagagaggcaggaagaagctgct gtacatcttcaagcagccttttatgcggccagtgcagacaacccaggaggaggat ggctgctcctgtagattcccagaggaggaggagggaggatgtgagctgcgcgtg aagtttagccggtccgccgacgcaccagcatatcagcagggccagaatcagctgt acaatgagctgaacctgggccggagagaggagtacgacgtgctggataagagg aggggaagggaccccgagatgggaggcaagccacggagaaagaatccccag gagggcctgtataacgagctgcagaaggataagatggccgaggcctacagcga gatcggcatgaagggagagaggcgccggggcaagggacacgacggcctgtat cagggcctgtccacagccaccaaggacacctacgatgccctgcacatgcaggcc ctgccaccaaggtga |
| 4 | ALLO-501_v1.3 | atgggaacaagcctgctgtgctggatggctctgtgcctgctggggggccgaccacg ctgacgcctccggggggggggggctcctgccccctaggccccctacacctgcac caaccatcgcatcccagccactgtctctgcgccctgaggcctgccggccagcagc aggaggagcagtgcacacccgcggcctggacttcgcctgcgatatctatatctgg gcaccactggcaggcacatgtggcgtgctgctgctgagcctggtcatcaccctgta ctgcaatcacaggaaccggagaagggtgtgcaagtgtccccggcctgtggtgag agcagagggaaggggcagcctgctgacatgtggcgacgtggaggagaatccag gccctatggagacagataccctgctgctgtgggtgctgctgctgtgggtgcccgg cagcaccgggagagtgcagctgcagcagtccggaccagagctgatcaagcctg gagccagcgtgaagatgtcctgtaaggcctctggctatacattcaccagctacgtg atgcactgggtgaagcagaagcctggccagggcctggagtggatcggctatatc aatccatacaacgacggcacaaagtataacgagaagtttaagggcaaggccaca ctgacctccgataagagctcctctacagcctacatggagctgagctccctgacctct gaggacagcgccgtgtactattgcgccagaggcacatactattacggctctagggt gttcgattactggggccagggcaccacactgaccgtgtctagcggaggaggagg cagcggaggaggaggctccggcggcggcggctctgacatcgtgatgacacagg cagcaccatccatcccagtgaccctggcgagagcgtgtccatctcttgtcggtcc tctaagcctgctgaactccaatggcaacacctatctgtactggtttctgcagcggg cccggacagagcccacagctgctgatctataggatgtctaatctggcaagcggcg tgcccgatcgcttcagcggctccggctctggcacagccttaccctgaggatctcc cgcgtggaggcagaggacgtgggcgtgtattactgcatgcagcacctggagtac cccttcacatttggcgcaggcaccaagctggagctgaagcggagcgaccccacc acaaccctgcaccacgcccacaccagcacctactattgcatcccagccac tgagcctgcggcccgaggcctgtaggcctgccgccggcggcgcagtgcacacc cggggcctggacttttgcctgcgatatctacatctgggcacctctggccggcacatg cggcgtgctgttactgagcctggtcatcaccctgtattgcaagcggggcagaaag aagctgctgtacatcttcaagcagccttttatgcggccagtgcagacaacccagga ggaggatggctgctcctgtagattcccagaggaggaggagggaggatgtgagct |

SEQ ID NO. CHART

| SEQ ID NO | Description | Sequence |
|---|---|---|
| | | gcgcgtgaagtttagccggtccgccgacgcaccagcatatcagcagggccagaa
ccagctgtacaatgagctgaacctgggccggagagaggagtatgacgtgctgga
taagagacggggccgggaccccgagatgggaggcaagccacgccggaagaat
ccccaggagggcctgtataacgagctgcagaaggataagatggccgaggcctac
agcgagatcggcatgaagggagagagaaggcgcggcaagggacacgacggc
ctgtaccagggcctgagcacagcaacaaaagacacctacgacgcactgcacatg
caggctctgccccctcggtaa |
| 5 | >ALLO-501_v1.4 | atgggaacctctctgctgtgctggatggctctgtgcctgctgggggccgatcacgc
tgacgcaagtggcgggggggggtccgaactgcccacacagggcaccttctcca
acgtgagcaccaacgtgagctccggcggaggaggcagccctgcaccaaggcc
ccctacaccagcacctaccatcgcatctcagccactgagcctgcgccccgaggcc
tgccggcctgcagcaggcggccgtgcacacccgcggcctggactttgcctgc
gatatctatatctgggcacctctggcaggcacatgtggcgtgctgctgctgagcctg
gtcatcaccctgtactgcaatcacaggaaccggagaagggtgtgcaagtgtccac
ggcccgtggtgagagcagagggaaggggctccctgctgacatgtggcgacgtg
gaggagaatcctggcccaatggagacagatacctgctgctgtgggtgctgctgc
tgtgggtgcccggctccaccggagaggtgcagctgcagcagtctggaccagagc
tgatcaagccaggagcatccgtgaagatgtcttgtaaggccagcggctatacattc
accagctacgtgatgcactgggtgaagcagaagccaggacagggcctggagtg
gatcggctatatcaatccttacaacgacggcaccaagtataacgagaagtttaagg
gcaaggccacactgacctctgataagtctagctccacagcctacatggagctgtct
agcctgaccagcgaggactccgccgtgtactattgcgccagaggcacatactatta
cggcagcagggtgttcgattactggggccagggcaccacactgaccgtgtcctct
ggaggaggaggctccggaggaggaggctctggcggcggcggcagcgacatc
gtgatgacacaggcagcaccttccatcccagtgaccccaggcgagtctgtgagca
tctcctgtcggagctccaagtccctgctgaactctaatggcaacacctatctgtactg
gtttctgcagcggcccggacagtccccacagctgctgatctataggatgagcaatc
tggcctccggcgtgccagatcgcttctctggcagcggctccggcacagccttacc
ctgaggatctctcgcgtggaggcagaggacgtgggcgtgtattactgcatgcagc
acctggagtacccattcacatttggcgcaggcaccaagctggagctgaagcgga
gcgaccccaccacaaccccagcacctcggccacccacaccagcacccaccatc
gcatctcagcctctgagcctgcgggccgaggcctgtaggcccgcagcaggagg
agcagtgcacacccggggcctggacttcgcctgcgatatctacatctgggcacca
ctggccggcacatgcggcgtgctgttactgagcctggtcatcaccctgtattgcaa
gcggggcagaaagaagctgctgtacatcttcaagcagccctttatgcggcctgtgc
agacaacccaggaggaggatggctgctcctgtagattccctgaggaggaggag
gaggatgtgagctgcgcgtgaagttttctcggagcgccgacgcaccagcatatca
gcagggacagaaccagctgtacaatgagctgaacctgggccggagagaggagt
atgacgtgctggataagagacggggccgggaccccgagatgggaggcaagcct
cgccggaagaatccacaggagggcctgtataacgagctgcagaaggataagatg
gccgaggcctacagcgagatcggcatgaaggagagagaaggcgcggcaag
ggacacgacggcctgtaccagggcctgagcacagcaacaaaagacacctacga
cgcactgcacatgcaggctctgccaccaagatga |
| 6 | ALLO-501_v1.5 | atggggacctcactgctgtgctggatggctctgtgcctgctgggggccgaccacg
ctgacgcctgctctggggggggggggggctcatgctccggaggaggaggctct
gagctgccaacccagggcacattctccaacgtgagcaccaacgtgtctcctgcca
agccaaccacaacgcatgcagcggcggaggaggaggcagctgttccggcgg
cggcggcagccctgccccaaggcccctaccccagcacctacaatcgcatctca
gcctctgagcctgcgcccagaggcctgtcggcccgcagcaggaggagcagtgc
acacccgcggcctggactttgcctgcgatatctatatctgggcaccactggcaggc
acctgtggcgtgctgctgctgagcctggtcatcaccctgtactgcaatcacaggaa
ccggagaagggtgtgcaagtgtccacgcccgtggtgagagcagagggaaggg
ggctctctgctgacctgtggcgacgtggaggagaatcctggccctatggagacag
atacactgctgctgtgggctgctgctgtgggtgcccggcagcacaggagaggt
gcagctgcagcagtccggacctgagctgatcaagccaggcgcctccgtgaagat
gtcttgcaaggccagcggctataccttcacaagctacgtgatgcactgggtgaagc
agaagccaggcaggggcctggagtggatcggctatatcaatccctcacaacgacg
gcaccaagtataacgagaagtttaagggcaaggccaccctgacaagcgataaga
gctcctctaccgcctacatggagctgagctccctgacaagcgaggactccgccgt
gtactattgcgccagaggcacctactattacggctccagggtgttcgattactgggg
ccagggcacaaaccctgacagtgtctagcggaggaggaggcagcggaggagga
ggctccggcggcggcggctctgacatcgtgatgacccaggcagcaccatccatc
cctgtgacaccaggcgagtctgtgagcatctcctgtcggtcctctaagtccctgctg
aactctaatggcaacacctatctgtactggtttctgcagcggcccggacagtctcct
cagctgctgatctataggatgagcaatctggcctccggcgtgcctgatcgcttctct
ggcagcggctccggcaccgcctttacactgaggatcagccgcgtggaggcaga
ggacgtgggcgtgtattactgcatgcagcacctggagtacccttttcacctttggcgc
cggcacaaagctggagctgaagcggagcgaccccacaaccacaccagcacctc
ggccacccaccccagcaccaacaatcgcatctcagccactgagcctgcggcccg
aggcctgtaggccagccgccggcggcgcagtgcacacccggggcctggacttc
gcctgcgatatctacatctgggccctctggccggcacctgcggcgtgctgttact
gagcctggtcatcaccctgtattgcaagcggggcagaaagaagctgctgtacatct |

SEQ ID NO. CHART

| SEQ ID NO | Description | Sequence |
|---|---|---|
|  |  | tcaagcagcccttcatgcggcccgtgcagaccacacaggaggaggatggctgct<br>cctgtagattcccagaggaggaggagggaggatgtgagctgcgcgtgaagttttc<br>tcggagcgccgacgcacctgcatatcagcagggacagaaccagctgtacaatga<br>gctgaacctgggccggagagaggagtatgacgtgctggataagagacggggcc<br>gggaccccgagatggggaggcaagccccgccggaagaatcctcaggagggcct<br>gtataacgagctgcagaaggataagatggccgaggcctacagcgagatcggcat<br>gaagggagagagaaggcgcggcaagggccacgacggcctgtaccagggcct<br>gtccacagcaacaaaggatacttatgacgctctgcacatgcaggctctgccccctc<br>ggtga |
| 7 | ALLO-501_v1.6 | atgggaaccagcctgctgtgctggatggcactgtgcctgctgggagcagaccac<br>gccgatgccgaactgcctactcaggggacattctctaatgtgagcaccaacgtga<br>gctctggaggaggaggctccgagctgccaacccagggcacattctctaatgtgag<br>cacaaacgtgtctcccgccaagcctaccacaaccgccgaactgcctacccaggg<br>cacattttccaacgtgtctaccaacgtgtctagcggaggaggaggctccccccgcac<br>ctaggcccctaccccagcaccaacaatcgcaagccagcctctgtccctgcgccc<br>agaggcatgcaggccagcagcaggaggagcagtgcacacccgcggcctggac<br>tttgcctgcgatatctatatctgggcaccactggcaggaacctgtggcgtgctgctg<br>ctgtctctggtcatcaccctgtactgcaatcacagaaaccggagaagggtgtgcaa<br>gtgtcctcggccagtggtgagagcagaggaagggcagcctgctgacctgtgg<br>cgacgtggaggagaatcccggccctatggagacagatacactgctgctgtgggt<br>gctgctgctgtgggtgccaggctctacaggagaggtgcagctgcagcagagcgg<br>acctgagctgatcaagccaggcgcctctgtgaagatgagctgcaaggcctccgg<br>ctataccttcacaagctacgtgatgcactgggtgaagcagaagccaggccaggc<br>ctggagtggatcggctatatcaatccctacaacgacggcaccaagtataacgaga<br>agtttaagggcaaggccaccctgacatccgataagagctcctctaccgcctacatg<br>gagctgagctccctgacatccgaggactctgccgtgtactattgcgccagaggca<br>cctactattacggctctagggtgttcgattactggggccagggcacaaccctgaca<br>gtgtctagcggaggaggaggctctggaggaggaggcagcggcggcggaggct<br>ccgacatcgtgatgacccaggcagcaccatccatccagtgacacctggcaggaga<br>gcgtgtccatctcttgtaggtcctctaagtctctgctgaacagcaatggcaacaccta<br>tctgtactggifictgcagcggcccggacagagccctcagctgctgatctataggat<br>gtccaatctggcctctggagtgcctgatcgcttcagcggctccggctctggaaccg<br>cctttacactgaggatctcccgcgtggaggcagaggacgtgggcgtgtattactgc<br>atgcagcacctggagtaccctttcaccttggcgccggcacaaagctggagctga<br>agcggagcgaccccacaaccacaccagcaccccggccaccaaccctgcccct<br>acaatcgcaagccagccactgtccctgcgggccggagcctgtagacctgccgcc<br>ggcggcgccgtccataccgcgggcctggatttgcctgcgatatctacattggc<br>ccctctggccggcacttgcgcgtgctgctgctgagcctggtcatcaccctgtattg<br>caagcggggcagaaagaagctgctgtacatcttcaagcagcccttcatgcggcc<br>gtgcagaccacacaggaggaggatggctgctcctgtagattcccagaggaggag<br>gagggaggatgtgagctgcgcgtgaagttagccggtccgccgacgcacctgca<br>tatcagcagggccagaaccagctgtacaatgagctgaacctgggccggagagag<br>gagtacgacgtgctggataagagaaggggacggggaccccgagatggggaggca<br>agccccgccggaagaatcctcaggagggcctgtataacgagctgcagaaggata<br>agatggccgaggcctacagcgagatcggcatgaagggagagagaaggcgcgg<br>caagggacacgacggcctgtatcagggcctgtccaccgccacaaaggacaccta<br>cgatgccctgcacatgcaggccctgcctccaagatga |
| 8 | ALLO-501_v1.0<br>(or ALLO-501)<br>Exemplary signal<br>sequence is<br>underlined | <u>MLTSLLCWMALCLLGADHADACPYSNPSLCSGGGG</u><br><u>SELPTQGTFSNVSTNVSPAKPTTTACPYSNPSLCSGG</u><br><u>GGSPAPRPPTPAPTIASQPLSLRPEACRPAAGGAVHT</u><br><u>RGLDFACDIYIWAPLAGTCGVLLLSLVITLYCNHRN</u><br><u>RRRVCKCPRPVVRA</u><br>[EGRGSLLTCGDVEENPGP]<br><u>METDTLLLWVLLLWVPGSTGEVQLQQSGPELIKPG</u><br><u>ASVKMSCKASGYTFTSYVMHWVKQKPGQGLEWIG</u><br>YINPYNDGTKYNEKFKGKATLTSDKSSTAYMELSS<br>LTSEDSAVYYCARGTYYYGSRVFDYWGQGTTLTVS<br>SGGGGSGGGGSGGGGSDIVMTQAAPSIPVTPGESVSI<br>SCRSSKSLLNSNGNTYLYWFLQRPGQSPQLLIYRMS<br>NLASGVPDRFSGSGSGTAFTLRISRVEAEDVGVYYC<br>MQHLEYPFTFGAGTKLELKRSDPTTTPAPRPPTPAPT<br>IASQPLSLRPEACRPAAGGAVHTRGLDFACDIYIWAP<br>LAGTCGVLLLSLVITLYCKRGRKKLLYIFKQPFMRP<br>VQTTQEEDGCSCRFPEEEEGGCELRVKFSRSADAPA<br>YQQGQNQLYNELNLGRREEYDVLDKRRGRDPEMG<br>GKPRRKNPQEGLYNELQKDKMAEAYSEIGMKGERR<br>RGKGHDGLYQGLSTATKDTYDALHMQALPPR |
| 9 | ALLO-501_v1.1 | <u>METDTLLLWVLLLWVPGSTGEVQLQQSGPELIKPG</u><br><u>ASVKMSCKASGYTFTSYVMHWVKQKPGQGLEWIG</u><br>YINPYNDGTKYNEKFKGKATLTSDKSSTAYMELSS<br>LTSEDSAVYYCARGTYYYGSRVFDYWGQGTTLTVS |

SEQ ID NO. CHART

| SEQ ID NO | Description | Sequence |
|---|---|---|
| | | SGGGGSGGGGSGGGGSDIVMTQAAPSIPVTPGESVSI SCRSSKSLLNSNGNTYLYWFLQRPGQSPQLLIYRMS NLASGVPDRFSGSGSGTAFTLRISRVEAEDVGVYYC MQHLEYPFTFGAGTKLELKRSDPTTTPAPRPPTPAPT IASQPLSLRPEACRPAAGGAVHTRGLDFACDIYIWAP LAGTCGVLLLSLVITLYCKRGRKKLLYIFKQPFMRP VQTTQEEDGCSCRFPEEEEGGCELRVKFSRSADAPA YQQGQNQLYNELNLGRREEYDVLDKRRGRDPEMG GKPRRKNPQEGLYNELQKDKMAEAYSEIGMKGERR RGKGHDGLYQGLSTATKDTYDALHMQALPPR |
| 10 | ALLO-501_v1.2 | METDTLLLWVLLLWVPGSTGEVQLQQSGPELIKPG ASVKMSCKASGYTFTSYVMHWVKQKPGQGLEWIG YINPYNDGTKYNEKFKGKATLTSDKSSTAYMELSS LTSEDSAVYYCARGTYYYGSRVFDYWGQTTLTVS SGGGGSGGGGSGGGGSDIVMTQAAPSIPVTPGESVSI SCRSSKSLLNSNGNTYLYWFLQRPGQSPQLLIYRMS NLASGVPDRFSGSGSGTAFTLRISRVEAEDVGVYYC MQHLEYPFTFGAGTKLELKRSDPTTTPAPRPPTPAPT IASQPLSLRPEACRPAAGGAVHTRGLDFACDIYIWAP LAGTCGVLLLSLVITLYCKRGRKKLLYIFKQPFMRP VQTTQEEDGCSCRFPEEEEGGCELRVKFSRSADAPA YQQGQNQLYNELNLGRREEYDVLDKRRGRDPEMG GKPRRKNPQEGLYNELQKDKMAEAYSEIGMKGERR RGKGHDGLYQGLSTATKDTYDALHMQALPPR |
| 11 | ALLO-501_v1.3 | MGTSLLCWMALCLLGADHADASGGGGSPAPRPPTP APTIASQPLSLRPEACRPAAGGAVHTRGLDFACDIYI WAPLAGTCGVLLLSLVITLYCNHRNRRRVCKCPRPV VRAEGRGSLLTCGDVEENPGPMETDTLLLWVLLLW VPGSTGEVQLQQSGPELIKPGASVKMSCKASGYTFT SYVMEIWVKQKPGQGLEWIGYINPYNDGTKYNEKF KGKATLTSDKSSTAYMELSSLTSEDSAVYYCARGT YYYGSRVFDYWGQTTLTVSSGGGGSGGGGSGGG GSDIVMTQAAPSIPVTPGESVSISCRSSKSLLNSNGNT YLYWFLQRPGQSPQLLIYRMSNLASGVPDRFSGSGS GTAFTLRISRVEAEDVGVYYCMQHLEYPFTFGAGTK LELKRSDPTTTPAPRPPTPAPTIASQPLSLRPEACRPA AGGAVHTRGLDFACDIYIWAPLAGTCGVLLLSLVIT LYCKRGRKKLLYIFKQPFMRPVQTTQEEDGCSCRFP EEEEGGCELRVKFSRSADAPAYQQGQNQLYNELNL GRREEYDVLDKRRGRDPEMGGKPRRKNPQEGLYNE LQKDKMAEAYSEIGMKGERRRGKGHDGLYQGLST ATKDTYDALHMQALPPR |
| 12 | ALLO-501_v1.4 | MGTSLLCWMALCLLGADHADASGGGGSELPTQGTF SNVSTNVSSGGGGSPAPRPPTPAPTIASQPLSLRPEAC RPAAGGAVHTRGLDFACDIYIWAPLAGTCGVLLLSL VITLYCNHRNRRRVCKCPRPVVRAEGRGSLLTCGD VEENPGPMETDTLLLWVLLLWVPGSTGEVQLQQSG PELIKPGASVKMSCKASGYTFTSYVMHWVKQKPGQ GLEWIGYINPYNDGTKYNEKFKGKATLTSDKSSSTA YMELSSLTSEDSAVYYCARGTYYYGSRVFDYWGQ GTTLTVSSGGGGSGGGGSGGGGSDIVMTQAAPSIPV TPGESVSISCRSSKSLLNSNGNTYLYWFLQRPGQSPQ LLIYRMSNLASGVPDRFSGSGSGTAFTLRISRVEAED VGVYYCMQHLEYPFTFGAGTKLELKRSDPTTTPAPR PPTPAPTIASQPLSLRPEACRPAAGGAVHTRGLDFAC DIYIWAPLAGTCGVLLLSLVITLYCKRGRKKLLYIFK QPFMRPVQTTQEEDGCSCRFPEEEEGGCELRVKFSR SADAPAYQQGQNQLYNELNLGRREEYDVLDKRRG RDPEMGGKPRRKNPQEGLYNELQKDKMAEAYSEIG MKGERRRGKGHDGLYQGLSTATKDTYDALHMQAL PPR |
| 13 | ALLO-501_v1.5 | MGTSLLCWMALCLLGADHADACSGGGGGSCSGGG GSELPTQGTFSNVSTNVSPAKPTTTACSGGGGGSCS GGGGSPAPRPPTPAPTIASQPLSLRPEACRPAAGGAV HTRGLDFACDIYIWAPLAGTCGVLLLSLVITLYCNH RNRRRVCKCPRPVVRAEGRGSLLTCGDVEENPGPM ETDTLLLWVLLLWVPGSTGEVQLQQSGPELIKPGAS VKMSCKASGYTFTSYVMHWVKQKPGQGLEWIGYI NPYNDGTKYNEKFKGKATLTSDKSSTAYMELSSLT SEDSAVYYCARGTYYYGSRVFDYWGQTTLTVSSG |

SEQ ID NO. CHART

| SEQ ID NO | Description | Sequence |
|---|---|---|
| | | GGGSGGGGSGGGGSDIVMTQAAPSIPVTPGESVSISC<br>RSSKSLLNSNGNTYLYWFLQRPGQSPQLLIYRMSNL<br>ASGVPDRFSGSGSGTAFTLRISRVEAEDVGVYYCMQ<br>HLEYPFTFGAGTKLELKRSDPTTTPAPRPPTPAPTIAS<br>QPLSLRPEACRPAAGGAVHTRGLDFACDIYIWAPLA<br>GTCGVLLLSLVITLYCKRGRKKLLYIFKQPFMRPVQ<br>TTQEEDGCSCRFPEEEEGGCELRVKFSRSADAPAYQ<br>QGQNQLYNELNLGRREEYDVLDKRRGRDPEMGGK<br>PRRKNPQEGLYNELQKDKMAEAYSEIGMKGERRRG<br>KGHDGLYQGLSTATKDTYDALHMQALPPR |
| 14 | ALLO-501_v1.6 | MGTSLLCWMALCLLGADHADAELPTQGTFSNVSTN<br>VSSGGGGSELPTQGTFSNVSTNVSPAKPTTTAELPTQ<br>GTFSNVSTNVSSGGGGSPAPRPPTPAPTIASQPLSLRP<br>EACRPAAGGAVHTRGLDFACDIYIWAPLAGTCGVL<br>LLSLVITLYCNHRNRRRVCKCPRPVVRAEGRGSLLT<br>CGDVEENPGPMETDTLLLWVLLLWVPGSTGEVQLQ<br>QSGPELIKPGASVKMSCKASGYTFTSYVMHWVKQK<br>PGQGLEWIGYINPYNDGTKYNEKFKGKATLTSDKSS<br>STAYMELSSLTSEDSAVYYCARGTYYYGSRVFDYW<br>GQGTTLTVSSGGGGSGGGGSGGGGSDIVMTQAAPSI<br>PVTPGESVSISCRSSKSLLNSNGNTYLYWFLQRPGQS<br>PQLLIYRMSNLASGVPDRFSGSGSGTAFTLRISRVEA<br>EDVGVYYCMQHLEYPFTFGAGTKLELKRSDPTTTP<br>APRPPTPAPTIASQPLSLRPEACRPAAGGAVHTRGLD<br>FACDIYIWAPLAGTCGVLLLSLVITLYCKRGRKKLL<br>YIFKQPFMRPVQTTQEEDGCSCRFPEEEEGGCELRV<br>KFSRSADAPAYQQGQNQLYNELNLGRREEYDVLDK<br>RRGRDPEMGGKPRRKNPQEGLYNELQKDKMAEAY<br>SEIGMKGERRRGKGHDGLYQGLSTATKDTYDALH<br>MQALPPR |
| 15 | EF1alpha (long 1189)_promoter_ GRCh38.p12_(v1.0_v1.1_v1.3_v1.4_v1.5_v1.6) | gcgtgaggctccggtgcccgtcagtgggcagagcgcacatcgcccacagtcccc<br>gagaagttggggggaggggtcggcaattgaaccggtgcctagagaaggtggcg<br>cggggtaaactgggaaagtgatgtcgtgtactggctccgccttttttcccgagggtg<br>ggggagaaccgtatataagtgcagtagtcgccgtgaacgttCTTTTTCGC<br>AACGGGTTTGCCGCCAGAACACAGgtaagtgccgtgtgtgg<br>ttccccgcgggcctggcctcttacgggtatggcccttgcgtgccttgaattacttcc<br>acgcccctggctgcagtacgtgattcttgatcccgagcttcgggttggaagtgggt<br>gggagagttcgaggccttgcgcttaaggagccccttcgcctcgtgcttgagttgag<br>gcctggcctgggcgctggggccgccgcgtgcgaatctggtggcaccttcgcgcc<br>tgtctcgctgattcgataagtctctagccattaaaattttttgatgacctgctgcgacg<br>ctttttttctggcaagatagtcttgtaaatgcgggccaagatctgcacactggtatttc<br>ggttttttggggccgcgggcggcgacggggcccgtgcgtcccagcgcacatgttc<br>ggcgaggcggggcctgcgagcgcggccaccgagaatcggacgggggtagtct<br>caagctggccggcctgctctggtgcctggcctcgcgccgccgtgtatcgccccgc<br>cctgggcggcaaggctggcccggtcggcaccagttgcgtgagcggaaagatgg<br>ccgcttcccggccctgctgcagggagctcaaaatggaggacgcggcgctcggg<br>agagcgggcgggtgagtcacccacacaaaggaaaagggcctttccgtcctcagc<br>cgtcgcttcatgtgactccacggagtaccgggcgccgtccaggcacctcgattagt<br>tctcgagatttggagtacgtcgtattaggttgggggagggtttttatgcgatgga<br>gtttccccacactgagtgggtggagactgaagttaggccagcttggcacttgatgta<br>attctccttggaatttgccctttttgagtttggatcttggttcattctcaagcctcagaca<br>gtggttcaaagttttttttcttccatttcagGTGTCGTGA |
| 16 | >EF1alpha_(short_ 237)_promoter_ GRCh38.p12_(v1.2) | gcgtgaggctccggtgcccgtcagtgggcagagcgcacatcgcccacagtcccc<br>gagaagttggggggaggggtcggcaattgaaccggtgcctagagaaggtggcg<br>cggggtaaactgggaaagtgatgtcgtgtactggctccgccttttttcccgagggtg<br>ggggagaaccgtatataagtgcagtagtcgccgtgaacgttCTTTTTCGC<br>AACGGGTTTGCCGCCAGAACACAG |
| 17 | 4G7 immunoglobulin gamma 1 heavy chain | MEWSWIFLFLLSGTAGVHSEVQLQQSGPELIKPGAS<br>VKMSCKASGYTFTSYVMHWVKQKPGQGLEWIGYI<br>NPYNDGTKYNEKFKGKATLTSDKSSSTAYMELSSLT<br>SEDSAVYYCARGTYYYGSRVFDYWGQGTTLTVSSA<br>KTTPPSVYPLAPGSAAQTNSMVTLGCLVKGYFPEPV<br>TVTWNSGSLSSGVHTFPAVLQSDLYTLSSSVTVPSST<br>WPSETVTCNVAHPASSTKVDKKIVPRDCGCKPCICT<br>VPEVSSVFIFPPKPKDVLTITLTPKVTCVVVDISKDDP<br>EVQFSWFVDDVEVHTAQTQPREEQFNSTFRSVSELPI<br>MHQDWLNGKEFKCRVNSAAFPAPIEKTISKTKGRPK<br>APQVYTIPPPKEQMAKDKVSLTCMITDFFPEDITVE<br>WQWNGQPAENYKNTQPIMDTDGSYFVYSKLNVQK<br>SNWEAGNTFTCSVLHEGLHNHHTEKSLSHSPGK |

-continued

| SEQ ID NO | Description | Sequence |
|---|---|---|
| 18 | 4G7 immunoglobulin kappa light chain | MRCLAEFLGLLVLWIPGAIGDIVMTQAAPSIPVTPGE SVSISCRSSKSLLNSNGNTYLYWFLQRPGQSPQLLIY RMSNLASGVPDRFSGSGSGTAFTLRISRVEAEDVGV YYCMQHLEYPFTFGAGTKLELKRADAAPTVSIFPPS SEQLTSGGASVVCFLNNIFYPKDINVKWKIDGSERQN GVLNSWTDQDSKDSTYSMSSTLTLTKDEYERHNSY TCEATHKTSTSPIVKSFNRNEC |
| 19 | RQR8 | CPYSNPSLCSGGGGSELPTQGTFSNVSTNVSPAKPTT TACPYSNPSLCSGGGGSP APRPPTPAPTIASQPLSLRPEACRPAAGGAVHTRGLD FACDIYIWAPLAGTCGVLLLS LVITLYCNHRNRRRVCKCPRPVV |
| 20 | Suicide peptide signal sequence | MGTSLLCWMALCLLGADHADA |
| 21 | Signal Sequence and RQR8 | MGTSLLCWMALCLLGADHADACPYSNPSLCSGGG GSELPTQGTFSNVSTNVSPAKPTTTACPYSNPSLCSG GGGSPAPRPPTPAPTIASQPLSLRPEACRPAAGGAVH TRGLDFACDIYIWAPLAGTCGVLLLSLVITLYCNHR NRRRVCKCPRPVV |
| 22 | Rituximab mimotope | CPYSNPSLC |
| 23 | Palivizumab epitope | NSELLSLINDMPITNDQKKLMSNN |
| 24 | Cetuximab mimotope 1 | CQFDLSTRRLKC |
| 25 | Cetuximab mimotope 2 | CQYNLSSRALKC |
| 26 | Cetuximab mimotope 3 | CVWQRWQKSYVC |
| 27 | Cetuximab mimotope 4 | CMWDRFSRWYKC |
| 28 | Nivolumab Epitope 1 | SFVLNWYRMSPSNQTDKLAAFPEDR |
| 29 | Nivolumab Epitope 2 | SGTYLCGAISLAPKAQIKE |
| 30 | QBEND-10 Epitope | ELPTQGTFSNVSTNVS |
| 31 | Alemtuzumab epitope | GQNDTSQTSSPS |
| 32 | FcγRIIIα hinge | GLAVSTISSFFPPGYQ |
| 33 | CD8α hinge | TTTPAPRPPTPAPTIASQPLSLRPEACRPAAGGAVHT RGLDFACD |
| 34 | IgG1 hinge | EPKSPDKTHTCPPCPAPPVAGPSVFLFPPKPKDTLMI ARTPEVTCVVVDVSHEDPEVKFNWYVDGVEVHNA KTKPREEQYNSTYRVVSVLTVLHQDWLNGKEYKC KVSNKALPAPIEKTISKAKGQPREPQVYTLPPSRDEL TKNQVSLTCLVKGFYPSDIAVEWESNGQPENNYKTT PPVLDSDGSFFLYSKLTVDKSRWQQGNVFSCSVMH EALHNHYTQKSLSLSPGK |
| 35 | CD8α transmembrane | IYIWAPLAGTCGVLLLSLVIT |
| 36 | CD8α hinge/ transmembrane | TTTPAPRPPTPAPTIASQPLSLRPEACRPAAGGAVHT RGLDFACDIYIWAPLAGTCGVLLLSLVIT |

-continued

SEQ ID NO. CHART

| SEQ ID NO | Description | Sequence |
|---|---|---|
| 37 | 41BB (intracellular domain) | KRGRKKLLYIFKQPFMRPVQTTQEEDGCSCRFPEEE EGGCEL |
| 38 | CD3ζ cytoplasmic signaling domain | LRVKFSRSADAPAYQQGQNQLYNELNLGRREEYDV LDKRRGRDPEMGGKPRRKNPQEGLYNELQKDKMA EAYSEIGMKGERRRGKGHDGLYQGLSTATKDTYDA LHMQALPPR |
| 39 | EF1a first intron | GTAAGTGCCGTGTGTGGTTCCCGCGGGCCTGGCCT CTTTACGGGTTATGGCCCTTGCGTGCCTTGAATTA CTTCCACGCCCCTGGCTGCAGTACGTGATTCTTGA TCCCGAGCTTCGGGTTGGAAGTGGGTGGGAGAGT TCGAGGCCTTGCGCTTAAGGAGCCCCTTCGCCTCG TGCTTGAGTTGAGGCCTGGCCTGGGCGCTGGGGC CGCCGCGTGCGAATCTGGTGGCACCTTCGCGCCTG TCTCGCTGCTTTCGATAAGTCTCTAGCCATTTAAA ATTTTTGATGACCTGCTGCGACGCTTTTTTTCTGGC AAGATAGTCTTGTAAATGCGGGCCAAGATCTGCA CACTGGTATTTCGGTTTTTGGGGCCGCGGGCGGCG ACGGGGCCCGTGCGTCCCAGCGCACATGTTCGGC GAGGCGGGGCCTGCGAGCGCGGCCACCGAGAATC GGACGGGGGTAGTCTCAAGCTGGCCGGCCTGCTC TGGTGCCTGGCCTCGCGCCGCCGTGTATCGCCCCG CCCTGGGCGGCAAGGCTGGCCCGGTCGGCACCAG TTGCGTGAGCGGAAAGATGGCCGCTTCCCGGCCC TGCTGCAGGGAGCTCAAAATGGAGGACGCGGCGC TCGGGAGAGCGGGCGGGTGAGTCACCCACACAAA GGAAAAGGGCCTTTCCGTCCTCAGCCGTCGCTTCA TGTGACTCCACGGAGTACCGGGCGCCGTCCAGGC ACCTCGATTAGTTCTCGAGCTTTTGGAGTACGTCG TCTTTAGGTTGGGGGGAGGGGTTTTATGCGATGG AGTTTCCCCACACTGAGTGGGTGGAGACTGAAGT TAGGCCAGCTTGGCACTTGATGTAATTCTCCTTGG AATTTGCCCTTTTTGAGTTTGGATCTTGGTTCATTC TCAAGCCTCAGACAGTGGTTCAAAGTTTTTTTCTT CCATTTCAG |
| 40 | LQL8 | CSGGGGGSCSGGGGSELPTQGTFSNVSTNVSPAKPT TTACSGGGGGSCSGGGGSPAPRPPTPAPTIASQPLSL RPEACRPAAGGAVHTRGLDFACDIYIWAPLAGTCG VLLLSLVITLYCNHRNRRRVCKCPRPVV |

What is claimed is:

1. An isolated polynucleotide encoding a polypeptide comprising an anti-CD19 chimeric antigen receptor (CAR) that comprises the amino acid sequence of SEQ ID NO: 9, wherein the polypeptide does not comprise a rituximab binding site, wherein the polynucleotide comprises a nucleic acid sequence having at least 90% identity to SEQ ID NO: 3 and a short EF1a promoter that is capable of expressing the anti-CD19 chimeric antigen receptor (CAR) in a mammalian T cell, and wherein the short EF1a promoter comprises the nucleic acid sequence of SEQ ID NO:16 and does not comprise the nucleic acid sequence of SEQ ID NO:39.

2. The isolated polynucleotide of claim 1, wherein the polypeptide further comprises a safety switch.

3. The isolated polynucleotide of claim 2, wherein the safety switch is linked to the CD19 CAR using a linker peptide.

4. The isolated polynucleotide of claim 2, wherein the safety switch is linked to the anti-CD19 CAR using a T2A linker.

5. The isolated polynucleotide of claim 2, wherein the safety switch comprises an antibody binding site.

6. The isolated polynucleotide of claim 2, wherein the polypeptide comprises a CD34 epitope.

7. The isolated polynucleotide of claim 6, wherein the CD34 epitope is a QBEND-10 epitope.

8. The isolated polynucleotide of claim 1, wherein the polypeptide further comprises a CD8 hinge/transmembrane domain.

9. The isolated polynucleotide of claim 1, wherein the polynucleotide encodes a polypeptide that comprises any one of the amino acid sequences of SEQ ID NOs: 11-14.

10. A vector comprising the isolated polynucleotide of claim 1.

11. The vector of claim 10, wherein the vector is a retroviral vector, a DNA vector, a plasmid, an RNA vector, an adenoviral vector, an adenovirus associated vector, a lentiviral vector, or any combination thereof.

12. An engineered immune cell comprising the isolated polynucleotide of claim 1, wherein the engineered immune cell does not express a rituximab binding site.

13. An engineered immune cell comprising the vector of claim 10, wherein the engineered immune cell does not express a rituximab binding site.

14. The engineered immune cell of claim 12, wherein the immune cell is a T cell, tumor infiltrating lymphocyte (TIL), NK cell, TCR-expressing cell, dendritic cell, or NK-T cell.

15. The engineered immune cell of claim 14, wherein the cell is an autologous T cell.

16. The engineered immune cell of claim 14, wherein the cell is an allogeneic T cell.

17. The engineered immune cell of claim 12, wherein the cell is resistant to rituximab.

18. A pharmaceutical composition comprising the engineered immune cell of claim 12 and a pharmaceutically acceptable excipient.

19. The isolated polynucleotide of claim 1, wherein the polynucleotide comprises a nucleic acid sequence having at least 95% identity to SEQ ID NO: 3.

20. The isolated polynucleotide of claim 1, wherein the polynucleotide comprises a nucleic acid sequence having at least 96% identity to SEQ ID NO: 3.

21. The isolated polynucleotide of claim 1, wherein the polynucleotide comprises a nucleic acid sequence having at least 98% identity to SEQ ID NO: 3.

22. The isolated polynucleotide of claim 1, wherein the polynucleotide comprises a nucleic acid sequence having at least 99% identity to SEQ ID NO: 3.

23. The isolated polynucleotide of claim 1, wherein the polynucleotide comprises the nucleic acid sequence shown in SEQ ID NO: 3.

* * * * *